(12) United States Patent
Champion et al.

(10) Patent No.: US 12,286,652 B2
(45) Date of Patent: *Apr. 29, 2025

(54) VARIANTS OF TERMINAL DEOXYNUCLEOTIDYL TRANSFERASE AND USES THEREOF

(71) Applicants: DNA Script, Le Kremlin-Bicêtre (FR); Institut Pasteur, Paris (FR); Centre National De La Recherche Scientifique, Paris (FR)

(72) Inventors: Elise Champion, Paris (FR); Mikhael Soskine, Franconville (FR); Thomas Ybert, Paris (FR); Marc Delarue, Versailles (FR)

(73) Assignees: DNA Script, Le Kremlin-Bicêtre (FR); Institut Pasteur, Paris (FR); Centre National de la Recherche Scientifque, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/636,074

(22) Filed: Apr. 15, 2024

(65) Prior Publication Data

US 2024/0254459 A1 Aug. 1, 2024

Related U.S. Application Data

(63) Continuation of application No. 17/544,647, filed on Dec. 7, 2021, now Pat. No. 12,071,638, which is a continuation of application No. 16/925,785, filed on Jul. 10, 2020, now Pat. No. 11,208,637, which is a continuation of application No. 16/423,972, filed on May 28, 2019, now Pat. No. 10,752,887, which is a continuation-in-part of application No. 16/242,904, filed on Jan. 8, 2019, now Pat. No. 10,435,676.

(30) Foreign Application Priority Data

Jan. 8, 2018 (EP) ..................................... 18305006

(51) Int. Cl.
C12N 15/70 (2006.01)
C12N 9/12 (2006.01)

(52) U.S. Cl.
CPC ........... *C12N 9/1264* (2013.01); *C12N 15/70* (2013.01); *C12Y 207/07031* (2013.01)

(58) Field of Classification Search
CPC combination set(s) only.
See application file for complete search history.

(56) References Cited

U.S. PATENT DOCUMENTS

| | | |
|---|---|---|
| 4,448,883 A | 5/1984 | Case |
| 4,772,691 A | 9/1988 | Herman |
| 5,436,143 A | 7/1995 | Hyman |
| 5,516,664 A | 5/1996 | Hyman |
| 5,602,000 A | 2/1997 | Hyman |
| 5,656,745 A | 8/1997 | Bischofberger |
| 5,744,595 A | 4/1998 | Srivastava et al. |
| 5,763,594 A | 6/1998 | Hiatt et al. |
| 5,808,045 A | 9/1998 | Hiatt et al. |
| 5,872,244 A | 2/1999 | Hiatt |
| 5,917,031 A | 6/1999 | Miura |
| 5,935,527 A | 8/1999 | Andrus |
| 5,990,300 A | 11/1999 | Hiatt |
| 6,214,987 B1 | 4/2001 | Hiatt |
| 6,232,465 B1 | 5/2001 | Hiatt |
| 6,623,929 B1 | 9/2003 | Densham |
| 6,777,189 B2 | 8/2004 | Wei |
| 7,057,026 B2 | 6/2006 | Barnes et al. |
| 7,078,499 B2 | 7/2006 | Odedra |
| 7,125,671 B2 | 10/2006 | Sood |
| 7,270,951 B1 | 9/2007 | Stemple |
| 7,407,757 B2 | 8/2008 | Brenner |
| 7,494,797 B2 | 2/2009 | Mueller |
| 7,544,794 B1 | 6/2009 | Benner |
| 7,939,259 B2 | 5/2011 | Kokoris |
| 8,034,923 B1 | 10/2011 | Benner et al. |
| 8,212,020 B2 | 7/2012 | Benner et al. |
| 8,263,335 B2 | 9/2012 | Carr |
| 8,674,086 B2 | 3/2014 | Liu |
| 8,808,988 B2 | 8/2014 | Zhao et al. |
| 8,808,989 B1 | 8/2014 | Efcavitch |
| 9,896,709 B2 | 2/2018 | Makarov |
| 10,059,929 B2 | 8/2018 | Efcavitch |
| 10,435,676 B2 | 10/2019 | Champion et al. |

(Continued)

FOREIGN PATENT DOCUMENTS

| | | |
|---|---|---|
| WO | 2015159023 A1 | 10/2015 |
| WO | 2016064880 A1 | 4/2016 |

(Continued)

OTHER PUBLICATIONS

Accession No. A4PCE2, (2007). 2 pages.

(Continued)

*Primary Examiner* — Tekchand Saidha
(74) *Attorney, Agent, or Firm* — MORRISON & FOERSTER LLP

(57) ABSTRACT

The present invention relates to variants of Terminal deoxynucleotidyl Transferase (TdT), each of which (i) has an amino acid sequence similarity to SEQ ID NO: 2, 11, 13, 15, 17, 19, 21, 23, 25, 27, 29, 31, 33 or 35 with corresponding amino acid substitutions, (ii) is capable of synthesizing a nucleic acid fragment without a template and (iii) is capable of incorporating a modified nucleotide into the nucleic acid fragment.

14 Claims, 2 Drawing Sheets

Specification includes a Sequence Listing.

(56) References Cited

U.S. PATENT DOCUMENTS

| | | | | |
|---|---|---|---|---|
| 10,752,887 B2* | 8/2020 | Champion | ..... | C12Y 207/07031 |
| 11,208,637 B2 | 12/2021 | Champion | | |
| 12,071,638 B2* | 8/2024 | Champion | ..... | C12Y 207/07031 |
| 2006/0240439 A1 | 10/2006 | Smith | | |
| 2014/0363851 A1 | 12/2014 | Efcavitch | | |
| 2014/0363852 A1 | 12/2014 | Efcavitch | | |
| 2016/0108382 A1 | 4/2016 | Efcavitch | | |
| 2018/0016609 A1 | 1/2018 | Chen | | |
| 2018/0023108 A1 | 1/2018 | Chen | | |
| 2018/0274001 A1 | 9/2018 | Efcavitch | | |
| 2018/0312820 A1 | 11/2018 | Pomerantz | | |
| 2019/0211315 A1 | 7/2019 | Champion | | |
| 2019/0390178 A1 | 12/2019 | Champion | | |
| 2020/0002690 A1 | 1/2020 | Ybert | | |
| 2021/0009970 A1 | 1/2021 | Champion | | |
| 2022/0403354 A1 | 12/2022 | Champion | | |

FOREIGN PATENT DOCUMENTS

| | | |
|---|---|---|
| WO | 2016128731 A1 | 8/2016 |
| WO | 2017075421 A1 | 5/2017 |
| WO | 2017216472 A2 | 12/2017 |
| WO | 2017216472 A3 | 3/2018 |
| WO | 2018102818 A1 | 6/2018 |
| WO | 2018215803 A1 | 11/2018 |

OTHER PUBLICATIONS

Aoufouchi, S. et al. (2000). "Two Novel Human and Mouse DNA Polymerases of the PoIX Family," Nucleic Acids Research 28(18):3684-3693.

Arana, M.E. et al. (2008) "Low-Fidelity DNA Synthesis by Human DNA Polymerase Theta," Nucleic Acids Research 36(11):3847-3856.

Beabealashvilli, R.S. et al. (1986). "Nucleoside 5'-Triphosphates Modified at Sugar Residues as Substrates for Calf Thymus Terminal Deoxynucleotidyl Transferase and for AMV Reverse Transcriptase," Biochim. Biophys. Acta., 868(2-3):136-144.

Belousov, E.S. et al. (1997). "Sequence-Specific Targeting and Covalent Modification of Human Genomic DNA," Nucleic Acids Res. 25(17):3440-3444.

Benatolila, L.A. et al. (1995). "The Two Isoforms of Mouse Terminal Deoxynucleotidyl Transferase Differ in Both the Ability to Add N Regions and Subcellular Localization," The EMBO Journal 14(17):4221-4229.

Boule, J-B. et al. (1998). "High-Level Expression of Murine Terminal Deoxynucleotidyl Transferase in *Escherichia coli* Grown at Low Temperature and Overexpressing argU tRNA," Molecular Biotechnology 10:199-208.

Database EPO Proteins, "Sequence 8 from Patent WO2016128731", XP002779827, Oct. 5, 2016, 1 page.

Database Refseq (2016) Predicted: DNA polymerase theta isoform X1 [Rhinolophus sinicus], XP-002776331, 2 pages.

Database UniProt, SubName: Full=DNA nucleotidylexotransferase isoform X1, XP002779838, May 10, 2017, 8 pages.

Delarue, M. et al. (2002). "Crystal Structures of a Template-Independent DNA Polymerase: Murine Terminal Deoxynuclotidyltransferase," EMBO J. 21(3):427-439.

Dominguez, O. et al. (2000). "DNA Polymerase mu (Polμ), Homologous to TdT, Could Act as a DNA Mutator in Eukaryotic Cells," The EMBO Journal 19(17):1731-1742.

Flickinger, J.L. et al. (1992). "Differential Incorporation of Biotinylated Nucleotides by Terminal Deoxynucleotidyl Transferase," Nucleic Acids Research, 20(9):2382.

Gouge, G. et al. (2015). "Structures of Intermediates Along the Catalytic Cycle of Terminal Deoxynucleotidyltransferase: Dynamical Aspects of the Two-Metal Ion Mechanism," J. Mol. Biol. 425:4334-4352.

Hogg, M. et al. (2012, e-pub. Dec. 1, 2011) "Promiscuous DNA Synthesis by Human DNA Polymerase θ," Nucleic Acids Research 40(6):2611-2622.

International Search Report from PCT International Application No. PCT/EP2018/071217 dated Feb. 14, 2019, 4 pages.

International Search Report from PCT International Application No. PCT/EP2019/050334 dated Feb. 22, 2019, 17 pages.

International Search Report from PCT International Application No. PCT/FR2017/051519 dated Jan. 18, 2018, 3 pages.

Jensen, M.A. et al. (Mar. 27, 2018). "Template-Independent Enzymatic Oligonucleotide Synthesis (TIEOS): Its History, Prospects, and Challenges," Biochemistry 57(12):1821-1832, 31 pages.

Knapp, D.C. et al. (2011). "Fluoride-Cleavable, Fluorescently Labelled Reversible Terminators: Synthesis and Use in Primer Extension," Chem. Eur. J. 17:2903-2915.

Kodumal, S.J. et al. (Nov. 2, 2004). "Total Synthesis of Long DNA Sequences: Synthesis of a Contiguous 32-κb Polyketide Synthase Gene Cluster," Proc. Natl. Acad. Sci. 101(44): 15573-15578.

Koiwai, O. et al. (1986). "Isolation and Characterization of Bovine and Mouse Terminal Deoxynucleotidyltransferase cDNAS Expressible in Mammalian Cells," Nucleic Acids Research 14(14): 5777-5792.

Li, Y. et al. (1998) "Crystal structures of open and closed forms of binary and ternary complexes of the large fragment of Thermus aquaticus DNA polymerase I: structural basis for nucleotide incorporation," Embo J. 17(24): 7514-7525.

Michelson, A.M. et al. (Dec. 25, 1982). "Characterization of the Homopolymer Tailing Reaction Catalyzed by Terminal Deoxynucleotidyl Transferase," J. Biol. Chem. 257(24):14773-14782.

Motea, E.A. et al. (May 2010). "Terminal Deoxynucleotidyl Transferase: The Story of a misguided DNA Polymerase," Biochim. Biophs. Acta 1804(5):1151-1166, 33 pages.

Patel, P.H. et al. (May 9, 2000) "DNA Polymerase Active Site is Highly Mutable: Evolutionary Consequences," Proc. Natl. Acad. Sci. USA 97(10): 5095-5100.

PIR Accession No. 151658, published Sep. 13, 1996 (Year: 1996), 2 pages.

PIR Accession No. A23595, published Sep. 10, 1999 (Year: 1999), 3 pages.

PIR Accession No. S55786, published Oct. 27, 1995 (Year: 1995), 2 pages.

PIR Accession No. WXHU, published Dec. 4, 1986 (Year: 1986), 2 pages.

Romain, F. et al. (2009). "Conferring a Template-Dependent Polymerase Activity to Terminal Deoxynucleotidyltransferase by Mutations in the Loop1 Region," Nucleic Acids Research, 37(14):4642-4656.

Schmitz, C. et al. (Nov. 6, 1999). "Solid-Phase Enzymatic Synthesis of Oligonucleotides," Organic Lett. 1(11):1729-1731.

Schott, H. et al. (1984). "Single-Step Elongation of Oligodeoxynucleotides Using Terminal Deoxynucleotidyl Transferase," Eur. J. Biochem. 143:613-620.

Schultz, H.J. et al. (2015) "Taq DNA Polymerase Mutants and 2'-Modified Sugar Recognition," Biochemistry 54:5999-6008.

Shima, N. et al. (2003) "Phenotype-Based Identification of Mouse Chromosome Instability Mutants," Genetics 163:1031-1040.

Singapore Patent Office, Written Opinion in Singapore Patent Application No. 11201809961T (dated Apr. 24, 2020). 11 pages.

Song, L.F. et al. (2021) "Large-Scale de novo Oligonucleotide Synthesis for Whole-Genome Synthesis and data Storage," Frontiers Bioeng. Biotechnol. 9:689797, 1-13.

Stemmer, W.P.C. et al. (1995). "Single-Step Assembly of a Gene and Entire Plasmid From Large Numbers of Oligodeoxyribonucleotides," Gene 164:49-53.

Troshchynsky, A. et al. (2015). "Functional Analyses of Polymorphic Variants of Human Terminal Deoxynucleotidyl Transferase," Genes and Immunity, 16:388-398.

UD-Dean, S.M.M. (2008). "A Theoretical Model for Template-Free Synthesis of Long DNA Sequence," Syst. Synth. Biol. 2: 67-73.

Uniprot, Accession No. 075417 (2016) www.uniprot.org. 8 pages.

Written Opinion from PCT International Application No. PCT/FR2017/051519 dated Jan. 18, 2018, 8 pages.

(56) References Cited

OTHER PUBLICATIONS

Written Opinion from PCT International Application No. PCT/EP2018/071217 dated Feb. 14, 2019, 6 pages.
Written Opinion from PCT International Application No. PCT/FR2017/051519 dated Jan. 18, 2018, 8 pages.
Yamtich, J. et al. (May 2010). "DNA Polymerase Family X: Function, Structure, and Cellular Roles," Biochim. Biophys. Acta. 1804(5):1136-1150, 35 pages.
Yang, B et al. (1994). "Mutational Analysis of Residues in the Nucleotide Binding Domain of Human Terminal Deoxynucleotidyl Transferase," Journal of Biological Chemistry 269(16):11859-11868.
Yang, B. et al. (1995). "T-Cell Specific Avian TdT: Characterization of the cDNA and Recombinant Enzyme," Nucleic Acids Research 23(11):2041-2048.
Yousefzadeh, M.J. et al. (2014) "Mechanism of Suppression of Chromosomal Instability by DNA Polymerase POLQ" PLOS Genetics 10(10): e1004654, 15 pages.
Zahn, K.E. et al. (2015) "Human DNA Polymerase θ Grasps the Primer Terminus to Mediate DNA Repair," Nat. Struc. Mol. Biol. 22(4):304-311, 25 pages.
Database REFSEQ [Online] Feb. 19, 2014 (Feb. 19, 2014), "Predicted: DNA nucleotidylexotransferase isoform X1 [Chrysochloris asiatica].", XP55824649, retrieved from NCBI, Database accession No. XP 006831251.1, 2 pages.

\* cited by examiner

SEQUENCE LISTING

```
Sequence total quantity: 35
SEQ ID NO: 1          moltype = AA  length = 510
FEATURE               Location/Qualifiers
source                1..510
                      mol_type = protein
                      organism = Mus musculus
SEQUENCE: 1
MDPLQAVHLG PRKKRPRQLG TPVASTPYDI RFRDLVLFIL EKKMGTTRRA FLMELARRKG  60
FRVENELSDS VTHIVAENNS GSDVLEWLQL QNIKASSELE LLDISWLIEC MGAGKPVEMM 120
GRHQLVVNRN SSPSPVPGSQ NVPAPAVKKI SQYACQRRTT LNNYNQLFTD ALDILAENDE 180
LRENEGSCLA FMRASSVLKS LPFPITSMKD TEGIPCLGDK VKSIIEGIIE DGESSEAKAV 240
LNDERYKSFK LFTSVFGVGL KTAEKWFRMG FRTLSKIQSD KSLRFTQMQK AGFLYYEDLV 300
SCVNRPEAEA VSMLVKEAVV TFLPDALVTM TGGFRRGKMT GHDVDFLITS PEATEDEEQQ 360
```

```
LLHKVTDFWK QQGLLLYCDI LESTFEKFKQ PSRKVDALDH FQKCFLILKL DHGRVHSEKS   420
GQQEGKGWKA IRVDLVMCPY DRRAFALLGW TGSRQFERDL RRYATHERKM MLDNHALYDR   480
TKRVFLEAES EEEIFAHLGL DYIEPWERNA                                   510

SEQ ID NO: 2            moltype = AA  length = 381
FEATURE                 Location/Qualifiers
source                  1..381
                        mol_type = protein
                        organism = Mus musculus
SEQUENCE: 2
NSSPSPVPGS QNVPAPAVKK ISQYACQRRT TLNNYNQLFT DALDILAEND ELRENEGSCL   60
AFMRASSVLK SLPFPITSMK DTEGIPCLGD KVKSIIEGII EDGESSEAKA VLNDERYKSF   120
KLFTSVFGVG LKTAEKWFRM GFRTLSKIQS DKSLRFTQMQ KAGFLYYEDL VSCVNRPEAE   180
AVSMLVKEAV VTFLPDALVT MTGGFRRGKM TGHDVDFLIT SPEATEDEEQ QLLHKVTDFW   240
KQQGLLLYCD ILESTFEKFK QPSRKVDALD HFQKCFLILK LDHGRVHSEK SGQQEGKGWK   300
AIRVDLVMCP YDRRAFALLG WTGSRQFERD LRRYATHERK MMLDNHALYD RTKRVFLEAE   360
SEEEIFAHLG LDYIEPWERN A                                            381

SEQ ID NO: 3            moltype = AA  length = 494
FEATURE                 Location/Qualifiers
source                  1..494
                        mol_type = protein
                        organism = Homo sapiens
SEQUENCE: 3
MLPKRRRARV GSPSGDAASS TPPSTRFPGV AIYLVEPRMG RSRRAFLTGL ARSKGFRVLD   60
ACSSEATHVV MEETSAEEAV SWQERRMAAA PPGCTPPALL DISWLTESLG AGQPVPVECR   120
HRLEVAGPRK GPLSPAWMPA YACQRPTPLT HHNTGLSEAL EILAEAAGFE GSEGRLLTFC   180
RAASVLKALP SPVTTLSQLQ GLPHFGEHSS RVVQELLEHG VCEEVERVRR SERYQTMKLF   240
TQIFGVGVKT ADRWYREGLR TLDDLREQPQ KLTQQQKAGL QHHQDLSTPV LRSDVDALQQ   300
VVEEAVGQAL PGATVTLTGG FRRGKLQGHD VDFLITHPKE GQEAGLLPRV MCRLQDQGLI   360
LYHQHQHSCC ESPTRLAQQS HMDAFERSFC IFRLPQPPGA AVGGSTRPCP SWKAVRVDLV   420
VAPVSQFPFA LLGWTGSKLF QRELRRFSRK EKGLWLNSHG LFDPEQKTFF QAASEEDIFR   480
HLGLEYLPPE QRNA                                                    494

SEQ ID NO: 4            moltype = AA  length = 401
FEATURE                 Location/Qualifiers
source                  1..401
                        mol_type = protein
                        organism = Homo sapiens
SEQUENCE: 4
TMGSSHHHHH HSSGLVPRGS HMSPSPVPGS QNVPAPAVKK ISQYACQRRT TLNNYNQLFT   60
DALDILAEND ELRENEGSCL AFMRASSVLK SLPFPITSMK DTEGIPCLGD KVKSIIEGII   120
EDGESSEAKA VLNDERYKSF KLFTSVFGVG LKTAEKWFRM GFRTLSKIQS DKSLRFTQMQ   180
KAGFLYYEDL VSCVNRPEAE AVSMLVKEAV VTFLPDALVT MTGGFRRGKM TGHDVDFLIT   240
SPEATEDEEQ QLLHKVTDFW KQQGLLLYCD ILESTFEKFK QPSRKVDALD HFQKCFLILK   300
LDHGRVHSEK SGQQEGKGWK AIRVDLVMCP YDRRAFALLG WTGSRQFERD LRRYATHERK   360
MMLDNHALYD RTKRVFLEAE SEEEIFAHLG LDYIEPWERN A                      401

SEQ ID NO: 5            moltype = DNA  length = 20
FEATURE                 Location/Qualifiers
misc_feature            1..20
                        note = t7-pro primer
source                  1..20
                        mol_type = other DNA
                        organism = synthetic construct
SEQUENCE: 5
taatacgact cactataggg                                              20

SEQ ID NO: 6            moltype = DNA  length = 19
FEATURE                 Location/Qualifiers
misc_feature            1..19
                        note = T7-ter primer
source                  1..19
                        mol_type = other DNA
                        organism = synthetic construct
SEQUENCE: 6
gctagttatt gctcagcgg                                               19

SEQ ID NO: 7            moltype = DNA  length = 18
FEATURE                 Location/Qualifiers
misc_feature            1..18
                        note = primer
source                  1..18
                        mol_type = other DNA
                        organism = synthetic construct
SEQUENCE: 7
aaaaaaaaaa aaaagggg                                                18

SEQ ID NO: 8            moltype = DNA  length = 20
```

```
FEATURE                    Location/Qualifiers
misc_feature               1..20
                           note = primer
source                     1..20
                           mol_type = other DNA
                           organism = synthetic construct
SEQUENCE: 8
tttttttttt ttaaataagg                                                    20

SEQ ID NO: 9               moltype = AA  length = 401
FEATURE                    Location/Qualifiers
REGION                     1..401
                           note = Reference TdT variant
source                     1..401
                           mol_type = protein
                           organism = synthetic construct
SEQUENCE: 9
TMGSSHHHHH HSSGLVPRGS HMSPSPVPGS QNVPAPAVKK ISQYACQRRT TLNNYNQLFT  60
DALDILAEND ELRENEGSCL AFMRASSVLK SLPFPITSMK DTEGIPCLGD KVKSIIEGII  120
EDGESSEAKA VLNDERYKSF KLFTSVFGVG LKTAEKWFRM GFRTLSKIQS DKSLRFTQMQ  180
KAGFLYYEDL VSCVNRPEAE AVSMLVKEAV VTFLPDALVT MTGGFRRGKM TGHDVDFLIT  240
SPEATEDEEQ QLLHKVTDFW KQQGLLLYCD ILESTFEKFK QPSRKVDALD HFQKCFLILK  300
LDHGRVHSEK SGQQEGKGWK AIRVDLVMCP YDRRAFALLG WTGSAQFSRD LRRYATHERK  360
MMLDNHALYD RTKRVFLEAE SEEEIFAHLG LDYIEPWERN A                     401

SEQ ID NO: 10              moltype = AA  length = 519
FEATURE                    Location/Qualifiers
source                     1..519
                           mol_type = protein
                           organism = Bos taurus
SEQUENCE: 10
MAQQRQHQRL PMDPLCTASS GPRKKRPRQV GASMASPPHD IKFQNLVLFI LEKKMGTTRR  60
NFLMELARRK GFRVENELSD SVTHIVAENN SGSEVLEWLQ VQNIRASSQL ELLDVSWLIE  120
SMGAGKPVEI TGKHQLVVRT DYSATPNPGF QKTPPLAVKK ISQYACQRRT TLNNYNHIFT  180
DAFEILAENS EFKENEVSYV TFMRAASVLK SLPFTIISMK DTEGIPCLGD KVKCIIEEII  240
EDGESSEVKA VLNDERYQSF KLFTSVFGVG LKTSEKWFRM GFRSLSKIMS DKTLKFTKMQ  300
KAGFLYYEDL VSCVTRAEAE AVGVLVKEAV WAFLPDAFVT MTGGFRRGKK IGHDVDFLIT  360
SPGSAEDEEQ LLPKVINLWE KKGLLLYYDL VESTFEKFKL PSRQVDTLDH FQKCFLILKL  420
HHQRVDSSKS NQQEGKTWKA IRVDLVMCPY ENRAFALLGW TGSRQFERDI RRYATHERKM  480
MLDNHALYDK TKRVFLKAES EEEIFAHLGL DYIEPWERN                        519

SEQ ID NO: 11              moltype = AA  length = 380
FEATURE                    Location/Qualifiers
source                     1..380
                           mol_type = protein
                           organism = Bos taurus
SEQUENCE: 11
DYSATPNPGF QKTPPLAVKK ISQYACQRKT TLNNYNHIFT DAFEILAENS EFKENEVSYV  60
TFMRAASVLK SLPFTIISMK DTEGIPCLGD KVKCIIEEII EDGESSEVKA VLNDERYQSF  120
KLFTSVFGVG LKTSEKWFRM GFRSLSKIMS DKTLKFTKMQ KAGFLYYEDL VSCVTRAEAE  180
AVGVLVKEAV WAFLPDAFVT MTGGFRRGKK IGHDVDFLIT SPGSAEDEEQ LLPKVINLWE  240
KKGLLLYYDL VESTFEKFKL PSRQVDTLDH FQKCFLILKL HHQRVDSSKS NQQEGKTWKA  300
IRVDLVMCPY ENRAFALLGW TGSRQFERDI RRYATHERKM MLDNHALYDK TKRVFLKAES  360
EEEIFAHLGL DYIEPWERNA                                             380

SEQ ID NO: 12              moltype = AA  length = 509
FEATURE                    Location/Qualifiers
source                     1..509
                           mol_type = protein
                           organism = Homo sapiens
SEQUENCE: 12
MDPPRASHLS PRKKRPRQTG ALMASSPQDI KFQDLVVFIL EKKMGTTRRA FLMELARRKG  60
FRVENELSDS VTHIVAENNS GSDVLEWLQA QKVQVSSQGE LLDVSWLIEC IRAGKPVEMT  120
GKHQLVVRRD YSDSTNPGPP KTPPIAVQKI SQYACQRRTT LNNCNQIFTD AFDILAENCE  180
FRENEDSCVT FMRAASVLKS LPFTIISMKD TEGIPCLGSK VKGIIEEIIE DGESSEVKAV  240
LNDERYQSFK LFTSVFGVGL KTSEKWFRMG FRTLSKVRSD KSLKFTRMQK AGFLYYEDLV  300
SCVTRAEAEA VSVLVKEAVW AFLPDAFVTM TGGFRRGKKG HDVDFLITS PGSTEDEEQL  360
LQKVMNLWEK KGLLLYYDLV ESTFEKLRLP SRKVDALDHF QKCFLIFKLP RQRVDSDQSS  420
WQEGKTWKAI RVDLVLCPYE RRAFALLGWT GSRQFERDLR RYATHERKMI LDNHALYDKT  480
KRIFLKAESE EEIFAHLGLD YIEPWERNA                                   509

SEQ ID NO: 13              moltype = AA  length = 380
FEATURE                    Location/Qualifiers
source                     1..380
                           mol_type = protein
                           organism = Homo sapiens
SEQUENCE: 13
DYSDSTNPGP PKTPPIAVQK ISQYACQRRT TLNNCNQIFT DAFDILAENC EFRENEDSCV  60
TFMRAASVLK SLPFTIISMK DTEGIPCLGS KVKGIIEEII EDGESSEVKA VLNDERYQSF  120
```

```
KLFTSVFGVG LKTSEKWFRM GFRTLSKVRS DKSLKFTRMQ KAGFLYYEDL VSCVTRAEAE    180
AVSVLVKEAV WAFLPDAFVT MTGGFRRGKK MGHDVDFLIT SPGSTEDEEQ LLQKVMNLWE    240
KKGLLLYYDL VESTFEKLRL PSRKVDALDH FQKCFLIFKL PRQRVDSDQS SWQEGKTWKA    300
IRVDLVLCPY ERRAFALLGW TGSRQFERDL RRYATHERKM ILDNHALYDK TKRIFLKAES    360
EEEIFAHLGL DYIEPWERNA                                               380

SEQ ID NO: 14           moltype = AA  length = 506
FEATURE                 Location/Qualifiers
source                  1..506
                        mol_type = protein
                        organism = Gallus gallus
SEQUENCE: 14
MERIRPPTVV SQRKRQKGMY SPKLSCGYEI KFNKLVIFIM QRKMGMTRRT FLMELARSKG     60
FRVESELSDS VTHIVAENNS YPEVLDWLKG QAVGDSSRFE ILDISWLTAC MEMGRPVDLE    120
KKYHLVEQAG QYPTLKTPES EVSSFTASKV SQYSCQRKTT LNNCNKKFTD AFEIMAENYE    180
FKENEIFCLE FLRAASVLKS LPFPVTRMKD IQGLPCMGDR VRDVIEEIIE EGESSRAKDV    240
LNDERYKSFK EFTSVFGVGV KTSEKWFRMG LRTVEEVKAD KTLKLSKMQR AGFLYYEDLV    300
SCVSKAEADA VSSIVKEQIT TFLPDALVTI TGGFRRGKKI GHDIDFLITS PGQREDDELL    360
HKGLLLYCDI IESTFVKEQI PSRHVDAMDH FQKCFAILKL YQPRVDNSSY NMSKKCDMAE    420
VKDWKAIRVD LVITPFEQYA YALLGWTGSR QFGRDLRRYA THERKMMLDN HALYDKRKRV    480
FLKAGSEEEI FAHLGLDYVE PWERNA                                        506

SEQ ID NO: 15           moltype = AA  length = 376
FEATURE                 Location/Qualifiers
source                  1..376
                        mol_type = protein
                        organism = Gallus gallus
SEQUENCE: 15
QYPTLKTPES EVSSFTASKV SQYSCQRKTT LNNCNKKFTD AFEIMAENYE FKENEIFCLE     60
FLRAASVLKS LPFPVTRMKD IQGLPCMGDR VRDVIEEIIE EGESSRAKDV LNDERYKSFK    120
EFTSVFGVGV KTSEKWFRMG LRTVEEVKAD KTLKLSKMQR AGFLYYEDLV SCVSKAEADA    180
VSSIVKNTVC TFLPDALVTI TGGFRRGKKI GHDIDFLITS PGQREDDELL HKGLLLYCDI    240
IESTFVKEQI PSRHVDAMDH FQKCFAILKL YQPRVDNSSY NMSKKCDMAE VKDWKAIRVD    300
LVITPFEQYA YALLGWTGSR QFGRDLRRYA THERKMMLDN HALYDKRKRV FLKAGSEEEI    360
FAHLGLDYVE PWERNA                                                   376

SEQ ID NO: 16           moltype = AA  length = 518
FEATURE                 Location/Qualifiers
source                  1..518
                        mol_type = protein
                        organism = Monodelphis domestica
SEQUENCE: 16
MHRIRTIDSD FGKKRQKKMD NHISSMIYEI KFHEFVLFIL EKKMGATRRT FLTDLARKKG     60
FRVENELSNS VTHIVAENNS GSDVLAWLKT HKMEKTTQFE LLDISWLIEC MKVGKPVDTK    120
GKYQLMESRV DSANPDPTAG TLNILPPTTK TISQYACQRR TTINNHNQRF TDAFEILAKN    180
YEFKENDDTC LTFMRAISVL KCLPFEVVSL KDTEGLPWIG DEVKGIMEEI IEDGESLEVQ    240
AVLNDERYQS FKLFTSVFGV GLKTADKWYR MGFRTLNKIR SDKTLKLTKM QKAGLCYYED    300
LIDCVSKAEA DAVSLLVQDA VWTFLPDALV TITGGFRRGK EFGHDVDFLI TSPGAEKEQE    360
DQLLQKVTNL WKKQGLLLYC DLIESTFEDL KLPSRKIDAL DHFQKCFLIL KLYHHKEDKR    420
KWEMPTGSNE SEAKSWKAIR VDLVVCPYDR YAFALLGWSG SRQFERDLRR YATHEKKMML    480
DNHALYDKTK KIFLKAKSEE EIFAHLGLEY IQPSERNA                            518

SEQ ID NO: 17           moltype = AA  length = 387
FEATURE                 Location/Qualifiers
source                  1..387
                        mol_type = protein
                        organism = Monodelphis domestica
SEQUENCE: 17
SANPDPTAGT LNILPPTTKT ISQYACQRRT TINNHNQRFT DAFEILAKNY EFKENDDTCL     60
TFMRAISVLK CLPFEVVSLK DTEGLPWIGD EVKGIMEEII EDGESLEVQA VLNDERYQSF    120
KLFTSVFGVG LKTADKWYRM GFRTLNKIRS DKTLKLTKMQ KAGLCYYEDL IDCVSKAEAD    180
AVSLLVQDAV WTFLPDALVT ITGGFRRGKE FGHDVDFLIT SPGAEKEQED QLLQKVTNLW    240
KKQGLLLYCD LIESTFEDLK LPSRKIDALD HFQKCFLILK LYHHKEDKRK WEMPTGSNES    300
EAKSWKAIRV DLVVCPYDRY AFALLGWSGS RQFERDLRRY ATHEKKMMLD NHALYDKTKK    360
IFLKAKSEEE IFAHLGLEYI QPSERNA                                       387

SEQ ID NO: 18           moltype = AA  length = 512
FEATURE                 Location/Qualifiers
source                  1..512
                        mol_type = protein
                        organism = Elephantulus edwardii
SEQUENCE: 18
MDPLQMACTG PRKKRARQMD TSMGSTQDIK FQDLVLFILE KKMGTTRRAF LMELARRKGF     60
RVENELSDSV THIVAENNSG SDVLEWLQVQ KIKASSQLEL LDVSWLIECM GAGKLVEITG    120
KHQLVSIMVR GDCPASHDSS PQKTESAAVQ KISQYACQRR TTLNNHNHIF TDAFEILAEN    180
CEFRENEGSY VTYMRAASVL KSLPFSIISM KDTEGIPCLA DKVKCVIEEI IEDGESSEVK    240
AVLNDERYKS FKLFTSVFGV GLKTAEKWFR LGFRTLSGIM NDKTLKLTHM QKAGFLYYED    300
LVSCVTRAEA EAVGVLVKEA VWAFLPDAIV TMTGGFRRGK VGHDVDFLIT SPEATEEQE     360
QQLLHKVITF WEKEGLLLYC DLYESTFEKL KMPSRKVDAL DHFQKCFLIL KLHRECVDDG    420
```

```
TSSQLQGKTW KAIRVDLVVC PYECRAFALL GWTGSPQFER DLRRYATHER KMMLDNHALY   480
DKTKRKFLSA DSEEDIFAHL GLDYIEPWER NA                                512

SEQ ID NO: 19           moltype = AA  length = 381
FEATURE                 Location/Qualifiers
source                  1..381
                        mol_type = protein
                        organism = Elephantulus edwardii
SEQUENCE: 19
DCPASHDSSP QKTESAAVQK ISQYACQRRT TLNNHNHIFT DAFEILAENC EFRENEGSYV    60
TYMRAASVLK SLPFSIISMK DTEGIPCLAD KVKCVIEEII EDGESSEVKA VLNDERYKSF   120
KLFTSVFGVG LKTAEKWFRL GFRTLSGIMN DKTLKLTHMQ KAGFLYYEDL VSCVTRAEAE   180
AVGVLVKEAV WAFLPDAIVT MTGGFRRGKK VGHDVDFLIT SPEATEEQEQ QLLHKVITFW   240
EKEGLLLYCD LYESTFEKLK MPSRKVDALD HFQKCFLILK LHRECVDDGT SSQLQGKTWK   300
AIRVDLVVCP YECRAFALLG WTGSPQFERD LRRYATHERK MMLDNHALYD KTKRKFLSAD   360
SEEDIFAHLG LDYIEPWERN A                                            381

SEQ ID NO: 20           moltype = AA  length = 506
FEATURE                 Location/Qualifiers
REGION                  1..506
                        note = Python bivittatus
source                  1..506
                        mol_type = protein
                        organism = synthetic construct
SEQUENCE: 20
MNKMKTSDFS PMRKRQKRMQ IAAPLSSYKI EFKDIIIFIV ERKMGMTRRM FLMDLARRKG    60
FRVENELSDL VTHVVAENNS CSEILKWLQK HNVEDSSRFR ILDIRWLTAC MEVGRPVDSE   120
KYQLPEDEDR SVTSDLDRDS ISEYACQRRT TLKNYNQKFT DAFEILAENY EFNENKGFCT   180
AFRRAASVLK CLPFTIVQVH DIEGVPWMGK QVKGIIEDII EEGESSKVKA VLDNENYRSV   240
KLFTSVFGVG LKTSDKWYRM GLRTLEEVKR DKNLKLTRMQ KAGFLHYDDL TSCVSKAEAD   300
AASLIVQDVV WKIVPNAIVT IAGGFRRGKG TGHDVDFLIT VPGSKQEEEE LLHTVIDIWK   360
KQELLLYYDL IESTFEDTKL PSRKVDALDH FQKCFAILKV HKEREDKGNS IRSKAFSEEE   420
IKDWKAIRVD LVVVPFEQYA FALLGWTGST QFERDLRRYA THEKKMMLDN HALYDKTKKI   480
FLNAASEEEI FAHLGLDYLE PWERNA                                       506

SEQ ID NO: 21           moltype = AA  length = 387
FEATURE                 Location/Qualifiers
REGION                  1..387
                        note = Python bivittatus
source                  1..387
                        mol_type = protein
                        organism = synthetic construct
SEQUENCE: 21
EKYQLPEDED RSVTSDLDRD SISEYACQRR TTLKNYNQKF TDAFEILAEN YEFNENKGFC    60
TAFRRAASVL KCLPFTIVQV HDIEGVPWMG KQVKGIIEDI IEEGESSKVK AVLDNENYRS   120
VKLFTSVFGV GLKTSDKWYR MGLRTLEEVK RDKNLKLTRM QKAGFLHYDD LTSCVSKAEA   180
DAASLIVQDV VWKIVPNAIV TIAGGFRRGK QTGHDVDFLI TVPGSKQEEE ELLHTVIDIW   240
KKQELLLYYD LIESTFEDTK LPSRKVDALD HFQKCFAILK VHKEREDKGN SIRSKAFSEE   300
EIKDWKAIRV DLVVVPFEQY AFALLGWTGS TQFERDLRRY ATHEKKMMLD NHALYDKTKK   360
IFLNAASEEE IFAHLGLDYL EPWERNA                                      387

SEQ ID NO: 22           moltype = AA  length = 490
FEATURE                 Location/Qualifiers
source                  1..490
                        mol_type = protein
                        organism = Canis lupus
SEQUENCE: 22
MGAEAGTWRD TGGKFLLLAT EPERKFRASD ACCQGPSPAG QALEETGACD SITHIVAENN    60
SGSDVLEWLQ VQNIKASSQL ELLDISWLIE SMGAGKPVEM TGKHQLMRRD YTASPNPELQ   120
KTLPVAVKKI SQYACQRRTT LNNYNNVFTD AFEVLAENYE FRENEVFSLT FMRAASVLKS   180
LPFTIISMKD TEGIPCLGDQ VKCIIEEIIE DGESSKVKAV LNDERYQSFK LFTSVFGVGL   240
KTSEKWFRMG FRTLSKIKSD KSLKFTPMQK AGFLYYEDLV SCVTRAEAEA VGVLVKEAVG   300
AFLPDAFVTM TGGFRRGKKM GHDVDFLITS PGSTDEDEEQ LLPKVINLWE RKGLLLYCDL   360
VESTFEKLKL PSRKVDALDH FQKCFLILKL HHQRVDGGKC SQQEGKTWKA IRVDLVMCPY   420
ERRAFALLGW TGSRQFERDL RRYASHERKM ILDNHALYDK TKKIFLKAES EEEIFAHLGL   480
DYIEPWERNA                                                         490

SEQ ID NO: 23           moltype = AA  length = 381
FEATURE                 Location/Qualifiers
source                  1..381
                        mol_type = protein
                        organism = Canis lupus
SEQUENCE: 23
DYTASPNPEL QKTLPVAVKK ISQYACQRRT TLNNYNNVFT DAFEVLAENY EFRENEVFSL    60
TFMRAASVLK SLPFTIISMK DTEGIPCLGD QVKCIIEEII EDGESSEVKA VLNDERYQSF   120
KLFTSVFGVG LKTSEKWFRM GFRTLSKIKS DKSLKFTPMQ KAGFLYYEDL VSCVTRAEAE   180
AVGVLVKEAV GAFLPDAFVT MTGGFRRGKK MGHDVDFLIT SPGSTDEDEE QLLPKVINLW   240
ERKGLLLYCD LVESTFEKLK LPSRKVDALD HFQKCFLILK LHHQRVDGGK CSQQEGKTWK   300
AIRVDLVMCP YERRAFALLG WTGSRQFERD LRRYASHERK MILDNHALYD KTKKIFLKAE   360
```

```
SEEEIFAHLG LDYIEPWERN A                                                381

SEQ ID NO: 24           moltype = AA  length = 512
FEATURE                 Location/Qualifiers
REGION                  1..512
                        note = Condylura cristata
source                  1..512
                        mol_type = protein
                        organism = synthetic construct
SEQUENCE: 24
MDPLQMACTG PRKKRARQMD TSMGSTQDIK FQDLVLFILE KKMGTTRRAF LMELARRKGF    60
RVENELSDSV THIVAENNSG SDVLEWLQVQ KIKASSQLEL LDVSWLIECM GAGKLVEITG   120
KHQLVSIMVR GDCPASHDSS PQKTESAAVQ KISQYACQRR TTLNNHNHIF TDAFEILAEN   180
CEFRENEGSY VTYMRAASVL KSLPFSIISM KDTEGIPCLA DKVKCVIEEI IEDGESSEVK   240
AVLNDERYKS FKLFTSVFGV GLKTAEKWFR LGFRTLSGIM NDKTLKLTHM QKAGFLYYED   300
LVSCVTRAEA EAVGVLVKEA VWAFLPDAIV TMTGGFRRGK KVGHDVDFLI TSPEATEEQE   360
QQLLHKVITF WEKEGLLLYC DLYESTFEKL KMPSRKVDAL DHFQKCFLIL KLHRECVDDG   420
TSSQLQGKTW KAIRVDLVVC PYECRAFALL GWTGSPQFER DLRRYATHER KMMLDNHALY   480
DKTKRKFLSA DSEEDIFAHL GLDYIEPWER NA                                 512

SEQ ID NO: 25           moltype = AA  length = 382
FEATURE                 Location/Qualifiers
REGION                  1..382
                        note = Condylura cristata
source                  1..382
                        mol_type = protein
                        organism = synthetic construct
SEQUENCE: 25
GDCPASHDSS PQKTESAAVQ KISQYACQRR TTLNNHNHIF TDAFEILAEN CEFRENEGSY    60
VTYMRAASVL KSLPFSIISM KDTEGIPCLA DKVKCVIEEI IEDGESSEVK AVLNDERYKS   120
FKLFTSVFGV GLKTAEKWFR LGFRTLSGIM NDKTLKLTHM QKAGFLYYED LVSCVTRAEA   180
EAVGVLVKEA VWAFLPDAIV TMTGGFRRGK KVGHDVDFLI TSPEATEEQE QQLLHKVITF   240
WEKEGLLLYC DLYESTFEKL KMPSRKVDAL DHFQKCFLIL KLHRECVDDG TSSQLQGKTW   300
KAIRVDLVVC PYECRAFALL GWTGSPQFER DLRRYATHER KMMLDNHALY DKTKRKFLSA   360
DSEEDIFAHL GLDYIEPWER NA                                            382

SEQ ID NO: 26           moltype = AA  length = 508
FEATURE                 Location/Qualifiers
source                  1..508
                        mol_type = protein
                        organism = Ochotona princeps
SEQUENCE: 26
MDSLQTGHLG PRKKRSRQTD AARTSIPQEV KFQDLVLFIL EKKMGSTRRA FLMELARSKG    60
FRVENELSDS VTHIVAENNS GSDVLEWLQV QKLKDSSQLE LLDVSWLIEC MRAGKPVATT   120
GKHQLVMREE YSANPSPGPQ ATPAVYKISQ YACQRRTTLN NHNHIFTDAF EILAENYEFK   180
ENEGCYVTYM RAASVLKSLP FTIVSMKDTE GIPCLEDKVK SIMEEIIEEG ESSEVKAVLS   240
DERYQCFKLF TSVFGVGLKT SEKWFRMGFR SLSNIRLDKS LKFTQMQKAG FRYYEDIVSC   300
VTRAEAEAVD VLVNEAVRAF LPDAFITMTG GFRRGKKIGH DVDFLITSPE LTEEDEQQLL   360
HKVMNLWEKK GLLLYHDLVE STFEKLKQPS RKVDALDHFQ KCFLIFKLYH ERVGGDRCRQ   420
PEGKDWKAIR VDLVMCPYEC HAFALLGWTG SRQFERDLRR YASHERKMIL DNHALYDKTK   480
RVFLQAENEE EIFAHLGLDY IEPWERNA                                      508

SEQ ID NO: 27           moltype = AA  length = 379
FEATURE                 Location/Qualifiers
source                  1..379
                        mol_type = protein
                        organism = Ochotona princeps
SEQUENCE: 27
EYSANPSPGP QATPAVYKIS QYACQRRTTL NNHNHIFTDA FEILAENYEF KENEGCYVTY    60
MRAASVLKSL PFTIVSMKDT EGIPCLEDKV KSIMEEIIEE GESSEVKAVL SDERYQCFKL   120
FTSVFGVGLK TSEKWFRMGF RSLSNIRLDK SLKFTQMQKA GFRYYEDIVS CVTRAEAEAV   180
DVLVNEAVRA FLPDAFITMT GGFRRGKKIG HDVDFLITSP ELTEEDEQQL LHKVMNLWEK   240
KGLLLYHDLV ESTFEKLKQP SRKVDALDHF QKCFLIFKLY HERVGGDRCR QPEGKDWKAI   300
RVDLVMCPYE CHAFALLGWT GSRQFERDLR RYASHERKMI LDNHALYDKT KRVFLQAENE   360
EEIFAHLGLD YIEPWERNA                                                379

SEQ ID NO: 28           moltype = AA  length = 516
FEATURE                 Location/Qualifiers
source                  1..516
                        mol_type = protein
                        organism = Erinaceus europaeus
SEQUENCE: 28
MDALPVVHSS PRKKRSRLMG ASVAYPPYDI KFHNLVLFIL EKKMGSSRRA FLMELARRKG    60
FRVEDELSDS ITHIVAENNT GSEVLEWLQV QDIKISSQLE LLDVSWLVEC MRAGNPVVIT   120
GKHQLVSYTV KSDASFGSNP GSQNTPPLAI KKISQYACQR RTSLNNCNHI FTDALDILAE   180
NHEFRENEVS CVAFMRAASV LKSLPFTIIS MKDTKGIPCL GDKAKCVIEE IIEDGESSEV   240
KAILNDERYQ SFKLFTSVFG VGLKTSEKWF RMGFRTLNKI MSDKTLKLTR MQKAGFLYYE   300
DLVSCVKAEA ADAVSVLVQE AVWAFLPDAM VTMTGGFRRG KKLGHDVDFL ITSPGATEEE   360
EQQLLPKVIN FWERKGLLLY HDLVESTFEK LKLPSRKVDA LDHFQKCFLI LKLHLQHVNG   420
```

```
VGNSKTGQQE GKNWKAIRVD LVMCPYERRA FALLGWTGSR QFERDLRRFA THERKMMLDN    480
HALYDKTKRI FLKAESEEEI FAHLGLDYID PWERNA                              516

SEQ ID NO: 29           moltype = AA  length = 384
FEATURE                 Location/Qualifiers
source                  1..384
                        mol_type = protein
                        organism = Erinaceus europaeus
SEQUENCE: 29
DASFGSNPGS QNTPPLAIKK ISQYACQRRT SLNNCNHIFT DALDILAENH EFRENEVSCV    60
AFMRAASVLK SLPFTIISMK DTKGIPCLGD KAKCVIEEII EDGESSEVKA ILNDERYQSF    120
KLFTSVFGVG LKTSEKWFRM GFRTLNKIMS DKTLKLTRMQ KAGFLYYEDL VSCVAKAEAD    180
AVSVLVQEAV WAFLPDAMVT MTGGFRRGKK LGHDVDFLIT SPGATEEEEQ QLLPKVINFW    240
ERKGLLLYHD LVESTFEKLK LPSRKVDALD HFQKCFLILK LHLQHVNGVG NSKTGQQEGK    300
NWKAIRVDLV MCPYERRAFA LLGWTGSRQF ERDLRRFATH ERKMMLDNHA LYDKTKRIFL    360
KAESEEEIFA HLGLDYIDPW ERNA                                           384

SEQ ID NO: 30           moltype = AA  length = 510
FEATURE                 Location/Qualifiers
REGION                  1..510
                        note = Tupaia chinensis
source                  1..510
                        mol_type = protein
                        organism = synthetic construct
SEQUENCE: 30
MDLLRMAPLS PRKKRPRQMG SSMASAPHDI KFQGVVLYIL EKKMGTTRRA FLMELARRKG    60
FRVENELSMS LSHQVWDXNC GXDVREWLQV QKVKASSQPE LLDVSWLVEC MRAGKPVEAT    120
GKHQLLVKSD HSTSPSPGPQ KTPALAVQKI SQYACQRRTT LNNCNRVFTD AFETLAENYE    180
FRENEDSSVI FLRAASVLRS LPFTITSMRD TEGLPCLGDK VKCVIEEIIE DGESSEVNAV    240
LNDERYKSFK LFTSVFGVGL KTSEKWFRMG FRTLSRVRSD KSLHLTRMQQ AGFLYYEDLA    300
SCVTRAEAEA VGVLVKEAVG AFLPDALVTI TGGFRRGKKT GHDVDFLITS PGSTEEKEEE    360
LLQKVLNLWE KKGLLLYYDL VESTFEKLKT PSRKVDALDH FPKCFLILKL HHQRVDGDKP    420
SQQEGKSWKA IRVDLVMCPY ERHAFALLGW TGSRQFERDL RRYATHERKM MLDNHALYDK    480
TKRVFLKAES EEDIFAHLGL DYIEPWERNA                                     510

SEQ ID NO: 31           moltype = AA  length = 381
FEATURE                 Location/Qualifiers
REGION                  1..381
                        note = Tupaia chinensis
source                  1..381
                        mol_type = protein
                        organism = synthetic construct
SEQUENCE: 31
DHSTSPSPGP QKTPALAVQK ISQYACQRRT TLNNCNRVFT DAFETLAENY EFRENEDSSV    60
IFLRAASVLR SLPFTITSMR DTEGLPCLGD KVKCVIEEII EDGESSEVNA VLNDERYKSF    120
KLFTSVFGVG LKTSEKWFRM GFRTLSRVRS DKSLHLTRMQ QAGFLYYEDL ASCVTRAEAE    180
AVGVLVKEAV GAFLPDALVT ITGGFRRGKK TGHDVDFLIS SPGSTEEKEE ELLQKVLNLW    240
EKKGLLLYYD LVESTFEKLK TPSRKVDALD HFPKCFLILK LHHQRVDGDK PSQQEGKSWK    300
AIRVDLVMCP YERHAFALLG WTGSRQFERD LRRYATHERK MMLDNHALYD KTKRVFLKAE    360
SEEDIFAHLG LDYIEPWERN A                                              381

SEQ ID NO: 32           moltype = AA  length = 525
FEATURE                 Location/Qualifiers
source                  1..525
                        mol_type = protein
                        organism = Ornithorhynchus anatinus
SEQUENCE: 32
MSFAMFPAKK EHLKKRRRM NGCISPTLYE IKFNEFVLFI LEKKMGTTRR AFLMELARRK    60
GFRVESELSE SVTHIVAENN SCSDVLEWLA VQNVGDSSVF ELLDISWLTE CMKVGKPVEA    120
IGKHQLMRGN CLTNSAPINC MTEPSLATK QVSQYACERR TTLNNCNQKF TDAFEILAKD    180
FEFRENEGIC LAFMRAISVL KCLPFTIVRM KDIEGVPWLG DQVKSIIEEI IEDGESSSVK    240
AVLNDERYRS FQLFNSVFEV GLTDNGENGI ARGFQTLNEV ITDENISLTK TTLSTSLWNY    300
LPGFLYYEDL VSCVAKEEAD AVYLIVKEAV RAFLPEALVT LTGGFRRGKK IGHDVDFLIS    360
DPESGQDEQL LPNIIKLWEK QELLLYYDLV ESTFEKTKIP SRKVDAMDHF QKCFLILKLH    420
HQKVDSGRYK PPPESKNHEA KNWKAIRVDL VMCPFEQYAY ALLGWTGSRQ FERDLRRYAT    480
HEKKMMLDNH ALYDKTKKIF LKAESEEDIF THLGLDYIEP WERNA                    525

SEQ ID NO: 33           moltype = AA  length = 394
FEATURE                 Location/Qualifiers
source                  1..394
                        mol_type = protein
                        organism = Ornithorhynchus anatinus
SEQUENCE: 33
LTNSAPINCM TEPSLATKQ VSQYACERRT TLNNCNQKFT DAFEILAKDF EFRENEGICL    60
AFMRAISVLK CLPFTIVRMK DIEGVPWLGD QVKSIIEEII EDGESSSVKA VLNDERYRSF    120
QLFNSVFEVG LTDNGENGIA RGFQTLNEVI TDENISLTKT TLSTSLWNYL PGFLYYEDLV    180
SCVAKEEADA VYLIVKEAVR AFLPEALVTL TGGFRRGKKI GHDVDFLISD PESGQDEQLL    240
PNIIKLWEKQ ELLLYYDLVE STFEKTKIPS RKVDAMDHFQ KCFLILKLHH QKVDSGRYKP    300
PPESKNHEAK NWKAIRVDLV MCPFEQYAYA LLGWTGSRQF ERDLRRYATH EKKMMLDNHA    360
```

```
LYDKTKKIFL KAESEEDIFT HLGLDYIEPW ERNA                                  394

SEQ ID NO: 34           moltype = AA  length = 479
FEATURE                 Location/Qualifiers
source                  1..479
                        mol_type = protein
                        organism = Jaculus jaculus
SEQUENCE: 34
MDPEQAAHWS PRKKRPRQRS ASVASAPHDI RFQDLVLFIL EKKMGSTRRA FLMELARRKG       60
FRVENELSDS VTHIVAENNS GSDVMKWLQG QNIQASSELE LLDVSWLIEC MGAGKPVEMT      120
GRHQLVKQTF CLPGFILQDA FDILAENCEF RENEASCVEF MRAASVLKSL PFPIISVKDT      180
EGIPWLGGKV KCVIEEIIED GESSEVKALL NDERYKSFKL FTSVFGVGLK TAERWFRMGF      240
RTLSTVKLDK SLTFTRMQKA GFLHYEDLVS CVTRAEAEAV SVLVQQAVVA FLPDALVSMT      300
GGFRRGKKIG HDVDFLITSP EATEEEQQL LHKVTNFWEQ KGLLLYCDHV ESTFEKCKLP       360
SRKVDALDHF QKCFLILKLY RERVDSVKSS QQEGKGWKAI RVDLVMCPYE CRAFALLGWT      420
GSRQFERDLR RYATHERKMR LDNHALYDKT KRVFLKAESE EEIFAHLGLE YIEPLERNA       479

SEQ ID NO: 35           moltype = AA  length = 384
FEATURE                 Location/Qualifiers
source                  1..384
                        mol_type = protein
                        organism = Jaculus jaculus
SEQUENCE: 35
SSELELLDVS WLIECMGAGK PVEMTGRHQL VKQTFCLPGF ILQDAFDILA ENCEFRENEA       60
SCVEFMRAAS VLKSLPFPII SVKDTEGIPW LGGKVKCVIE EIIEDGESSE VKALLNDERY      120
KSFKLFTSVF GVGLKTAERW FRMGFRTLST VKLDKSLTFT RMQKAGFLHY EDLVSCVTRA      180
EAEAVSVLVQ QAVVAFLPDA LVSMTGGFRR GKKIGHDVDF LITSPEATEE EEQQLLHKVT      240
NFWEQKGLLL YCDHVESTFE KCKLPSRKVD ALDHFQKCFL ILKLYRERVD SVKSSQQEGK      300
GWKAIRVDLV MCPYECRAFA LLGWTGSRQF ERDLRRYATH ERKMRLDNHA LYDKTKRVFL      360
KAESEEEIFA HLGLEYIEPL ERNA                                            384
```

VARIANTS OF TERMINAL DEOXYNUCLEOTIDYL TRANSFERASE AND USES THEREOF

CROSS-REFERENCE TO RELATED APPLICATIONS

This application is a continuation of U.S. patent application Ser. No. 17/544,647, filed Dec. 7, 2021, which is a continuation of U.S. patent application Ser. No. 16/925,785, filed Jul. 10, 2020, issued as U.S. Pat. No. 11,208,637, which is a continuation of U.S. patent application Ser. No. 16/423,972, filed May 28, 2019, issued as U.S. Pat. No. 10,752,887, which is a continuation-in-part of U.S. patent application Ser. No. 16/242,904, filed Jan. 8, 2019, issued as U.S. Pat. No. 10,435,676, which claims priority to European Patent Application No. 18305006.1, filed Jan. 8, 2018, which applications are incorporated by reference herein in their entirety.

SEQUENCE LISTING

The content of the electronic sequence listing (283182001003seqlist.xml; Size: 48,998 bytes; and Date of Creation: Mar. 14, 2024) is herein incorporated by reference in its entirety.

FIELD OF THE INVENTION

The invention relates to variants of Terminal deoxynucleotidyl Transferase (TdT) and uses thereof for the enzymatic synthesis of nucleic acid sequences without template. More particularly, the present invention relates to such variants suitable to incorporate modified nucleotides, for the synthesis of nucleic acid molecules with determined or controlled sequences.

BACKGROUND

Methods for de novo chemical synthesis of nucleic acids based on solid-phase phosphoramidite chemistry have been largely used and refined over the past 40 years. The technique consists of a four-step chain elongation cycle that adds one base per cycle onto a growing oligonucleotide chain attached to a solid support matrix. Although it has been the method of choice to synthesize nucleic acids during the past decades, this technology has some notable limitations: It requires the use of multiple solvents and reagents, and due to limitations in chemical reaction efficiency, the length of synthetic oligonucleotides typically do not exceed 150-200 bases. Moreover, these short fragments need to be further assembled to provide the desired DNA sequence.

One alternative to chemical synthesis consists in using template independent DNA polymerases that will add reversible terminator modified nucleotides to a growing single stranded chain of nucleic acids. This allows the addition of one type of nucleotide per cycle in a controlled fashion.

Some native enzymes are able to act on natural nucleotides in the absence of template and so can catalyze the synthesis of nucleic acids in an uncontrolled fashion. However, they are particularly inefficient to incorporate modified nucleotides and more particularly reversible terminator modified nucleotides. Efforts have been made to develop new DNA polymerases able to act on modified nucleotides but the resulting enzymes are not fully satisfactory in terms of performances for the synthesis of any type of nucleic acids.

So far, only few DNA polymerases that can act efficiently on single strand DNA (without the use of template) have been identified. The most characterized polymerase having such template-independent activity is the Terminal deoxynucleotidyl Transferase (TdT). TdT enzymes have been extensively used to modify single stranded DNA for various types of applications including biotechnology, biomedical research and synthetic biology. However, native TdT is poorly able to use modified nucleotides.

Several attempts to develop modified TdT with acceptable performance for the incorporation of modified nucleotides have been carried over. However, the performances of the incorporation of such modified nucleotides is still a limiting factor. Incorporation efficiency is the key parameter driving the overall purity and yield of synthesis. These two characteristics of the synthesis process have a significant impact of quality, turnaround time and cost of nucleic acid products.

There is therefore a need to develop improved TdT capable to use modified nucleotides in the absence of template, for developing efficient and cost-effective methods for the nucleic acid synthesis.

SUMMARY OF THE INVENTION

By working on TdT for de novo synthesis of polynucleotides with controlled sequence and without the use of a template, the inventors have discovered that some targeted amino acid residues of the catalytic domain of the TdT may be specifically modified to improve the ability of such modified TdT for synthesizing polynucleotides. More particularly, the inventors have developed modified TdTs with targeted amino acid substitution(s) that lead to improve the enzymatic synthesis of polynucleotides and to reduce the overall cost of synthesizing polynucleotides. In some embodiments, each of the modified TdTs presents one or more targeted amino acids substitution as compared to wild-type TdTs (such as SEQ ID NOs:1, 10, 12, 14, 16, 18, 20, 22, 24, 26, 28, 30, 32 or 34) and N-terminal truncated versions thereof that comprise a TdT catalytic domain. In some embodiments, each of the modified TdTs of the invention possesses an amino acid sequence having a specified percent sequence identity with a catalytic domain of a TdT (such as SEQ ID NOs:2, 11, 13, 15, 17, 19, 21, 23, 25, 27, 29, 31, 33 or 35) and having one or more specified amino acid substitution(s). The template-independent polymerases of the invention allow the enzymatic synthesis of polynucleotides at a faster rate, with less expense and higher quality.

It is therefore an object of the invention to provide variants of Terminal deoxynucleotidyl Transferase (TdT) which (i) comprise an amino acid sequence of a TdT catalytic domain or of a percent sequence identity of a TdT catalytic domain, such as set forth in SEQ ID NOs 2, 11, 13, 15, 17, 19, 21, 23, 25, 27, 29, 31, 33 or 35, with at least an amino acid substitution at position corresponding to residue C302 (with respect to the amino acid numbering of SEQ ID NO: 1), or functionally equivalent residue, (ii) is capable of synthesizing a nucleic acid fragment without template and (iii) is capable of incorporating a modified nucleotide, such as a 3'-O-modified nucleotide onto a free 3'-hydroxyl of a nucleic fragment.

More particularly, it is an object of the present invention to provide terminal deoxynucleotidyl transferase (TdT) variants comprising an amino acid sequence at least 90% identical to SEQ ID NO: 2, 11, 13, 15, 17, 19, 21, 23, 25, 27, 29, 31, 33 or 35 with a substitution at position corresponding to residue C173 with respect to SEQ ID NOs 2, 11, 13, 17, 19, 21, 29 or 31, or at position corresponding to residue C172 with respect to SEQ ID NO: 15, or at position corresponding to residue C178 with respect to SEQ ID NO: 23, or at position corresponding to residue C174 with respect to SEQ ID NO: 25, or at position corresponding to residue C171 with respect to SEQ ID NO: 27, or at position corresponding to residue C182 with respect to SEQ ID NO: 33, or at position corresponding to residue C176 with respect to SEQ ID NO: 35, wherein the TdT variant (i) is capable of synthesizing a nucleic acid fragment without a template and (ii) is capable of incorporating a 3'-O-modified nucleotide onto a free 3'-hydroxyl of a nucleic acid fragment. In some embodiments, the above percent identity value is at least 95 percent identity with the indicated SEQ ID NOs; in some embodiments, the above percent identity value is at least 97 percent identity; in some embodiments, the above percent identity value is at least 98 percent identity; in some embodiments, the above percent identity value is at least 99 percent identity.

Advantageously, in regard to (iii), such 3'-O-modified nucleotide may comprise a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In a particular embodiment, the substitution is selected from:
C302G/R/P/A/V/S/N/Q/D with respect to SEQ ID NO:1; or C173G/R/P/A/V/S/N/Q/D with respect to SEQ ID NO:2; or
C313G/R/P/A/V/S/N/Q/D with respect to SEQ ID NO: 10; or C173G/R/P/A/V/S/N/Q/D with respect to SEQ ID NO:11; or C302G/R/P/A/V/S/N/Q/D with respect to SEQ ID NO:12; or
C173G/R/P/A/V/S/N/Q/D with respect to SEQ ID NO: 13; or C302G/R/P/A/V/S/N/Q/D with respect to SEQ ID NO:14; or C172G/R/P/A/V/S/N/Q/D with respect to SEQ ID NO:15; or
C304G/R/P/A/V/S/N/Q/D with respect to SEQ ID NO:16; or C173G/R/P/A/V/S/N/Q/D with respect to SEQ ID NO:17; or C304G/R/P/A/V/S/N/Q/D with respect to SEQ ID NO:18; or
C173G/R/P/A/V/S/N/Q/D with respect to SEQ ID NO:19; or C293G/R/P/A/V/S/N/Q/D with respect to SEQ ID NO:20; or C174G/R/P/A/V/S/N/Q/D with respect to SEQ ID NO:21; or
C282G/R/P/A/V/S/N/Q/D with respect to SEQ ID NO:22; or C173G/R/P/A/V/S/N/Q/D with respect to SEQ ID NO:23; or C304G/R/P/A/V/S/N/Q/D with respect to SEQ ID NO:24; or
C174G/R/P/A/V/S/N/Q/D with respect to SEQ ID NO:25; or C300G/R/P/A/V/S/N/Q/D with respect to SEQ ID NO:26; or C171G/R/P/A/V/S/N/Q/D with respect to SEQ ID NO:27; or
C305G/R/P/A/V/S/N/Q/D with respect to SEQ ID NO:28; or C173G/R/P/A/V/S/N/Q/D with respect to SEQ ID NO:29; or C302G/R/P/A/V/S/N/Q/D with respect to SEQ ID NO:30; or
C173G/R/P/A/V/S/N/Q/D with respect to SEQ ID NO:31; or C313G/R/P/A/V/S/N/Q/D with respect to SEQ ID NO:32; or C182G/R/P/A/V/S/N/Q/D with respect to SEQ ID NO:33; or
C271G/R/P/A/V/S/N/Q/D with respect to SEQ ID NO:34; or C176G/R/P/A/V/S/N/Q/D with respect to SEQ ID NO:35.

In a further embodiment, the substitution is selected from:
C302G/R with respect to SEQ ID NO:1; or C302G/R with respect to SEQ ID NO:1; or C173G/R with respect to SEQ ID NO:2; or C302G/R with respect to SEQ ID NO:4; or C302G/R with respect to SEQ ID NO:9; or C313G/R with respect to SEQ ID NO:10; or C173G/R with respect to SEQ ID NO:11; or C302G/R with respect to SEQ ID NO:12; or C173G/R with respect to SEQ ID NO:13; or C302G/R with respect to SEQ ID NO:14; or C172G/R with respect to SEQ ID NO: 15; or C304G/R with respect to SEQ ID NO: 16; or C173G/R with respect to SEQ ID NO:17; or C304G/R with respect to SEQ ID NO:18; or C173G/R with respect to SEQ ID NO:19; or C293G/R with respect to SEQ ID NO:20; or C173G/R with respect to SEQ ID NO:21; or C282G/R with respect to SEQ ID NO:22; or C173G/R with respect to SEQ ID NO:23; or C304G/R with respect to SEQ ID NO:24; or C174G/R with respect to SEQ ID NO:25; or C300G/R with respect to SEQ ID NO:26; or C171G/R with respect to SEQ ID NO:27; or C305G/R with respect to SEQ ID NO:28; or C173G/R with respect to SEQ ID NO:29; or C302G/R with respect to SEQ ID NO:30; or C173G/R with respect to SEQ ID NO:31; or C313G/R with respect to SEQ ID NO:32; or C182G/R with respect to SEQ ID NO:33; or C271G/R with respect to SEQ ID NO:34; or C176G/R with respect to SEQ ID NO:35.

In some embodiments, the invention is directed to compositions comprising TdT variants comprising amino acid sequence having at least 90 percent identity, or in some embodiments, at least 95 percent identity, or in some embodiments, at least 97 percent identity, or in some embodiments, at least 98 percent identity, with a reference or wild type TdT sequence selected from the group consisting of SEQ ID NOs: 2, 11, 13, 15, 17, 19, 21, 23, 25, 27, 29, 31, 33 and 35, wherein (i) such TdT variants have a mutation selected from C173G/R/P/A/V/S/N/Q/D, such as C173G/R (wherein the amino acid residue number is with respect to SEQ ID NO: 2, or an equivalent residue number of SEQ ID NOs 11, 13, 15, 17, 19, 21, 23, 25, 27, 29, 31, 33 or 35) and (ii) such TdT variants incorporate a modified nucleotide, such as a 3'-O-modified nucleoside triphosphates, with greater efficiency, or at a higher rate, than the reference or wild type TdT.

In some embodiments, it is also an object of the invention to provide truncated variants of Terminal deoxynucleotidyl Transferase (TdT) each of which (i) comprises an amino acid sequence with at least 95 percent identity to any of SEQ ID NOs:11, 13, 15, 17, 19, 21, 23, 25, 27, 29, 31, 33 or 35 with at least two amino acid substitutions, such as at least three amino acid substitutions, selected from M192R/Q, L260P, C302G/R, R336L/N, D379V, R454P/N and E457N/L/T/S, (wherein residue numbers are with respect to SEQ ID NO: 1 or with respect to their functionally equivalent residues numbers in SEQ ID NOs 11, 13, 15, 17, 19, 21, 23, 25, 27, 29, 31, 33 or 35), (ii) is able to synthesize a nucleic acid fragment without a template and (iii) is able to incorporate a modified nucleotide into the nucleic acid fragment, for example, a 3'-O-reversibly blocked deoxynucleoside triphosphate onto a free 3'-hydroxyl of a nucleic acid fragment. In further embodiments, the above percent sequence identity value is at least 98 percent identity with the specified sequences.

It is another object of the invention to provide a nucleic acid molecule encoding a variant of a TdT as defined above and/or an expression vector comprising such nucleic acid molecule, and/or a host cell comprising such nucleic acid molecule or expression vector.

It is a further object of the invention to provide a process for producing a variant of TdT according to the invention, wherein a host cell as defined above is cultivated under culture conditions allowing the expression of the nucleic acid encoding said variant, and wherein the variant is optionally retrieved.

The invention further relates to the use of a variant of TdT, for synthesizing a nucleic acid molecule without template, by the successive addition of one or more 3'O-modified nucleotides to a nucleic acid fragment. In some embodiments, such methods comprise the steps of (a) providing an initiator comprising an oligonucleotide having a free 3'-hydroxyl; (b) reacting under enzymatic extension conditions a TdT variant of the invention with the initiator or an extended initiator in the presence of a 3'-O-reversibly blocked nucleoside. In some embodiments, such method further includes steps of (c) deblocking the extended initiators to form extended initiators with free 3'-hydroxyls and (d) repeating steps (b) and (c) until a nucleic acid molecule of a predetermined sequence is synthesized.

It is also an object of the invention to provide a process for synthesizing a nucleic acid molecule without template, comprising a step of contacting a nucleic acid primer with both at least one nucleotide, such as at least one modified nucleotides, such as a 3'O-modified nucleotide, and a variant of TdT according to the invention.

The present invention further provides a kit for performing a nucleotide incorporation reaction comprising a variant of TdT according to the invention, and one or more nucleotides, such as one or more modified nucleotides, such as a 3'O-modified nucleotides, and optionally at least one nucleic acid primer.

DESCRIPTION OF THE INVENTION

Figure 1:
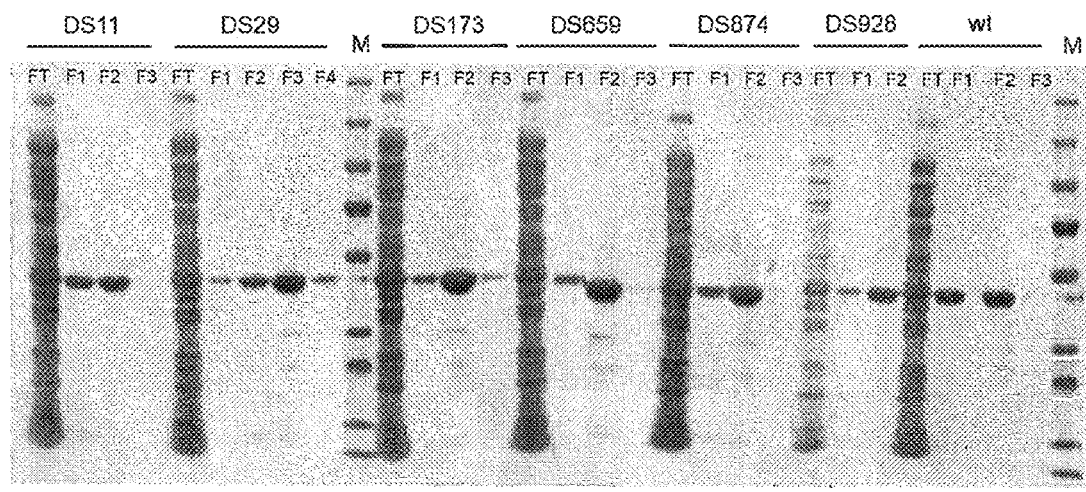
FIG. 1: Purification assay of wild type (wt) TdT and different TdT variants of the invention. Protein samples were loaded on SDS-PAGE analysis gel and migrated through electrophoresis.

The DNA polymerase families are divided into seven families based on their sequence homology and crystal structure. Among them, the polymerases of PolX family represent a wide variety of polymerases from replicative polymerases to terminal transferase enzymes. Polymerases from PolX family are present across a very wide range of eukaryotic organisms. Polymerases from the PolX family are implicated in a vast variety of biological processes and in particular in DNA damage repair mechanisms or error correction mechanisms. The PolX family regroups polymerase β (Pol β), μ (Pol μ), λ (Pol λ), IV from yeast (Pol IV) and the Terminal deoxynucleotidyl Transferase (TdT). TdT is naturally implicated in DNA repair and maintenance mechanisms. In particular, TdT has the unique ability to conserve a nucleotide polymerization activity even in absence of template strand. In specific conditions and with natural nucleotides, TdT is able to elongate DNA fragments with several hundred nucleotides, in absence of any complementary strand. However, wild type TdT is totally unable to efficiently incorporate sugar-modified nucleotides.

It is thus the purpose of the present invention to provide variants of TdT with targeted mutation(s) that allow them to incorporate modified nucleotides into a nucleic fragment during synthesize of said nucleotide fragment. More particularly, the inventors have identified specific amino acid residues that may be advantageously substituted, alone or in combination, to improve the ability of the enzyme to synthesize nucleic acid fragments of various length and with pre-determined sequence, including by using modified nucleotides.

Definitions

As used therein, the terms "mutant" and "variant" may be used interchangeably to refer to polypeptides related to or derived from SEQ ID NOs:2, 11, 12, 13, 14, 15, 16, 17, 18, 19, 20, 21, 22, 23, 24, 25, 26 27, 28, 29, 30, 31, 32, 33, 34 or 35 and comprising a modification or an alteration, i.e., a substitution, insertion, and/or deletion, at one or more (e.g., several) positions and having both a polymerase activity without template and ability to incorporate 3'-O-modified nucleoside triphosphates into a nucleic acid chain. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. Mutagenesis activities consist in deleting, inserting or substituting one or several amino-acids in the sequence of a protein or in the case of the invention of a polymerase. Targeted amino-acids could be concomitant or distributed along the whole sequence of the polymerase. Specific motifs or structural features could be targeted for example.

The terms "modification" or "alteration" as used herein in relation to a position or amino acid mean that the amino acid in the specific position has been modified compared to the amino acid of the wild-type protein.

A "substitution" means that an amino acid residue is replaced by another amino acid residue. For example, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). For example, the term "substitution" refers to the replacement of an amino acid residue by another selected from the naturally-occurring standard 20 amino acid residues. The sign "+" indicates a combination of substitutions.

The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N:

asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

As used hercin, the terms "sequence identity" or "identity" refer to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are aligned using a global alignment algorithm (e.g. Needleman and Wunsch algorithm; Needleman and Wunsch, 1970) which aligns the sequences optimally over the entire length, while sequences of substantially different lengths are aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/or http://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

Herein, the terms "peptide", "polypeptide", "protein", "enzyme", refer to a chain of amino acids linked by peptide bonds, regardless of the number of amino acids forming said chain.

Unless otherwise specified, the positions disclosed in the present application are numbered by reference to the amino acid sequence set forth in a specified SEQ ID NO.

Variants of TdT

The present invention provides variants of TdT enzyme that can be used for synthesizing polynucleotides of predetermined sequences, such as DNA or RNA, without the use of template strand. The TdT variants of the invention allow modified nucleotides, and more particularly 3'O-modified nucleotides, to be used in an enzyme-mediated method of polynucleotide synthesis, such as described by Hiatt et al, U.S. Pat. No. 5,763,594.

In some embodiments of the invention, "modified Terminal desoxyribonucleotidyl Transferase", "modified TdT", "variants of Terminal desoxyribonucleotidyl Transferase" and "variants of TdT" refer to enzymes that comprise an amino acid seqment that shares at least 80% identity with an amino acid sequence of one of the amino acid sequences set forth in SEQ ID NOs:2, 11, 13, 15, 17, 19, 21, 23, 25, 27, 29, 31, 33 or 35, excepting at least one amino acid residue substitution. In some embodiments, the variant of TdT comprises an amino acid sequence that shares at least 90% identity with SEQ ID NOs:2, 11, 13, 15, 17, 19, 21, 23, 25, 27, 29, 31, 33, 35, and having at least one amino acid residue substitution. In still other embodiments, the variant of TdT comprises an amino acid sequence that shares at least 95% identity with SEQ ID NOs:2, 11, 13, 15, 17, 19, 21, 23, 25, 27, 29, 31, 33, 35, and having at least one amino acid residue substitution. In still other embodiments, the variant of TdT comprises an amino acid sequence that shares at least 98% identity with SEQ ID NOs:2, 11, 13, 15, 17, 19, 21, 23, 25, 27, 29, 31, 33, 35, and having at least one amino acid residue substitution.

In some cases, variants of the present invention may be described according to their mutations on specific residues, whose positions are determined by alignment with or reference to the enzymatic sequence SEQ ID NO:1 or SEQ ID NO:2, which corresponds to the amino acid sequences of murine TdT and truncated murine TdT respectivelly. The variants of the invention may also be described directly with reference to SEQ ID numbers of corresponding reference sequences.

By "functionally equivalent residue" is meant a residue in a sequence of a TdT of sequence homologous to SEQ ID NO: 1 or to SEQ ID NO:2 and having an identical functional role. Functionally equivalent residues are identified by using sequence alignments, for example, using the Mutalin line alignment software (http://multalin.toulouse.inra.fr/multalin/multalin.html; 1988, Nucl. Acids Res., 16 (22), 10881-10890). After alignment, the functionally equivalent residues are at homologous positions on the different sequences considered. Sequence alignments and identification of functionally equivalent residues may be between any TdT and their natural variants, including inter-species.

TdT can be found in many organisms or microorganisms. All those TdT are good candidates for performing the present invention. In particular, modifications to alter a particular TdT sequence to give said polymerase an increased ability to incorporate modified nucleotides, can target any other TdT sequence. Accordingly, mutations or combinations described herein by reference to SEQ ID NO: 1, and more particularly to SEQ ID NO:2 that corresponds to amino acid residues 130 to 510 of SEQ ID NO:1, can be transposed to any other TdT sequence.

In some embodiments, the invention comprises a variant of Terminal deoxynucleotidyl Transferase (TdT) that (i) comprises an amino acid sequence having at least 80%, such as at least 85%, 90%, 95% or 99% identity with an amino acid sequence selected from SEQ ID NO: 2, 11, 13, 15, 17, 19, 21, 23, 25, 27, 29, 31, 33 or 35, with at least an amino acid substitution at position corresponding to a functionally equivalent residue of residue C173 with respect to SEQ ID NO: 11, (ii) is able to synthesize a nucleic acid fragment without template and (iii) is able to incorporate a modified nucleoside triphosphate, such as a 3'-O-blocked nucleoside triphosphate, into the nucleic fragment.

Indeed, the inventors have discovered that such substitution has a great impact on both surface and interaction properties of the enzyme with nucleotides, which may allow incorporation of 3'O-modified nucleotides in a nucleic acid sequence.

Further embodiments of TdT variants of the invention are listed as entries in Tables 1A through 1C (single substitutions), Tables 2A through 2C (two substitutions), Tables 3A through 3C (three substitutions), and Tables 4A through 4F (four substitutions), wherein each such variant TdT is defined by the indicated SEQ ID NO in the righthand column modified by the substitution(s) listed in the lefthand column of the same row as the SEQ ID NO. A "non-wild type" substitution means that the substitution may be any amino acid except for the amino acid at the indicated position in the wild type sequence, or equivalently, the sequence of the indicated SEQ ID NO.

TABLE 1A

TdT variants at position C173 (SEQ ID NO: 2) or functionally equivalent positions of the indicated SEQ ID NO

| Non-wild type substitution at | SEQ ID NO |
|---|---|
| C173 | 2 |
| C313 | 10 |
| C173 | 11 |
| C302 | 12 |
| C173 | 13 |
| C302 | 14 |
| C172 | 15 |
| C304 | 16 |
| C173 | 17 |
| C304 | 18 |
| C173 | 19 |
| C293 | 20 |
| C173 | 21 |
| C282 | 22 |
| C178 | 23 |
| C304 | 24 |
| C174 | 25 |
| C300 | 26 |
| C171 | 27 |
| C305 | 28 |
| C173 | 29 |
| C302 | 30 |
| C173 | 31 |
| C313 | 32 |
| C182 | 33 |
| C271 | 34 |
| C176 | 35 |

TABLE 1B

Further TdT variants at position C173 (SEQ ID NO: 2) or functionally equivalent positions of the indicated SEQ ID NO

| Substitution | SEQ ID NO |
|---|---|
| C173/G/R/P/A/V/S/N/Q/D | 2 |
| C313/G/R/P/A/V/S/N/Q/D | 10 |
| C173/G/R/P/A/V/S/N/Q/D | 11 |
| C302/G/R/P/A/V/S/N/Q/D | 12 |
| C173/G/R/P/A/V/S/N/Q/D | 13 |
| C302/G/R/P/A/V/S/N/Q/D | 14 |
| C172/G/R/P/A/V/S/N/Q/D | 15 |
| C304/G/R/P/A/V/S/N/Q/D | 16 |
| C173/G/R/P/A/V/S/N/Q/D | 17 |
| C304/G/R/P/A/V/S/N/Q/D | 18 |
| C173/G/R/P/A/V/S/N/Q/D | 19 |
| C293/G/R/P/A/V/S/N/Q/D | 20 |
| C173/G/R/P/A/V/S/N/Q/D | 21 |
| C282/G/R/P/A/V/S/N/Q/D | 22 |
| C178/G/R/P/A/V/S/N/Q/D | 23 |
| C304/G/R/P/A/V/S/N/Q/D | 24 |
| C174/G/R/P/A/V/S/N/Q/D | 25 |
| C300/G/R/P/A/V/S/N/Q/D | 26 |
| C171/G/R/P/A/V/S/N/Q/D | 27 |
| C305/G/R/P/A/V/S/N/Q/D | 28 |
| C173/G/R/P/A/V/S/N/Q/D | 29 |
| C302/G/R/P/A/V/S/N/Q/D | 30 |
| C173/G/R/P/A/V/S/N/Q/D | 31 |
| C313/G/R/P/A/V/S/N/Q/D | 32 |
| C182/G/R/P/A/V/S/N/Q/D | 33 |
| C271/G/R/P/A/V/S/N/Q/D | 34 |
| C176/G/R/P/A/V/S/N/Q/D | 35 |

TABLE 1C

Further TdT variants at position C173 (SEQ ID NO: 2) or functionally equivalent positions of the indicated SEQ ID NO

| Substitutions | SEQ ID NO |
|---|---|
| C173/G/R | 2 |
| C313/G/R | 10 |
| C173/G/R | 11 |
| C302/G/R | 12 |
| C173/G/R | 13 |
| C302/G/R | 14 |
| C172/G/R | 15 |
| C304/G/R | 16 |
| C173/G/R | 17 |
| C304/G/R | 18 |
| C173/G/R | 19 |
| C293/G/R | 20 |
| C173/G/R | 21 |
| C282/G/R | 22 |
| C178/G/R | 23 |
| C304/G/R | 24 |
| C174/G/R | 25 |
| C300/G/R | 26 |
| C171/G/R | 27 |
| C305/G/R | 28 |
| C173/G/R | 29 |
| C302/G/R | 30 |
| C173/G/R | 31 |
| C313/G/R | 32 |
| C182/G/R | 33 |
| C271/G/R | 34 |
| C176/G/R | 35 |

TABLE 2A

Further TdT variants at position C173 (SEQ ID NO: 2) and position M63 (SEQ ID NO: 2) or functionally equivalent positions of the indicated SEQ ID NO

| Non-wildtype substitutions at locations | SEQ ID NO |
|---|---|
| M63 + C173 | 2 |
| M63 + C173 | 11 |
| M63 + C173 | 13 |
| L62 + C172 | 15 |
| M63 + C173 | 17 |
| M63 + C173 | 19 |
| R64 + C173 | 21 |
| M73 + C178 | 23 |
| M64 + C174 | 25 |
| M61 + C171 | 27 |

TABLE 2A-continued

Further TdT variants at position C173 (SEQ ID NO: 2) and position M63 (SEQ ID NO: 2) or functionally equivalent positions of the indicated SEQ ID NO

| Non-wildtype substitutions at locations | SEQ ID NO |
|---|---|
| M63 + C173 | 29 |
| L63 + C173 | 31 |
| M63 + C182 | 33 |
| M66 + C176 | 35 |

TABLE 2B

Further TdT variants at position C173 (SEQ ID NO: 2) and position M63 (SEQ ID NO: 2) or functionally equivalent positions of the indicated SEQ ID NO

| Substitutions and substitution positions | SEQ ID NO |
|---|---|
| M63R/Q/G/A/V/D/N/H/E + C173G/R/P/A/V/S/N/Q/D | 2 |
| M63R/Q/G/A/V/D/N/H/E + C173G/R/P/A/V/S/N/Q/D | 11 |
| M63R/Q/G/A/V/D/N/H/E + C173G/R/P/A/V/S/N/Q/D | 13 |
| L62R/Q/G/A/V/D/N/H/E + C172G/R/P/A/V/S/N/Q/D | 15 |
| M63R/Q/G/A/V/D/N/H/E + C173G/R/P/A/V/S/N/Q/D | 17 |
| M63R/Q/G/A/V/D/N/H/E + C173G/R/P/A/V/S/N/Q/D | 19 |
| R64R/Q/G/A/V/D/N/H/E + C173G/R/P/A/V/S/N/Q/D | 21 |
| M73R/Q/G/A/V/D/N/H/E + C178G/R/P/A/V/S/N/Q/D | 23 |
| M64R/Q/G/A/V/D/N/H/E + C174G/R/P/A/V/S/N/Q/D | 25 |
| M61R/Q/G/A/V/D/N/H/E + C171G/R/P/A/V/S/N/Q/D | 27 |
| M63R/Q/G/A/V/D/N/H/E + C173G/R/P/A/V/S/N/Q/D | 29 |
| L63R/Q/G/A/V/D/N/H/E + C173G/R/P/A/V/S/N/Q/D | 31 |
| M63R/Q/G/A/V/D/N/H/E + C182G/R/P/A/V/S/N/Q/D | 33 |
| M66R/Q/G/A/V/D/N/H/E + C176G/R/P/A/V/S/N/Q/D | 35 |

TABLE 2C

Further TdT variants at position C173 (SEQ ID NO: 2) and position M63 (SEQ ID NO: 2) or functionally equivalent positions of the indicated SEQ ID NO

| Substitutions and substitution positions | SEQ ID NO |
|---|---|
| M63R/Q + C173G/R | 2 |
| M63R/Q + C173G/R | 11 |
| M63R/Q + C173G/R | 13 |
| L62R/Q + C172G/R | 15 |
| M63R/Q + C173G/R | 17 |
| M63R/Q + C173G/R | 19 |
| R64R/Q + C173G/R | 21 |
| M73R/Q + C178G/R | 23 |
| M64R/Q + C174G/R | 25 |
| M61R/Q + C171G/R | 27 |
| M63R/Q + C173G/R | 29 |
| L63R/Q + C173G/R | 31 |
| M63R/Q + C182G/R | 33 |
| M66R/Q + C176G/R | 35 |

TABLE 3A

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63 + C173 + R207 | 2 |
| M63 + C173 + R207 | 11 |
| M63 + C173 + R207 | 13 |
| L62 + C172 + R206 | 15 |
| M63 + C173 + R207 | 17 |
| M63 + C173 + R207 | 19 |
| R64 + C173 + R208 | 21 |
| M73 + C178 + R207 | 23 |
| M64 + C174 + R208 | 25 |
| M61 + C171 + R205 | 27 |
| M63 + C173 + R207 | 29 |
| L63 + C173 + R207 | 31 |
| M63 + C182 + R216 | 33 |
| M66 + C176 + R210 | 35 |

TABLE 3B

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P | 2 |
| M63R/Q/G/A/V/D/N/H/E + C173G/R/P/A/V/S/N/Q/D + R207 N/L/K/H/G/D/A/P | 11 |
| M63R/Q/G/A/V/D/N/H/E + C173G/R/P/A/V/S/N/Q/D + R207 N/L/K/H/G/D/A/P | 13 |
| L62R/Q/G/A/V/D/N/H/E + C172G/R/P/A/V/S/N/Q/D + R206 N/L/K/H/G/D/A/P | 15 |
| M63R/Q/G/A/V/D/N/H/E + C173G/R/P/A/V/S/N/Q/D + R207 N/L/K/H/G/D/A/P | 17 |
| M63R/Q/G/A/V/D/N/H/E + C173G/R/P/A/V/S/N/Q/D + R207 N/L/K/H/G/D/A/P | 19 |
| R64Q/G/A/V/D/N/H/E + C173G/R/P/A/V/S/N/Q/D + R208 N/L/K/H/G/D/A/P | 21 |
| M73R/Q/G/A/V/D/N/H/E + C178G/R/P/A/V/S/N/Q/D + R207 N/L/K/H/G/D/A/P | 23 |
| M64R/Q/G/A/V/D/N/H/E + C174G/R/P/A/V/S/N/Q/D + R208 N/L/K/H/G/D/A/P | 25 |
| M61R/Q/G/A/V/D/N/H/E + C171G/R/P/A/V/S/N/Q/D + R205 N/L/K/H/G/D/A/P | 27 |
| M63R/Q/G/A/V/D/N/H/E + C173G/R/P/A/V/S/N/Q/D + R207 N/L/K/H/G/D/A/P | 29 |
| L63R/Q/G/A/V/D/N/H/E + C173G/R/P/A/V/S/N/Q/D + R207N/L/K/H/G/D/A/P | 31 |
| M63R/Q/G/A/V/D/N/H/E + C182G/R/P/A/V/S/N/Q/D 2 + R216N/L/K/H/G/D/A/P | 33 |
| M66R/Q/G/A/V/D/N/H/E + C176G/R/P/A/V/S/N/Q/D + R210N/L/K/H/G/D/A/P | 35 |

TABLE 3C

Further TdT variants at positions C173 (SEQ ID NO: 2), M63 (SEQ ID NO: 2) and R207 (SEQ ID NO: 2) or functionally equivalent positions of the indicated SEQ ID NO

| Mutations | SEQ ID NO |
|---|---|
| M63R/Q + C173G/R + R207L/N | 2 |
| M63R/Q + C173G/R + R207L/N | 11 |
| M63R/Q + C173G/R + R207L/N | 13 |
| M62R/Q + C172G/R + R206L/N | 15 |
| M63R/Q + C173G/R + R207L/N | 17 |
| M63R/Q + C173G/R + R207L/N | 19 |
| R64Q + C173G/R + R208L/N | 21 |
| M73R/Q + C178G/R + R207N/L | 23 |
| M64R/Q + C174G/R + R208 N/L | 25 |
| M61R/Q + C171G/R + R205N/L | 27 |
| M63R/Q + C173G/R + R207L/N | 29 |
| L63R/Q + C173G/R + R207L/N | 31 |
| M63R/Q + C182G/R + R216N/L | 33 |
| M66R/Q + C176G/R + R210N/L | 35 |

TABLE 4A

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63 + C173 + R207 + R325 | 2 |
| M63 + C173 + R207 + R324 | 11 |
| M63 + C173 + R207 + R324 | 13 |
| L62 + C172 + R206 + R320 | 15 |
| M63 + C173 + R207 + R331 | 17 |
| M63 + C173 + R207 + P325 | 19 |
| R64 + C173 + R208 + T331 | 21 |
| M73 + C178 + R207 + R325 | 23 |
| M64 + C174 + R208 + P326 | 25 |
| M61 + C171 + R205 + R323 | 27 |
| M63 + C173 + R207 + R328 | 29 |
| L63 + C173 + R207 + R325 | 31 |
| M63 + C182 + R216 + R338 | 33 |
| M66 + C176 + R210 + R328 | 35 |

TABLE 4B

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P + R325P/N/A/L/K/H/G/D | 2 |
| M63R/Q/G/A/V/D/N/H/E + C173G/R/P/A/V/S/N/Q/D + R207 N/L/K/H/G/D/A/P + R324P/N/A/L/K/H/G/D | 11 |
| M63R/Q/G/A/V/D/N/H/E + C173G/R/P/A/V/S/N/Q/D + R207 N/L/K/H/G/D/A/P + R324P/N/A/L/K/H/G/D | 13 |
| L62R/Q/G/A/V/D/N/H/E + C172G/R/P/A/V/S/N/Q/D + R206 N/L/K/H/G/D/A/P + R320P/N/A/L/K/H/G/D | 15 |
| M63R/Q/G/A/V/D/N/H/E + C173G/R/P/A/V/S/N/Q/D + R207 N/L/K/H/G/D/A/P + R331P/N/A/L/K/H/G/D | 17 |
| M63R/Q/G/A/V/D/N/H/E + C173G/R/P/A/V/S/N/Q/D + R207 N/L/K/H/G/D/A/P + R325N/A/L/K/H/G/D | 19 |
| R64Q/G/A/V/D/N/H/E + C173G/R/P/A/V/S/N/Q/D + R208 N/L/K/H/G/D/A/P + T331P/N/A/L/K/H/G/D | 21 |
| M73R/Q/G/A/V/D/N/H/E + C178G/R/P/A/V/S/N/Q/D + R207 N/L/K/H/G/D/A/P + R325P/N/A/L/K/H/G/D | 23 |
| M64R/Q/G/A/V/D/N/H/E + C174G/R/P/A/V/S/N/Q/D + R208 N/L/K/H/G/D/A/P + P326N/A/L/K/H/G/D | 25 |
| M61R/Q/G/A/V/D/N/H/E + C171G/R/P/A/V/S/N/Q/D + R205 N/L/K/H/G/D/A/P + R323P/N/A/L/K/H/G/D | 27 |
| M63R/Q/G/A/V/D/N/H/E + C173G/R/P/A/V/S/N/Q/D + R207 N/L/K/H/G/D/A/P + R328P/N/A/L/K/H/G/D | 29 |
| L63R/Q/G/A/V/D/N/H/E + C173G/R/P/A/V/S/N/Q/D + R207N/L/K/H/G/D/A/P + R325P/N/A/L/K/H/G/D | 31 |
| M63R/Q/G/A/V/D/N/H/E + C182G/R/P/A/V/S/N/Q/D + R216N/L/K/H/G/D/A/P + R338P/N/A/L/K/H/G/D | 33 |
| M66R/Q/G/A/V/D/N/H/E + C176G/R/P/A/V/S/N/Q/D + R210N/L/K/H/G/D/A/P + R328P/N/A/L/K/H/G/D | 35 |

TABLE 4C

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| M63R/Q + C173G/R + R207N/L + R325P/N | 2 |
| M63R/Q + C173G/R + R207N/L + R324P/N | 11 |
| M63R/Q + C173G/R + R207N/L + R324P/N | 13 |
| L62R/Q + C172G/R + R206N/L + R320P/N | 15 |
| M63R/Q + C173G/R + R207N/L + R331P/N | 17 |
| M63R/Q + C173G/R + R207N/L + P325N | 19 |

TABLE 4C-continued

Further TdT variants at positions C173 (SEQ ID NO: 2), M63 (SEQ ID NO: 2), R207 (SEQ ID NO: 2) and R325 (SEQ ID NO: 2) or functionally equivalent positions of the indicated SEQ ID NO

| Mutations | SEQ ID NO |
|---|---|
| R64Q/G + C173G/R + R208N/L + T331P/N | 21 |
| M73R/Q/G + C178G/R + R207N/L + R325P/N | 23 |
| M64R/Q + C174G/R + R208N/L + P326N | 25 |
| M61R/Q + C171G/R + R205N/L + R323P/N | 27 |
| M63R/Q + C173G/R + R207N/L + R328P/N | 29 |
| L63R/Q + C173G/R + R207N/L + R325P/N | 31 |
| M63R/Q + C182G/R + R216N/L + R338P/N | 33 |
| M66R/Q + C176G/R + R210N/L + R328P/N | 35 |

TABLE 4D

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63 + C173 + R207 + E328 | 2 |
| M63 + C173 + R207 + E327 | 11 |
| M63 + C173 + R207 + E327 | 13 |
| L62 + C172 + R206 + G323 | 15 |
| M63 + C173 + R207 + E334 | 17 |
| M63 + C173 + R207 + E327 | 19 |
| R64 + C173 + R208 + E334 | 21 |
| M73 + C178 + R207 + E328 | 23 |
| M64 + C174 + R208 + E329 | 25 |
| M61 + C171 + R205 + E326 | 27 |
| M63 + C173 + R207 + E331 | 29 |
| L63 + C173 + R207 + E328 | 31 |
| M63 + C182 + R216 + E341 | 33 |
| M66 + C176 + R210 + E331 | 35 |

TABLE 4E

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63R/Q/G/A/V/D/N/H/E + C173G/R/P/A/V/S/N/Q/D + R207N/L/K/H/G/D/A/P + E328N/L/T/S | 2 |
| M63R/Q/G/A/V/D/N/H/E + C173G/R/P/A/V/S/N/Q/D + R207 N/L/K/H/G/D/A/P + E327N/L/T/S | 11 |
| M63R/Q/G/A/V/D/N/H/E + C173G/R/P/A/V/S/N/Q/D + R207 N/L/K/H/G/D/A/P + E327N/L/T/S | 13 |
| L62R/Q/G/A/V/D/N/H/E + C172G/R/P/A/V/S/N/Q/D + R206 N/L/K/H/G/D/A/P + G323N/L/T/S | 15 |
| M63R/Q/G/A/V/D/N/H/E + C173G/R/P/A/V/S/N/Q/D + R207 N/L/K/H/G/D/A/P + E334N/L/T/S | 17 |
| M63R/Q/G/A/V/D/N/H/E + C173G/R/P/A/V/S/N/Q/D + R207 N/L/K/H/G/D/A/P + E327N/L/T/S | 19 |
| R64Q/G/A/V/D/N/H/E + C173G/R/P/A/V/S/N/Q/D + R208 N/L/K/H/G/D/A/P + E334N/L/T/S | 21 |
| M73R/Q/G/A/V/D/N/H/E + C178G/R/P/A/V/S/N/Q/D + R207 N/L/K/H/G/D/A/P + E328N/L/T/S | 23 |
| M64R/Q/G/A/V/D/N/H/E + C174G/R/P/A/V/S/N/Q/D + R208 N/L/K/H/G/D/A/P + E329N/L/T/S | 25 |
| M61R/Q/G/A/V/D/N/H/E + C171G/R/P/A/V/S/N/Q/D + R205 N/L/K/H/G/D/A/P + E326N/L/T/S | 27 |
| M63R/Q/G/A/V/D/N/H/E + C173G/R/P/A/V/S/N/Q/D + R207 N/L/K/H/G/D/A/P + E331N/L/T/S | 29 |
| L63R/Q/G/A/V/D/N/H/E + C173G/R/P/A/V/S/N/Q/D + R207N/L/K/H/G/D/A/P + E328N/L/T/S | 31 |
| M63R/Q/G/A/V/D/N/H/E + C182G/R/P/A/V/S/N/Q/D + R216N/L/K/H/G/D/A/P + E341N/L/T/S | 33 |

TABLE 4E-continued

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M66R/Q/G/A/V/D/N/H/E + C176G/R/P/A/V/S/N/Q/D + R210N/L/K/H/G/D/A/P + E331N/L/T/S | 35 |

TABLE 4F

Further TdT variants at positions C173 (SEQ ID NO: 2), M63 (SEQ ID NO: 2), R207 (SEQ ID NO: 2) and E328 (SEQ ID NO: 2) or functionally equivalent positions of the indicated SEQ ID NO

| Mutations | SEQ ID NO |
|---|---|
| M63R/Q + C173G/R + R207N/L + E328N/L/T/S | 2 |
| M63R/Q + C173G/R + R207 N/L + E327N/L/T/S | 11 |
| M63R/Q + C173G/R + R207N/L + E327N/L/T/S | 13 |
| L62R/Q + C172G/R + R206N/L + G323N/L/T/S | 15 |
| M63R/Q + C173G/R + R207N/L + E334N/L/T/S | 17 |
| M63R/Q + C173G/R + R207N/L + E327N/L/T/S | 19 |
| R64Q/G + C173G/R + R208N/L + E334N/L/T/S | 21 |
| M73R/Q + C178G/R + R207N/L + E328N/L/T/S | 23 |
| M64R/Q + C174G/R + R208N/L + E329N/L/T/S | 25 |
| M61R/Q + C171G/R + R205N/L + E326N/L/T/S | 27 |
| M63R/Q/G + C173G/R + R207N/L + E331N/L/T/S | 29 |
| L63R/Q + C173G/R + R207N/L + E328N/L/T/S | 31 |
| M63R/Q + C182G/R + R216N/L + E341N/L/T/S | 33 |
| M66R/Q + C176G/R + R210N/L + E331N/L/T/S | 35 |

Advantageously, the substitution is selected from CzzzG/R/P/A/V/S/N/Q/D, where Czzz represents an amino acid residue number functionally equivalent to C173 of SEQ ID NO:2 in SEQ ID NOs:11, 13, 15, 17, 19, 21, 23, 25, 27, 29, 31, 33 and 35, respectively, and such as from CzzzG/R, where Czzz represents an amino acid residue number functionally equivalent to C173 of SEQ ID NO: 2 in SEQ ID NOs:11, 13, 15, 17, 19, 21, 23, 25, 27, 29, 31, 33 and 35, respectively.

In a particular embodiment, the variant further comprises at least one amino acid substitution at position corresponding to functionally equivalent residues of residues selected from M63, R207, R324 and E327, of SEQ ID NO:11.

According to the invention, all variants of TdT as disclosed above are able to both synthesize a nucleic acid fragment without template and incorporate a modified nucleotide into the nucleic acid fragment. Advantageously, said variants have an increased ability to incorporate a modified nucleotide, such as a 3'O-modified nucleotide, into a nucleic acid fragment as compared to a TdT of SEQ ID NOs:2, 11, 13, 15, 17, 19, 21, 23, 25, 27, 29, 31, 33 and 35.

In some of the embodiments described above, the efficiency of a variant TdT in incorporating a 3'O-modified nucleoside triphosphate is at least 110 percent that of a wild type TdT of sequence SEQ ID NO:2, 11, 13, 15, 17, 19, 21, 23, 25, 27, 29, 31, 33 and 35 in other embodiments, the efficiency of a variant TdT in incorporating a 3'O-modified nucleoside triphosphate is at least 150 percent that of a wild type TdT of sequence SEQ ID NOs:2, 11, 13, 15, 17, 19, 21, 23, 25, 27, 29, 31, 33 and 35; in other embodiments, the efficiency of a variant TdT in incorporating a 3'O-modified nucleoside triphosphate is at least 200 percent that of a wild type TdT of sequence SEQ ID NOs:2, 11, 13, 15, 17, 19, 21, 23, 25, 27, 29, 31, 33 and 35.

The present invention further provides a variant of TdT having the amino acid sequence as set forth in SEQ ID NO:2 or functionally equivalent sequence, with at least one substitution or combination of substitutions as listed in Table 5 or Table 6. The variants of the invention comprise at least the amino acid substitutions listed in the left column and called "Variable Mutations", or functionally equivalent residues, and optionally one or both combination of substitutions listed in the right column and called "Optional Constant Mutations", or functionally equivalent sequence.

TABLE 5

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS1 | M63R + L131P + C173R + R207L + D250V + R325P + E328L | L52F + A108V + R354K and/or G284L/S + H287D + E289A |
| DS2 | M63R + L131P + C173R + R207L + D250V + R325P + E328N | L52F + A108V + R354K and/or G284L/S + H287D + E289A |
| DS3 | M63R + L131P + C173R + R207L + D250V + R325P | L52F + A108V + R354K and/or G284L/S + H287D + E289A |
| DS4 | M63R + L131P + C173R + R207L + D250V + R325A + E328L | L52F + A108V + R354K and/or G284L/S + H287D + E289A |
| DS5 | M63R + L131P + C173R + R207L + D250V + R325A + E328N | L52F + A108V + R354K and/or G284L/S + H287D + E289A |
| DS6 | M63R + L131P + C173R + R207L + D250V + R325A | L52F + A108V + R354K and/or G284L/S + H287D + E289A |
| DS7 | M63R + L131P + C173R + R207L + D250V + E328L | L52F + A108V + R354K and/or G284L/S + H287D + E289A |
| DS8 | M63R + L131P + C173R + R207L + D250V + E328N | L52F + A108V + R354K and/or G284L/S + H287D + E289A |
| DS9 | M63R + L131P + C173R + R207L + D250V | L52F + A108V + R354K and/or G284L/S + H287D + E289A |
| DS10 | M63R + L131P + C173R + R207L + R325P + E328L | L52F + A108V + R354K and/or G284L/S + H287D + E289A |
| DS11 | M63R + L131P + C173R + R207L + R325P + E328N | L52F + A108V + R354K and/or G284L/S + H287D + E289A |
| DS12 | M63R + L131P + C173R + R207L + R325P | L52F + A108V + R354K and/or G284L/S + H287D + E289A |
| DS13 | M63R + L131P + C173R + R207L + R325A + E328L | L52F + A108V + R354K and/or G284L/S + H287D + E289A |
| DS14 | M63R + L131P + C173R + R207L + R325A + E328N | L52F + A108V + R354K and/or G284L/S + H287D + E289A |
| DS15 | M63R + L131P + C173R + R207L + R325A | L52F + A108V + R354K and/or G284L/S + H287D + E289A |
| DS16 | M63R + L131P + C173R + R207L + E328L | L52F + A108V + R354K and/or G284L/S + H287D + E289A |
| DS17 | M63R + L131P + C173R + R207L + E328N | L52F + A108V + R354K and/or G284L/S + H287D + E289A |
| DS18 | M63R + L131P + C173R + R207L | L52F + A108V + R354K and/or G284L/S + H287D + E289A |
| DS19 | M63R + L131P + C173R + R207N + D250V + R325P + E328L | L52F + A108V + R354K and/or G284L/S + H287D + E289A |
| DS20 | M63R + L131P + C173R + R207N + D250V + R325P + E328N | L52F + A108V + R354K and/or G284L/S + H287D + E289A |
| DS21 | M63R + L131P + C173R + R207N + D250V + R325P | L52F + A108V + R354K and/or G284L/S + H287D + E289A |
| DS22 | M63R + L131P + C173R + R207N + D250V + R325A + E328L | L52F + A108V + R354K and/or G284L/S + H287D + E289A |
| DS23 | M63R + L131P + C173R + R207N + D250V + R325A + E328N | L52F + A108V + R354K and/or G284L/S + H287D + E289A |
| DS24 | M63R + L131P + C173R + R207N + D250V + R325A | L52F + A108V + R354K and/or G284L/S + H287D + E289A |
| DS25 | M63R + L131P + C173R + R207N + D250V + E328L | L52F + A108V + R354K and/or G284L/S + H287D + E289A |
| DS26 | M63R + L131P + C173R + R207N + D250V + E328N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS27 | M63R + L131P + C173R + R207N + D250V | L52F + A108V + R354K and/or G284L/S + H287D + E289A |
| DS28 | M63R + L131P + C173R + R207N + R325P + E328L | L52F + A108V + R354K and/or G284L/S + H287D + E289A |
| DS29 | M63R + L131P + C173R + R207N + R325P + E328N | L52F + A108V + R354K and/or G284L/S + H287D + E289A |
| DS30 | M63R + L131P + C173R + R207N + R325P | L52F + A108V + R354K and/or G284L/S + H287D + E289A |
| DS31 | M63R + L131P + C173R + R207N + R325A + E328L | L52F + A108V + R354K and/or G284L/S + H287D + E289A |
| DS32 | M63R + L131P + C173R + R207N + R325A + E328N | L52F + A108V + R354K and/or G284L/S + H287D + E289A |
| DS33 | M63R + L131P + C173R + R207N + R325A | L52F + A108V + R354K and/or G284L/S + H287D + E289A |
| DS34 | M63R + L131P + C173R + R207N + E328L | L52F + A108V + R354K and/or G284L/S + H287D + E289A |
| DS35 | M63R + L131P + C173R + R207N + E328N | L52F + A108V + R354K and/or G284L/S + H287D + E289A |
| DS36 | M63R + L131P + C173R + R207N | L52F + A108V + R354K and/or G284L/S + H287D + E289A |
| DS37 | M63R + L131P + C173R + D250V + R325P + E328L | L52F + A108V + R354K and/or G284L/S + H287D + E289A |
| DS38 | M63R + L131P + C173R + D250V + R325P + E328N | L52F + A108V + R354K and/or G284L/S + H287D + E289A |
| DS39 | M63R + L131P + C173R + D250V + R325P | L52F + A108V + R354K and/or G284L/S + H287D + E289A |
| DS40 | M63R + L131P + C173R + D250V + R325A + E328L | L52F + A108V + R354K and/or G284L/S + H287D + E289A |
| DS41 | M63R + L131P + C173R + D250V + R325A + E328N | L52F + A108V + R354K and/or G284L/S + H287D + E289A |
| DS42 | M63R + L131P + C173R + D250V + R325A | L52F + A108V + R354K and/or G284L/S + H287D + E289A |
| DS43 | M63R + L131P + C173R + D250V + E328L | L52F + A108V + R354K and/or G284L/S + H287D + E289A |
| DS44 | M63R + L131P + C173R + D250V + E328N | L52F + A108V + R354K and/or G284L/S + H287D + E289A |
| DS45 | M63R + L131P + C173R + D250V | L52F + A108V + R354K and/or G284L/S + H287D + E289A |
| DS46 | M63R + L131P + C173R + R325P + E328L | L52F + A108V + R354K and/or G284L/S + H287D + E289A |
| DS47 | M63R + L131P + C173R + R325P + E328N | L52F + A108V + R354K and/or G284L/S + H287D + E289A |
| DS48 | M63R + L131P + C173R + R325P | L52F + A108V + R354K and/or G284L/S + H287D + E289A |
| DS49 | M63R + L131P + C173R + R325A + E328L | L52F + A108V + R354K and/or G284L/S + H287D + E289A |
| DS50 | M63R + L131P + C173R + R325A + E328N | L52F + A108V + R354K and/or G284L/S + H287D + E289A |
| DS51 | M63R + L131P + C173R + R325A | L52F + A108V + R354K and/or G284L/S + H287D + E289A |
| DS52 | M63R + L131P + C173R + E328L | L52F + A108V + R354K and/or G284L/S + H287D + E289A |
| DS53 | M63R + L131P + C173R + E328N | L52F + A108V + R354K and/or G284L/S + H287D + E289A |
| DS54 | M63R + L131P + C173R | L52F + A108V + R354K and/or G284L/S + H287D + E289A |
| DS55 | M63R + L131P + C173G + R207L + D250V + R325P + E328L | L52F + A108V + R354K and/or G284L/S + H287D + E289A |
| DS56 | M63R + L131P + C173G + R207L + D250V + R325P + E328N | L52F + A108V + R354K and/or G284L/S + H287D + E289A |
| DS57 | M63R + L131P + C173G + R207L + D250V + R325P | L52F + A108V + R354K and/or G284L/S + H287D + E289A |
| DS58 | M63R + L131P + C173G + R207L + D250V + R325A + E328L | L52F + A108V + R354K and/or G284L/S + H287D + E289A |
| DS59 | M63R + L131P + C173G + R207L + D250V + R325A + E328N | L52F + A108V + R354K and/or G284L/S + H287D + E289A |
| DS60 | M63R + L131P + C173G + R207L + D250V + R325A | L52F + A108V + R354K and/or G284L/S + H287D + E289A |
| DS61 | M63R + L131P + C173G + R207L + D250V + E328L | L52F + A108V + R354K and/or G284L/S + H287D + E289A |
| DS62 | M63R + L131P + C173G + R207L + D250V + E328N | L52F + A108V + R354K and/or G284L/S + H287D + E289A |
| DS63 | M63R + L131P + C173G + R207L + D250V | L52F + A108V + R354K and/or G284L/S + H287D + E289A |
| DS64 | M63R + L131P + C173G + R207L + R325P + E328L | L52F + A108V + R354K and/or G284L/S + H287D + E289A |
| DS65 | M63R + L131P + C173G + R207L + R325P + E328N | L52F + A108V + R354K and/or G284L/S + H287D + E289A |
| DS66 | M63R + L131P + C173G + R207L + R325P | L52F + A108V + R354K and/or G284L/S + H287D + E289A |
| DS67 | M63R + L131P + C173G + R207L + R325A + E328L | L52F + A108V + R354K and/or G284L/S + H287D + E289A |
| DS68 | M63R + L131P + C173G + R207L + R325A + E328N | L52F + A108V + R354K and/or G284L/S + H287D + E289A |
| DS69 | M63R + L131P + C173G + R207L + R325A | L52F + A108V + R354K and/or G284L/S + H287D + E289A |
| DS70 | M63R + L131P + C173G + R207L + E328L | L52F + A108V + R354K and/or G284L/S + H287D + E289A |
| DS71 | M63R + L131P + C173G + R207L + E328N | L52F + A108V + R354K and/or G284L/S + H287D + E289A |
| DS72 | M63R + L131P + C173G + R207L | L52F + A108V + R354K and/or G284L/S + H287D + E289A |
| DS73 | M63R + L131P + C173G + R207N + D250V + R325P + E328L | L52F + A108V + R354K and/or G284L/S + H287D + E289A |
| DS74 | M63R + L131P + C173G + R207N + D250V + R325P + E328N | L52F + A108V + R354K and/or G284L/S + H287D + E289A |
| DS75 | M63R + L131P + C173G + R207N + D250V + R325P | L52F + A108V + R354K and/or G284L/S + H287D + E289A |
| DS76 | M63R + L131P + C173G + R207N + D250V + R325A + E328L | L52F + A108V + R354K and/or G284L/S + H287D + E289A |
| DS77 | M63R + L131P + C173G + R207N + D250V + R325A + E328N | L52F + A108V + R354K and/or G284L/S + H287D + E289A |
| DS78 | M63R + L131P + C173G + R207N + D250V + R325A | L52F + A108V + R354K and/or G284L/S + H287D + E289A |
| DS79 | M63R + L131P + C173G + R207N + D250V + E328L | L52F + A108V + R354K and/or G284L/S + H287D + E289A |
| DS80 | M63R + L131P + C173G + R207N + D250V + E328N | L52F + A108V + R354K and/or G284L/S + H287D + E289A |
| DS81 | M63R + L131P + C173G + R207N + D250V | L52F + A108V + R354K and/or G284L/S + H287D + E289A |
| DS82 | M63R + L131P + C173G + R207N + R325P + E328L | L52F + A108V + R354K and/or G284L/S + H287D + E289A |
| DS83 | M63R + L131P + C173G + R207N + R325P + E328N | L52F + A108V + R354K and/or G284L/S + H287D + E289A |
| DS84 | M63R + L131P + C173G + R207N + R325P | L52F + A108V + R354K and/or G284L/S + H287D + E289A |
| DS85 | M63R + L131P + C173G + R207N + R325A + E328L | L52F + A108V + R354K and/or G284L/S + H287D + E289A |
| DS86 | M63R + L131P + C173G + R207N + R325A + E328N | L52F + A108V + R354K and/or G284L/S + H287D + E289A |
| DS87 | M63R + L131P + C173G + R207N + R325A | L52F + A108V + R354K and/or G284L/S + H287D + E289A |
| DS88 | M63R + L131P + C173G + R207N + E328L | L52F + A108V + R354K and/or G284L/S + H287D + E289A |
| DS89 | M63R + L131P + C173G + R207N + E328N | L52F + A108V + R354K and/or G284L/S + H287D + E289A |
| DS90 | M63R + L131P + C173G + R207N | L52F + A108V + R354K and/or G284L/S + H287D + E289A |
| DS91 | M63R + L131P + C173G + D250V + R325P + E328L | L52F + A108V + R354K and/or G284L/S + H287D + E289A |
| DS92 | M63R + L131P + C173G + D250V + R325P + E328N | L52F + A108V + R354K and/or G284L/S + H287D + E289A |
| DS93 | M63R + L131P + C173G + D250V + R325P | L52F + A108V + R354K and/or G284L/S + H287D + E289A |
| DS94 | M63R + L131P + C173G + D250V + R325A + E328L | L52F + A108V + R354K and/or G284L/S + H287D + E289A |
| DS95 | M63R + L131P + C173G + D250V + R325A + E328N | L52F + A108V + R354K and/or G284L/S + H287D + E289A |
| DS96 | M63R + L131P + C173G + D250V + R325A | L52F + A108V + R354K and/or G284L/S + H287D + E289A |
| DS97 | M63R + L131P + C173G + D250V + E328L | L52F + A108V + R354K and/or G284L/S + H287D + E289A |
| DS98 | M63R + L131P + C173G + D250V + E328N | L52F + A108V + R354K and/or G284L/S + H287D + E289A |
| DS99 | M63R + L131P + C173G + D250V | L52F + A108V + R354K and/or G284L/S + H287D + E289A |
| DS100 | M63R + L131P + C173G + R325P + E328L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS101 | M63R + L131P + C173G + R325P + E328N | L52F + A108V + R354K and/or G284L/S + H287D + E289A |
| DS102 | M63R + L131P + C173G + R325P | L52F + A108V + R354K and/or G284L/S + H287D + E289A |
| DS103 | M63R + L131P + C173G + R325A + E328L | L52F + A108V + R354K and/or G284L/S + H287D + E289A |
| DS104 | M63R + L131P + C173G + R325A + E328N | L52F + A108V + R354K and/or G284L/S + H287D + E289A |
| DS105 | M63R + L131P + C173G + R325A | L52F + A108V + R354K and/or G284L/S + H287D + E289A |
| DS106 | M63R + L131P + C173G + E328L | L52F + A108V + R354K and/or G284L/S + H287D + E289A |
| DS107 | M63R + L131P + C173G + E328N | L52F + A108V + R354K and/or G284L/S + H287D + E289A |
| DS108 | M63R + L131P + C173G | L52F + A108V + R354K and/or G284L/S + H287D + E289A |
| DS163 | M63R + C173R + R207L + D250V + R325P + E328L | L52F + A108V + R354K and/or G284L/S + H287D + E289A |
| DS164 | M63R + C173R + R207L + D250V + R325P + E328N | L52F + A108V + R354K and/or G284L/S + H287D + E289A |
| DS165 | M63R + C173R + R207L + D250V + R325P | L52F + A108V + R354K and/or G284L/S + H287D + E289A |
| DS166 | M63R + C173R + R207L + D250V + R325A + E328L | L52F + A108V + R354K and/or G284L/S + H287D + E289A |
| DS167 | M63R + C173R + R207L + D250V + R325A + E328N | L52F + A108V + R354K and/or G284L/S + H287D + E289A |
| DS168 | M63R + C173R + R207L + D250V + R325A | L52F + A108V + R354K and/or G284L/S + H287D + E289A |
| DS169 | M63R + C173R + R207L + D250V + E328L | L52F + A108V + R354K and/or G284L/S + H287D + E289A |
| DS170 | M63R + C173R + R207L + D250V + E328N | L52F + A108V + R354K and/or G284L/S + H287D + E289A |
| DS171 | M63R + C173R + R207L + D250V | L52F + A108V + R354K and/or G284L/S + H287D + E289A |
| DS172 | M63R + C173R + R207L + R325P + E328L | L52F + A108V + R354K and/or G284L/S + H287D + E289A |
| DS173 | M63R + C173R + R207L + R325P + E328N | L52F + A108V + R354K and/or G284L/S + H287D + E289A |
| DS174 | M63R + C173R + R207L + R325P | L52F + A108V + R354K and/or G284L/S + H287D + E289A |
| DS175 | M63R + C173R + R207L + R325A + E328L | L52F + A108V + R354K and/or G284L/S + H287D + E289A |
| DS176 | M63R + C173R + R207L + R325A + E328N | L52F + A108V + R354K and/or G284L/S + H287D + E289A |
| DS177 | M63R + C173R + R207L + R325A | L52F + A108V + R354K and/or G284L/S + H287D + E289A |
| DS178 | M63R + C173R + R207L + E328L | L52F + A108V + R354K and/or G284L/S + H287D + E289A |
| DS179 | M63R + C173R + R207L + E328N | L52F + A108V + R354K and/or G284L/S + H287D + E289A |
| DS180 | M63R + C173R + R207L | L52F + A108V + R354K and/or G284L/S + H287D + E289A |
| DS52 | M63R + C173R + R207N + D250V + R325P + E328L | L52F + A108V + R354K and/or G284L/S + H287D + E289A |
| DS182 | M63R + C173R + R207N + D250V + R325P + E328N | L52F + A108V + R354K and/or G284L/S + H287D + E289A |
| DS183 | M63R + C173R + R207N + D250V + R325P | L52F + A108V + R354K and/or G284L/S + H287D + E289A |
| DS184 | M63R + C173R + R207N + D250V + R325A + E328L | L52F + A108V + R354K and/or G284L/S + H287D + E289A |
| DS185 | M63R + C173R + R207N + D250V + R325A + E328N | L52F + A108V + R354K and/or G284L/S + H287D + E289A |
| DS186 | M63R + C173R + R207N + D250V + R325A | L52F + A108V + R354K and/or G284L/S + H287D + E289A |
| DS187 | M63R + C173R + R207N + D250V + E328L | L52F + A108V + R354K and/or G284L/S + H287D + E289A |
| DS188 | M63R + C173R + R207N + D250V + E328N | L52F + A108V + R354K and/or G284L/S + H287D + E289A |
| DS189 | M63R + C173R + R207N + D250V | L52F + A108V + R354K and/or G284L/S + H287D + E289A |
| DS190 | M63R + C173R + R207N + R325P + E328L | L52F + A108V + R354K and/or G284L/S + H287D + E289A |
| DS191 | M63R + C173R + R207N + R325P + E328N | L52F + A108V + R354K and/or G284L/S + H287D + E289A |
| DS63 | M63R + C173R + R207N + R325P | L52F + A108V + R354K and/or G284L/S + H287D + E289A |
| DS193 | M63R + C173R + R207N + R325A + E328L | L52F + A108V + R354K and/or G284L/S + H287D + E289A |
| DS194 | M63R + C173R + R207N + R325A + E328N | L52F + A108V + R354K and/or G284L/S + H287D + E289A |
| DS195 | M63R + C173R + R207N + R325A | L52F + A108V + R354K and/or G284L/S + H287D + E289A |
| DS196 | M63R + C173R + R207N + E328L | L52F + A108V + R354K and/or G284L/S + H287D + E289A |
| DS197 | M63R + C173R + R207N + E328N | L52F + A108V + R354K and/or G284L/S + H287D + E289A |
| DS198 | M63R + C173R + R207N | L52F + A108V + R354K and/or G284L/S + H287D + E289A |
| DS199 | M63R + C173R + D250V + R325P + E328L | L52F + A108V + R354K and/or G284L/S + H287D + E289A |
| DS200 | M63R + C173R + D250V + R325P + E328N | L52F + A108V + R354K and/or G284L/S + H287D + E289A |
| DS201 | M63R + C173R + D250V + R325P | L52F + A108V + R354K and/or G284L/S + H287D + E289A |
| DS202 | M63R + C173R + D250V + R325A + E328L | L52F + A108V + R354K and/or G284L/S + H287D + E289A |
| DS203 | M63R + C173R + D250V + R325A + E328N | L52F + A108V + R354K and/or G284L/S + H287D + E289A |
| DS204 | M63R + C173R + D250V + R325A | L52F + A108V + R354K and/or G284L/S + H287D + E289A |
| DS205 | M63R + C173R + D250V + E328L | L52F + A108V + R354K and/or G284L/S + H287D + E289A |
| DS206 | M63R + C173R + D250V + E328N | L52F + A108V + R354K and/or G284L/S + H287D + E289A |
| DS207 | M63R + C173R + D250V | L52F + A108V + R354K and/or G284L/S + H287D + E289A |
| DS208 | M63R + C173R + R325P + E328L | L52F + A108V + R354K and/or G284L/S + H287D + E289A |
| DS209 | M63R + C173R + R325P + E328N | L52F + A108V + R354K and/or G284L/S + H287D + E289A |
| DS210 | M63R + C173R + R325P | L52F + A108V + R354K and/or G284L/S + H287D + E289A |
| DS211 | M63R + C173R + R325A + E328L | L52F + A108V + R354K and/or G284L/S + H287D + E289A |
| DS212 | M63R + C173R + R325A + E328N | L52F + A108V + R354K and/or G284L/S + H287D + E289A |
| DS213 | M63R + C173R + R325A | L52F + A108V + R354K and/or G284L/S + H287D + E289A |
| DS214 | M63R + C173R + E328L | L52F + A108V + R354K and/or G284L/S + H287D + E289A |
| DS215 | M63R + C173R + E328N | L52F + A108V + R354K and/or G284L/S + H287D + E289A |
| DS216 | M63R + C173R | L52F + A108V + R354K and/or G284L/S + H287D + E289A |
| DS217 | M63R + C173G + R207L + D250V + R325P + E328L | L52F + A108V + R354K and/or G284L/S + H287D + E289A |
| DS218 | M63R + C173G + R207L + D250V + R325P + E328N | L52F + A108V + R354K and/or G284L/S + H287D + E289A |
| DS219 | M63R + C173G + R207L + D250V + R325P | L52F + A108V + R354K and/or G284L/S + H287D + E289A |
| DS220 | M63R + C173G + R207L + D250V + R325A + E328L | L52F + A108V + R354K and/or G284L/S + H287D + E289A |
| DS221 | M63R + C173G + R207L + D250V + R325A + E328N | L52F + A108V + R354K and/or G284L/S + H287D + E289A |
| DS222 | M63R + C173G + R207L + D250V + R325A | L52F + A108V + R354K and/or G284L/S + H287D + E289A |
| DS223 | M63R + C173G + R207L + D250V + E328L | L52F + A108V + R354K and/or G284L/S + H287D + E289A |
| DS224 | M63R + C173G + R207L + D250V + E328N | L52F + A108V + R354K and/or G284L/S + H287D + E289A |
| DS225 | M63R + C173G + R207L + D250V | L52F + A108V + R354K and/or G284L/S + H287D + E289A |
| DS226 | M63R + C173G + R207L + R325P + E328L | L52F + A108V + R354K and/or G284L/S + H287D + E289A |
| DS227 | M63R + C173G + R207L + R325P + E328N | L52F + A108V + R354K and/or G284L/S + H287D + E289A |
| DS228 | M63R + C173G + R207L + R325P | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS229 | M63R + C173G + R207L + R325A + E328L | L52F + A108V + R354K and/or G284L/S + H287D + E289A |
| DS230 | M63R + C173G + R207L + R325A + E328N | L52F + A108V + R354K and/or G284L/S + H287D + E289A |
| DS231 | M63R + C173G + R207L + R325A | L52F + A108V + R354K and/or G284L/S + H287D + E289A |
| DS232 | M63R + C173G + R207L + E328L | L52F + A108V + R354K and/or G284L/S + H287D + E289A |
| DS233 | M63R + C173G + R207L + E328N | L52F + A108V + R354K and/or G284L/S + H287D + E289A |
| DS234 | M63R + C173G + R207L | L52F + A108V + R354K and/or G284L/S + H287D + E289A |
| DS235 | M63R + C173G + R207N + D250V + R325P + E328L | L52F + A108V + R354K and/or G284L/S + H287D + E289A |
| DS236 | M63R + C173G + R207N + D250V + R325P + E328N | L52F + A108V + R354K and/or G284L/S + H287D + E289A |
| DS108 | M63R + C173G + R207N + D250V + R325P | L52F + A108V + R354K and/or G284L/S + H287D + E289A |
| DS238 | M63R + C173G + R207N + D250V + R325A + E328L | L52F + A108V + R354K and/or G284L/S + H287D + E289A |
| DS239 | M63R + C173G + R207N + D250V + R325A + E328N | L52F + A108V + R354K and/or G284L/S + H287D + E289A |
| DS240 | M63R + C173G + R207N + D250V + R325A | L52F + A108V + R354K and/or G284L/S + H287D + E289A |
| DS241 | M63R + C173G + R207N + D250V + E328L | L52F + A108V + R354K and/or G284L/S + H287D + E289A |
| DS242 | M63R + C173G + R207N + D250V + E328N | L52F + A108V + R354K and/or G284L/S + H287D + E289A |
| DS243 | M63R + C173G + R207N + D250V | L52F + A108V + R354K and/or G284L/S + H287D + E289A |
| DS244 | M63R + C173G + R207N + R325P + E328L | L52F + A108V + R354K and/or G284L/S + H287D + E289A |
| DS245 | M63R + C173G + R207N + R325P + E328N | L52F + A108V + R354K and/or G284L/S + H287D + E289A |
| DS246 | M63R + C173G + R207N + R325P | L52F + A108V + R354K and/or G284L/S + H287D + E289A |
| DS247 | M63R + C173G + R207N + R325A + E328L | L52F + A108V + R354K and/or G284L/S + H287D + E289A |
| DS248 | M63R + C173G + R207N + R325A + E328N | L52F + A108V + R354K and/or G284L/S + H287D + E289A |
| DS249 | M63R + C173G + R207N + R325A | L52F + A108V + R354K and/or G284L/S + H287D + E289A |
| DS250 | M63R + C173G + R207N + E328L | L52F + A108V + R354K and/or G284L/S + H287D + E289A |
| DS251 | M63R + C173G + R207N + E328N | L52F + A108V + R354K and/or G284L/S + H287D + E289A |
| DS252 | M63R + C173G + R207N | L52F + A108V + R354K and/or G284L/S + H287D + E289A |
| DS253 | M63R + C173G + D250V + R325P + E328L | L52F + A108V + R354K and/or G284L/S + H287D + E289A |
| DS254 | M63R + C173G + D250V + R325P + E328N | L52F + A108V + R354K and/or G284L/S + H287D + E289A |
| DS255 | M63R + C173G + D250V + R325P | L52F + A108V + R354K and/or G284L/S + H287D + E289A |
| DS256 | M63R + C173G + D250V + R325A + E328L | L52F + A108V + R354K and/or G284L/S + H287D + E289A |
| DS257 | M63R + C173G + D250V + R325A + E328N | L52F + A108V + R354K and/or G284L/S + H287D + E289A |
| DS258 | M63R + C173G + D250V + R325A | L52F + A108V + R354K and/or G284L/S + H287D + E289A |
| DS259 | M63R + C173G + D250V + E328L | L52F + A108V + R354K and/or G284L/S + H287D + E289A |
| DS131 | M63R + C173G + D250V + E328N | L52F + A108V + R354K and/or G284L/S + H287D + E289A |
| DS261 | M63R + C173G + D250V | L52F + A108V + R354K and/or G284L/S + H287D + E289A |
| DS262 | M63R + C173G + R325P + E328L | L52F + A108V + R354K and/or G284L/S + H287D + E289A |
| DS263 | M63R + C173G + R325P + E328N | L52F + A108V + R354K and/or G284L/S + H287D + E289A |
| DS264 | M63R + C173G + R325P | L52F + A108V + R354K and/or G284L/S + H287D + E289A |
| DS265 | M63R + C173G + R325A + E328L | L52F + A108V + R354K and/or G284L/S + H287D + E289A |
| DS266 | M63R + C173G + R325A + E328N | L52F + A108V + R354K and/or G284L/S + H287D + E289A |
| DS267 | M63R + C173G + R325A | L52F + A108V + R354K and/or G284L/S + H287D + E289A |
| DS268 | M63R + C173G + E328L | L52F + A108V + R354K and/or G284L/S + H287D + E289A |
| DS269 | M63R + C173G + E328N | L52F + A108V + R354K and/or G284L/S + H287D + E289A |
| DS270 | M63R + C173G | L52F + A108V + R354K and/or G284L/S + H287D + E289A |
| DS325 | M63Q + L131P + C173R + R207L + D250V + R325P + E328L | L52F + A108V + R354K and/or G284L/S + H287D + E289A |
| DS326 | M63Q + L131P + C173R + R207L + D250V + R325P + E328N | L52F + A108V + R354K and/or G284L/S + H287D + E289A |
| DS327 | M63Q + L131P + C173R + R207L + D250V + R325P | L52F + A108V + R354K and/or G284L/S + H287D + E289A |
| DS328 | M63Q + L131P + C173R + R207L + D250V + R325A + E328L | L52F + A108V + R354K and/or G284L/S + H287D + E289A |
| DS329 | M63Q + L131P + C173R + R207L + D250V + R325A + E328N | L52F + A108V + R354K and/or G284L/S + H287D + E289A |
| DS330 | M63Q + L131P + C173R + R207L + D250V + R325A | L52F + A108V + R354K and/or G284L/S + H287D + E289A |
| DS331 | M63Q + L131P + C173R + R207L + D250V + E328L | L52F + A108V + R354K and/or G284L/S + H287D + E289A |
| DS332 | M63Q + L131P + C173R + R207L + D250V + E328N | L52F + A108V + R354K and/or G284L/S + H287D + E289A |
| DS333 | M63Q + L131P + C173R + R207L + D250V | L52F + A108V + R354K and/or G284L/S + H287D + E289A |
| DS334 | M63Q + L131P + C173R + R207L + R325P + E328L | L52F + A108V + R354K and/or G284L/S + H287D + E289A |
| DS335 | M63Q + L131P + C173R + R207L + R325P + E328N | L52F + A108V + R354K and/or G284L/S + H287D + E289A |
| DS207 | M63Q + L131P + C173R + R207L + R325P | L52F + A108V + R354K and/or G284L/S + H287D + E289A |
| DS337 | M63Q + L131P + C173R + R207L + R325A + E328L | L52F + A108V + R354K and/or G284L/S + H287D + E289A |
| DS338 | M63Q + L131P + C173R + R207L + R325A + E328N | L52F + A108V + R354K and/or G284L/S + H287D + E289A |
| DS339 | M63Q + L131P + C173R + R207L + R325A | L52F + A108V + R354K and/or G284L/S + H287D + E289A |
| DS340 | M63Q + L131P + C173R + R207L + E328L | L52F + A108V + R354K and/or G284L/S + H287D + E289A |
| DS341 | M63Q + L131P + C173R + R207L + E328N | L52F + A108V + R354K and/or G284L/S + H287D + E289A |
| DS342 | M63Q + L131P + C173R + R207L | L52F + A108V + R354K and/or G284L/S + H287D + E289A |
| DS343 | M63Q + L131P + C173R + R207N + D250V + R325P + E328L | L52F + A108V + R354K and/or G284L/S + H287D + E289A |
| DS344 | M63Q + L131P + C173R + R207N + D250V + R325P + E328N | L52F + A108V + R354K and/or G284L/S + H287D + E289A |
| DS345 | M63Q + L131P + C173R + R207N + D250V + R325P | L52F + A108V + R354K and/or G284L/S + H287D + E289A |
| DS346 | M63Q + L131P + C173R + R207N + D250V + R325A + E328L | L52F + A108V + R354K and/or G284L/S + H287D + E289A |
| DS347 | M63Q + L131P + C173R + R207N + D250V + R325A + E328N | L52F + A108V + R354K and/or G284L/S + H287D + E289A |
| DS348 | M63Q + L131P + C173R + R207N + D250V + R325A | L52F + A108V + R354K and/or G284L/S + H287D + E289A |
| DS349 | M63Q + L131P + C173R + R207N + D250V + E328L | L52F + A108V + R354K and/or G284L/S + H287D + E289A |
| DS350 | M63Q + L131P + C173R + R207N + D250V + E328N | L52F + A108V + R354K and/or G284L/S + H287D + E289A |
| DS351 | M63Q + L131P + C173R + R207N + D250V | L52F + A108V + R354K and/or G284L/S + H287D + E289A |
| DS352 | M63Q + L131P + C173R + R207N + R325P + E328L | L52F + A108V + R354K and/or G284L/S + H287D + E289A |
| DS353 | M63Q + L131P + C173R + R207N + R325P + E328N | L52F + A108V + R354K and/or G284L/S + H287D + E289A |
| DS354 | M63Q + L131P + C173R + R207N + R325P | L52F + A108V + R354K and/or G284L/S + H287D + E289A |
| DS355 | M63Q + L131P + C173R + R207N + R325A + E328L | L52F + A108V + R354K and/or G284L/S + H287D + E289A |
| DS356 | M63Q + L131P + C173R + R207N + R325A + E328N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS357 | M63Q + L131P + C173R + R207N + R325A | L52F + A108V + R354K and/or G284L/S + H287D + E289A |
| DS358 | M63Q + L131P + C173R + R207N + E328L | L52F + A108V + R354K and/or G284L/S + H287D + E289A |
| DS359 | M63Q + L131P + C173R + R207N + E328N | L52F + A108V + R354K and/or G284L/S + H287D + E289A |
| DS360 | M63Q + L131P + C173R + R207N | L52F + A108V + R354K and/or G284L/S + H287D + E289A |
| DS361 | M63Q + L131P + C173R + D250V + R325P + E328L | L52F + A108V + R354K and/or G284L/S + H287D + E289A |
| DS362 | M63Q + L131P + C173R + D250V + R325P + E328N | L52F + A108V + R354K and/or G284L/S + H287D + E289A |
| DS363 | M63Q + L131P + C173R + D250V + R325P | L52F + A108V + R354K and/or G284L/S + H287D + E289A |
| DS364 | M63Q + L131P + C173R + D250V + R325A + E328L | L52F + A108V + R354K and/or G284L/S + H287D + E289A |
| DS365 | M63Q + L131P + C173R + D250V + R325A + E328N | L52F + A108V + R354K and/or G284L/S + H287D + E289A |
| DS366 | M63Q + L131P + C173R + D250V + R325A | L52F + A108V + R354K and/or G284L/S + H287D + E289A |
| DS367 | M63Q + L131P + C173R + D250V + E328L | L52F + A108V + R354K and/or G284L/S + H287D + E289A |
| DS368 | M63Q + L131P + C173R + D250V + E328N | L52F + A108V + R354K and/or G284L/S + H287D + E289A |
| DS369 | M63Q + L131P + C173R + D250V | L52F + A108V + R354K and/or G284L/S + H287D + E289A |
| DS370 | M63Q + L131P + C173R + R325P + E328L | L52F + A108V + R354K and/or G284L/S + H287D + E289A |
| DS371 | M63Q + L131P + C173R + R325P + E328N | L52F + A108V + R354K and/or G284L/S + H287D + E289A |
| DS372 | M63Q + L131P + C173R + R325P | L52F + A108V + R354K and/or G284L/S + H287D + E289A |
| DS373 | M63Q + L131P + C173R + R325A + E328L | L52F + A108V + R354K and/or G284L/S + H287D + E289A |
| DS374 | M63Q + L131P + C173R + R325A + E328N | L52F + A108V + R354K and/or G284L/S + H287D + E289A |
| DS375 | M63Q + L131P + C173R + R325A | L52F + A108V + R354K and/or G284L/S + H287D + E289A |
| DS376 | M63Q + L131P + C173R + E328L | L52F + A108V + R354K and/or G284L/S + H287D + E289A |
| DS377 | M63Q + L131P + C173R + E328N | L52F + A108V + R354K and/or G284L/S + H287D + E289A |
| DS378 | M63Q + L131P + C173R | L52F + A108V + R354K and/or G284L/S + H287D + E289A |
| DS250 | M63Q + L131P + C173G + R207L + D250V + R325P + E328L | L52F + A108V + R354K and/or G284L/S + H287D + E289A |
| DS380 | M63Q + L131P + C173G + R207L + D250V + R325P + E328N | L52F + A108V + R354K and/or G284L/S + H287D + E289A |
| DS381 | M63Q + L131P + C173G + R207L + D250V + R325P | L52F + A108V + R354K and/or G284L/S + H287D + E289A |
| DS382 | M63Q + L131P + C173G + R207L + D250V + R325A + E328L | L52F + A108V + R354K and/or G284L/S + H287D + E289A |
| DS383 | M63Q + L131P + C173G + R207L + D250V + R325A + E328N | L52F + A108V + R354K and/or G284L/S + H287D + E289A |
| DS384 | M63Q + L131P + C173G + R207L + D250V + R325A | L52F + A108V + R354K and/or G284L/S + H287D + E289A |
| DS385 | M63Q + L131P + C173G + R207L + D250V + E328L | L52F + A108V + R354K and/or G284L/S + H287D + E289A |
| DS386 | M63Q + L131P + C173G + R207L + D250V + E328N | L52F + A108V + R354K and/or G284L/S + H287D + E289A |
| DS387 | M63Q + L131P + C173G + R207L + D250V | L52F + A108V + R354K and/or G284L/S + H287D + E289A |
| DS388 | M63Q + L131P + C173G + R207L + R325P + E328L | L52F + A108V + R354K and/or G284L/S + H287D + E289A |
| DS389 | M63Q + L131P + C173G + R207L + R325P + E328N | L52F + A108V + R354K and/or G284L/S + H287D + E289A |
| DS390 | M63Q + L131P + C173G + R207L + R325P | L52F + A108V + R354K and/or G284L/S + H287D + E289A |
| DS391 | M63Q + L131P + C173G + R207L + R325A + E328L | L52F + A108V + R354K and/or G284L/S + H287D + E289A |
| DS392 | M63Q + L131P + C173G + R207L + R325A + E328N | L52F + A108V + R354K and/or G284L/S + H287D + E289A |
| DS393 | M63Q + L131P + C173G + R207L + R325A | L52F + A108V + R354K and/or G284L/S + H287D + E289A |
| DS394 | M63Q + L131P + C173G + R207L + E328L | L52F + A108V + R354K and/or G284L/S + H287D + E289A |
| DS395 | M63Q + L131P + C173G + R207L + E328N | L52F + A108V + R354K and/or G284L/S + H287D + E289A |
| DS396 | M63Q + L131P + C173G + R207L | L52F + A108V + R354K and/or G284L/S + H287D + E289A |
| DS397 | M63Q + L131P + C173G + R207N + D250V + R325P + E328L | L52F + A108V + R354K and/or G284L/S + H287D + E289A |
| DS398 | M63Q + L131P + C173G + R207N + D250V + R325P + E328N | L52F + A108V + R354K and/or G284L/S + H287D + E289A |
| DS399 | M63Q + L131P + C173G + R207N + D250V + R325P | L52F + A108V + R354K and/or G284L/S + H287D + E289A |
| DS400 | M63Q + L131P + C173G + R207N + D250V + R325A + E328L | L52F + A108V + R354K and/or G284L/S + H287D + E289A |
| DS401 | M63Q + L131P + C173G + R207N + D250V + R325A + E328N | L52F + A108V + R354K and/or G284L/S + H287D + E289A |
| DS402 | M63Q + L131P + C173G + R207N + D250V + R325A | L52F + A108V + R354K and/or G284L/S + H287D + E289A |
| DS403 | M63Q + L131P + C173G + R207N + D250V + E328L | L52F + A108V + R354K and/or G284L/S + H287D + E289A |
| DS404 | M63Q + L131P + C173G + R207N + D250V + E328N | L52F + A108V + R354K and/or G284L/S + H287D + E289A |
| DS405 | M63Q + L131P + C173G + R207N + D250V | L52F + A108V + R354K and/or G284L/S + H287D + E289A |
| DS406 | M63Q + L131P + C173G + R207N + R325P + E328L | L52F + A108V + R354K and/or G284L/S + H287D + E289A |
| DS407 | M63Q + L131P + C173G + R207N + R325P + E328N | L52F + A108V + R354K and/or G284L/S + H287D + E289A |
| DS408 | M63Q + L131P + C173G + R207N + R325P | L52F + A108V + R354K and/or G284L/S + H287D + E289A |
| DS409 | M63Q + L131P + C173G + R207N + R325A + E328L | L52F + A108V + R354K and/or G284L/S + H287D + E289A |
| DS410 | M63Q + L131P + C173G + R207N + R325A + E328N | L52F + A108V + R354K and/or G284L/S + H287D + E289A |
| DS411 | M63Q + L131P + C173G + R207N + R325A | L52F + A108V + R354K and/or G284L/S + H287D + E289A |
| DS412 | M63Q + L131P + C173G + R207N + E328L | L52F + A108V + R354K and/or G284L/S + H287D + E289A |
| DS284 | M63Q + L131P + C173G + R207N + E328N | L52F + A108V + R354K and/or G284L/S + H287D + E289A |
| DS414 | M63Q + L131P + C173G + R207N | L52F + A108V + R354K and/or G284L/S + H287D + E289A |
| DS415 | M63Q + L131P + C173G + D250V + R325P + E328L | L52F + A108V + R354K and/or G284L/S + H287D + E289A |
| DS287 | M63Q + L131P + C173G + D250V + R325P + E328N | L52F + A108V + R354K and/or G284L/S + H287D + E289A |
| DS417 | M63Q + L131P + C173G + D250V + R325P | L52F + A108V + R354K and/or G284L/S + H287D + E289A |
| DS289 | M63Q + L131P + C173G + D250V + R325A + E328L | L52F + A108V + R354K and/or G284L/S + H287D + E289A |
| DS419 | M63Q + L131P + C173G + D250V + R325A + E328N | L52F + A108V + R354K and/or G284L/S + H287D + E289A |
| DS420 | M63Q + L131P + C173G + D250V + R325A | L52F + A108V + R354K and/or G284L/S + H287D + E289A |
| DS421 | M63Q + L131P + C173G + D250V + E328L | L52F + A108V + R354K and/or G284L/S + H287D + E289A |
| DS422 | M63Q + L131P + C173G + D250V + E328N | L52F + A108V + R354K and/or G284L/S + H287D + E289A |
| DS423 | M63Q + L131P + C173G + D250V | L52F + A108V + R354K and/or G284L/S + H287D + E289A |
| DS424 | M63Q + L131P + C173G + R325P + E328L | L52F + A108V + R354K and/or G284L/S + H287D + E289A |
| DS425 | M63Q + L131P + C173G + R325P + E328N | L52F + A108V + R354K and/or G284L/S + H287D + E289A |
| DS426 | M63Q + L131P + C173G + R325P | L52F + A108V + R354K and/or G284L/S + H287D + E289A |
| DS427 | M63Q + L131P + C173G + R325A + E328L | L52F + A108V + R354K and/or G284L/S + H287D + E289A |
| DS428 | M63Q + L131P + C173G + R325A + E328N | L52F + A108V + R354K and/or G284L/S + H287D + E289A |
| DS429 | M63Q + L131P + C173G + R325A | L52F + A108V + R354K and/or G284L/S + H287D + E289A |
| DS430 | M63Q + L131P + C173G + E328L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS431 | M63Q + L131P + C173G + E328N | L52F + A108V + R354K and/or G284L/S + H287D + E289A |
| DS432 | M63Q + L131P + C173G | L52F + A108V + R354K and/or G284L/S + H287D + E289A |
| DS487 | M63Q + C173R + R207L + D250V + R325P + E328L | L52F + A108V + R354K and/or G284L/S + H287D + E289A |
| DS488 | M63Q + C173R + R207L + D250V + R325P + E328N | L52F + A108V + R354K and/or G284L/S + H287D + E289A |
| DS489 | M63Q + C173R + R207L + D250V + R325P | L52F + A108V + R354K and/or G284L/S + H287D + E289A |
| DS490 | M63Q + C173R + R207L + D250V + R325A + E328L | L52F + A108V + R354K and/or G284L/S + H287D + E289A |
| DS491 | M63Q + C173R + R207L + D250V + R325A + E328N | L52F + A108V + R354K and/or G284L/S + H287D + E289A |
| DS492 | M63Q + C173R + R207L + D250V + R325A | L52F + A108V + R354K and/or G284L/S + H287D + E289A |
| DS493 | M63Q + C173R + R207L + D250V + E328L | L52F + A108V + R354K and/or G284L/S + H287D + E289A |
| DS494 | M63Q + C173R + R207L + D250V + E328N | L52F + A108V + R354K and/or G284L/S + H287D + E289A |
| DS495 | M63Q + C173R + R207L + D250V | L52F + A108V + R354K and/or G284L/S + H287D + E289A |
| DS496 | M63Q + C173R + R207L + R325P + E328L | L52F + A108V + R354K and/or G284L/S + H287D + E289A |
| DS497 | M63Q + C173R + R207L + R325P + E328N | L52F + A108V + R354K and/or G284L/S + H287D + E289A |
| DS498 | M63Q + C173R + R207L + R325P | L52F + A108V + R354K and/or G284L/S + H287D + E289A |
| DS499 | M63Q + C173R + R207L + R325A + E328L | L52F + A108V + R354K and/or G284L/S + H287D + E289A |
| DS500 | M63Q + C173R + R207L + R325A + E328N | L52F + A108V + R354K and/or G284L/S + H287D + E289A |
| DS501 | M63Q + C173R + R207L + R325A | L52F + A108V + R354K and/or G284L/S + H287D + E289A |
| DS502 | M63Q + C173R + R207L + E328L | L52F + A108V + R354K and/or G284L/S + H287D + E289A |
| DS503 | M63Q + C173R + R207L + E328N | L52F + A108V + R354K and/or G284L/S + H287D + E289A |
| DS504 | M63Q + C173R + R207L | L52F + A108V + R354K and/or G284L/S + H287D + E289A |
| DS505 | M63Q + C173R + R207N + D250V + R325P + E328L | L52F + A108V + R354K and/or G284L/S + H287D + E289A |
| DS506 | M63Q + C173R + R207N + D250V + R325P + E328N | L52F + A108V + R354K and/or G284L/S + H287D + E289A |
| DS507 | M63Q + C173R + R207N + D250V + R325P | L52F + A108V + R354K and/or G284L/S + H287D + E289A |
| DS508 | M63Q + C173R + R207N + D250V + R325A + E328L | L52F + A108V + R354K and/or G284L/S + H287D + E289A |
| DS509 | M63Q + C173R + R207N + D250V + R325A + E328N | L52F + A108V + R354K and/or G284L/S + H287D + E289A |
| DS510 | M63Q + C173R + R207N + D250V + R325A | L52F + A108V + R354K and/or G284L/S + H287D + E289A |
| DS511 | M63Q + C173R + R207N + D250V + E328L | L52F + A108V + R354K and/or G284L/S + H287D + E289A |
| DS512 | M63Q + C173R + R207N + D250V + E328N | L52F + A108V + R354K and/or G284L/S + H287D + E289A |
| DS513 | M63Q + C173R + R207N + D250V | L52F + A108V + R354K and/or G284L/S + H287D + E289A |
| DS514 | M63Q + C173R + R207N + R325P + E328L | L52F + A108V + R354K and/or G284L/S + H287D + E289A |
| DS515 | M63Q + C173R + R207N + R325P + E328N | L52F + A108V + R354K and/or G284L/S + H287D + E289A |
| DS516 | M63Q + C173R + R207N + R325P | L52F + A108V + R354K and/or G284L/S + H287D + E289A |
| DS517 | M63Q + C173R + R207N + R325A + E328L | L52F + A108V + R354K and/or G284L/S + H287D + E289A |
| DS518 | M63Q + C173R + R207N + R325A + E328N | L52F + A108V + R354K and/or G284L/S + H287D + E289A |
| DS519 | M63Q + C173R + R207N + R325A | L52F + A108V + R354K and/or G284L/S + H287D + E289A |
| DS520 | M63Q + C173R + R207N + E328L | L52F + A108V + R354K and/or G284L/S + H287D + E289A |
| DS521 | M63Q + C173R + R207N + E328N | L52F + A108V + R354K and/or G284L/S + H287D + E289A |
| DS522 | M63Q + C173R + R207N | L52F + A108V + R354K and/or G284L/S + H287D + E289A |
| DS523 | M63Q + C173R + D250V + R325P + E328L | L52F + A108V + R354K and/or G284L/S + H287D + E289A |
| DS524 | M63Q + C173R + D250V + R325P + E328N | L52F + A108V + R354K and/or G284L/S + H287D + E289A |
| DS525 | M63Q + C173R + D250V + R325P | L52F + A108V + R354K and/or G284L/S + H287D + E289A |
| DS526 | M63Q + C173R + D250V + R325A + E328L | L52F + A108V + R354K and/or G284L/S + H287D + E289A |
| DS527 | M63Q + C173R + D250V + R325A + E328N | L52F + A108V + R354K and/or G284L/S + H287D + E289A |
| DS528 | M63Q + C173R + D250V + R325A | L52F + A108V + R354K and/or G284L/S + H287D + E289A |
| DS529 | M63Q + C173R + D250V + E328L | L52F + A108V + R354K and/or G284L/S + H287D + E289A |
| DS530 | M63Q + C173R + D250V + E328N | L52F + A108V + R354K and/or G284L/S + H287D + E289A |
| DS531 | M63Q + C173R + D250V | L52F + A108V + R354K and/or G284L/S + H287D + E289A |
| DS532 | M63Q + C173R + R325P + E328L | L52F + A108V + R354K and/or G284L/S + H287D + E289A |
| DS533 | M63Q + C173R + R325P + E328N | L52F + A108V + R354K and/or G284L/S + H287D + E289A |
| DS534 | M63Q + C173R + R325P | L52F + A108V + R354K and/or G284L/S + H287D + E289A |
| DS535 | M63Q + C173R + R325A + E328L | L52F + A108V + R354K and/or G284L/S + H287D + E289A |
| DS536 | M63Q + C173R + R325A + E328N | L52F + A108V + R354K and/or G284L/S + H287D + E289A |
| DS537 | M63Q + C173R + R325A | L52F + A108V + R354K and/or G284L/S + H287D + E289A |
| DS538 | M63Q + C173R + E328L | L52F + A108V + R354K and/or G284L/S + H287D + E289A |
| DS539 | M63Q + C173R + E328N | L52F + A108V + R354K and/or G284L/S + H287D + E289A |
| DS540 | M63Q + C173R | L52F + A108V + R354K and/or G284L/S + H287D + E289A |
| DS541 | M63Q + C173G + R207L + D250V + R325P + E328L | L52F + A108V + R354K and/or G284L/S + H287D + E289A |
| DS542 | M63Q + C173G + R207L + D250V + R325P + E328N | L52F + A108V + R354K and/or G284L/S + H287D + E289A |
| DS543 | M63Q + C173G + R207L + D250V + R325P | L52F + A108V + R354K and/or G284L/S + H287D + E289A |
| DS544 | M63Q + C173G + R207L + D250V + R325A + E328L | L52F + A108V + R354K and/or G284L/S + H287D + E289A |
| DS545 | M63Q + C173G + R207L + D250V + R325A + E328N | L52F + A108V + R354K and/or G284L/S + H287D + E289A |
| DS546 | M63Q + C173G + R207L + D250V + R325A | L52F + A108V + R354K and/or G284L/S + H287D + E289A |
| DS547 | M63Q + C173G + R207L + D250V + E328L | L52F + A108V + R354K and/or G284L/S + H287D + E289A |
| DS548 | M63Q + C173G + R207L + D250V + E328N | L52F + A108V + R354K and/or G284L/S + H287D + E289A |
| DS549 | M63Q + C173G + R207L + D250V | L52F + A108V + R354K and/or G284L/S + H287D + E289A |
| DS550 | M63Q + C173G + R207L + R325P + E328L | L52F + A108V + R354K and/or G284L/S + H287D + E289A |
| DS551 | M63Q + C173G + R207L + R325P + E328N | L52F + A108V + R354K and/or G284L/S + H287D + E289A |
| DS552 | M63Q + C173G + R207L + R325P | L52F + A108V + R354K and/or G284L/S + H287D + E289A |
| DS553 | M63Q + C173G + R207L + R325A + E328L | L52F + A108V + R354K and/or G284L/S + H287D + E289A |
| DS554 | M63Q + C173G + R207L + R325A + E328N | L52F + A108V + R354K and/or G284L/S + H287D + E289A |
| DS555 | M63Q + C173G + R207L + R325A | L52F + A108V + R354K and/or G284L/S + H287D + E289A |
| DS556 | M63Q + C173G + R207L + E328L | L52F + A108V + R354K and/or G284L/S + H287D + E289A |
| DS557 | M63Q + C173G + R207L + E328N | L52F + A108V + R354K and/or G284L/S + H287D + E289A |
| DS558 | M63Q + C173G + R207L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS559 | M63Q + C173G + R207N + D250V + R325P + E328L | L52F + A108V + R354K and/or G284L/S + H287D + E289A |
| DS560 | M63Q + C173G + R207N + D250V + R325P + E328N | L52F + A108V + R354K and/or G284L/S + H287D + E289A |
| DS561 | M63Q + C173G + R207N + D250V + R325P | L52F + A108V + R354K and/or G284L/S + H287D + E289A |
| DS562 | M63Q + C173G + R207N + D250V + R325A + E328L | L52F + A108V + R354K and/or G284L/S + H287D + E289A |
| DS563 | M63Q + C173G + R207N + D250V + R325A + E328N | L52F + A108V + R354K and/or G284L/S + H287D + E289A |
| DS564 | M63Q + C173G + R207N + D250V + R325A | L52F + A108V + R354K and/or G284L/S + H287D + E289A |
| DS565 | M63Q + C173G + R207N + D250V + E328L | L52F + A108V + R354K and/or G284L/S + H287D + E289A |
| DS566 | M63Q + C173G + R207N + D250V + E328N | L52F + A108V + R354K and/or G284L/S + H287D + E289A |
| DS567 | M63Q + C173G + R207N + D250V | L52F + A108V + R354K and/or G284L/S + H287D + E289A |
| DS568 | M63Q + C173G + R207N + R325P + E328L | L52F + A108V + R354K and/or G284L/S + H287D + E289A |
| DS569 | M63Q + C173G + R207N + R325P + E328N | L52F + A108V + R354K and/or G284L/S + H287D + E289A |
| DS570 | M63Q + C173G + R207N + R325P | L52F + A108V + R354K and/or G284L/S + H287D + E289A |
| DS571 | M63Q + C173G + R207N + R325A + E328L | L52F + A108V + R354K and/or G284L/S + H287D + E289A |
| DS572 | M63Q + C173G + R207N + R325A + E328N | L52F + A108V + R354K and/or G284L/S + H287D + E289A |
| DS573 | M63Q + C173G + R207N + R325A | L52F + A108V + R354K and/or G284L/S + H287D + E289A |
| DS574 | M63Q + C173G + R207N + E328L | L52F + A108V + R354K and/or G284L/S + H287D + E289A |
| DS575 | M63Q + C173G + R207N + E328N | L52F + A108V + R354K and/or G284L/S + H287D + E289A |
| DS576 | M63Q + C173G + R207N | L52F + A108V + R354K and/or G284L/S + H287D + E289A |
| DS577 | M63Q + C173G + D250V + R325P + E328L | L52F + A108V + R354K and/or G284L/S + H287D + E289A |
| DS578 | M63Q + C173G + D250V + R325P + E328N | L52F + A108V + R354K and/or G284L/S + H287D + E289A |
| DS579 | M63Q + C173G + D250V + R325P | L52F + A108V + R354K and/or G284L/S + H287D + E289A |
| DS580 | M63Q + C173G + D250V + R325A + E328L | L52F + A108V + R354K and/or G284L/S + H287D + E289A |
| DS581 | M63Q + C173G + D250V + R325A + E328N | L52F + A108V + R354K and/or G284L/S + H287D + E289A |
| DS582 | M63Q + C173G + D250V + R325A | L52F + A108V + R354K and/or G284L/S + H287D + E289A |
| DS583 | M63Q + C173G + D250V + E328L | L52F + A108V + R354K and/or G284L/S + H287D + E289A |
| DS584 | M63Q + C173G + D250V + E328N | L52F + A108V + R354K and/or G284L/S + H287D + E289A |
| DS585 | M63Q + C173G + D250V | L52F + A108V + R354K and/or G284L/S + H287D + E289A |
| DS586 | M63Q + C173G + R325P + E328L | L52F + A108V + R354K and/or G284L/S + H287D + E289A |
| DS587 | M63Q + C173G + R325P + E328N | L52F + A108V + R354K and/or G284L/S + H287D + E289A |
| DS588 | M63Q + C173G + R325P | L52F + A108V + R354K and/or G284L/S + H287D + E289A |
| DS589 | M63Q + C173G + R325A + E328L | L52F + A108V + R354K and/or G284L/S + H287D + E289A |
| DS590 | M63Q + C173G + R325A + E328N | L52F + A108V + R354K and/or G284L/S + H287D + E289A |
| DS591 | M63Q + C173G + R325A | L52F + A108V + R354K and/or G284L/S + H287D + E289A |
| DS592 | M63Q + C173G + E328L | L52F + A108V + R354K and/or G284L/S + H287D + E289A |
| DS593 | M63Q + C173G + E328N | L52F + A108V + R354K and/or G284L/S + H287D + E289A |
| DS594 | M63Q + C173G | L52F + A108V + R354K and/or G284L/S + H287D + E289A |
| DS649 | L131P + C173R + R207L + D250V + R325P + E328L | L52F + A108V + R354K and/or G284L/S + H287D + E289A |
| DS650 | L131P + C173R + R207L + D250V + R325P + E328N | L52F + A108V + R354K and/or G284L/S + H287D + E289A |
| DS651 | L131P + C173R + R207L + D250V + R325P | L52F + A108V + R354K and/or G284L/S + H287D + E289A |
| DS652 | L131P + C173R + R207L + D250V + R325A + E328L | L52F + A108V + R354K and/or G284L/S + H287D + E289A |
| DS653 | L131P + C173R + R207L + D250V + R325A + E328N | L52F + A108V + R354K and/or G284L/S + H287D + E289A |
| DS654 | L131P + C173R + R207L + D250V + R325A | L52F + A108V + R354K and/or G284L/S + H287D + E289A |
| DS655 | L131P + C173R + R207L + D250V + E328L | L52F + A108V + R354K and/or G284L/S + H287D + E289A |
| DS656 | L131P + C173R + R207L + D250V + E328N | L52F + A108V + R354K and/or G284L/S + H287D + E289A |
| DS657 | L131P + C173R + R207L + D250V | L52F + A108V + R354K and/or G284L/S + H287D + E289A |
| DS658 | L131P + C173R + R207L + R325P + E328L | L52F + A108V + R354K and/or G284L/S + H287D + E289A |
| DS659 | L131P + C173R + R207L + R325P + E328N | L52F + A108V + R354K and/or G284L/S + H287D + E289A |
| DS660 | L131P + C173R + R207L + R325P | L52F + A108V + R354K and/or G284L/S + H287D + E289A |
| DS661 | L131P + C173R + R207L + R325A + E328L | L52F + A108V + R354K and/or G284L/S + H287D + E289A |
| DS662 | L131P + C173R + R207L + R325A + E328N | L52F + A108V + R354K and/or G284L/S + H287D + E289A |
| DS663 | L131P + C173R + R207L + R325A | L52F + A108V + R354K and/or G284L/S + H287D + E289A |
| DS664 | L131P + C173R + R207L + E328L | L52F + A108V + R354K and/or G284L/S + H287D + E289A |
| DS665 | L131P + C173R + R207L + E328N | L52F + A108V + R354K and/or G284L/S + H287D + E289A |
| DS666 | L131P + C173R + R207L | L52F + A108V + R354K and/or G284L/S + H287D + E289A |
| DS667 | L131P + C173R + R207N + D250V + R325P + E328L | L52F + A108V + R354K and/or G284L/S + H287D + E289A |
| DS668 | L131P + C173R + R207N + D250V + R325P + E328N | L52F + A108V + R354K and/or G284L/S + H287D + E289A |
| DS669 | L131P + C173R + R207N + D250V + R325P | L52F + A108V + R354K and/or G284L/S + H287D + E289A |
| DS670 | L131P + C173R + R207N + D250V + R325A + E328L | L52F + A108V + R354K and/or G284L/S + H287D + E289A |
| DS671 | L131P + C173R + R207N + D250V + R325A + E328N | L52F + A108V + R354K and/or G284L/S + H287D + E289A |
| DS672 | L131P + C173R + R207N + D250V + R325A | L52F + A108V + R354K and/or G284L/S + H287D + E289A |
| DS673 | L131P + C173R + R207N + D250V + E328L | L52F + A108V + R354K and/or G284L/S + H287D + E289A |
| DS674 | L131P + C173R + R207N + D250V + E328N | L52F + A108V + R354K and/or G284L/S + H287D + E289A |
| DS675 | L131P + C173R + R207N + D250V | L52F + A108V + R354K and/or G284L/S + H287D + E289A |
| DS676 | L131P + C173R + R207N + R325P + E328L | L52F + A108V + R354K and/or G284L/S + H287D + E289A |
| DS677 | L131P + C173R + R207N + R325P + E328N | L52F + A108V + R354K and/or G284L/S + H287D + E289A |
| DS678 | L131P + C173R + R207N + R325P | L52F + A108V + R354K and/or G284L/S + H287D + E289A |
| DS679 | L131P + C173R + R207N + R325A + E328L | L52F + A108V + R354K and/or G284L/S + H287D + E289A |
| DS680 | L131P + C173R + R207N + R325A + E328N | L52F + A108V + R354K and/or G284L/S + H287D + E289A |
| DS681 | L131P + C173R + R207N + R325A | L52F + A108V + R354K and/or G284L/S + H287D + E289A |
| DS682 | L131P + C173R + R207N + E328L | L52F + A108V + R354K and/or G284L/S + H287D + E289A |
| DS683 | L131P + C173R + R207N + E328N | L52F + A108V + R354K and/or G284L/S + H287D + E289A |
| DS684 | L131P + C173R + R207N | L52F + A108V + R354K and/or G284L/S + H287D + E289A |
| DS685 | L131P + C173R + D250V + R325P + E328L | L52F + A108V + R354K and/or G284L/S + H287D + E289A |
| DS686 | L131P + C173R + D250V + R325P + E328N | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS687 | L131P + C173R + D250V + R325P | L52F + A108V + R354K and/or G284L/S + H287D + E289A |
| DS688 | L131P + C173R + D250V + R325A + E328L | L52F + A108V + R354K and/or G284L/S + H287D + E289A |
| DS689 | L131P + C173R + D250V + R325A + E328N | L52F + A108V + R354K and/or G284L/S + H287D + E289A |
| DS690 | L131P + C173R + D250V + R325A | L52F + A108V + R354K and/or G284L/S + H287D + E289A |
| DS691 | L131P + C173R + D250V + E328L | L52F + A108V + R354K and/or G284L/S + H287D + E289A |
| DS692 | L131P + C173R + D250V + E328N | L52F + A108V + R354K and/or G284L/S + H287D + E289A |
| DS693 | L131P + C173R + D250V | L52F + A108V + R354K and/or G284L/S + H287D + E289A |
| DS694 | L131P + C173R + R325P + E328L | L52F + A108V + R354K and/or G284L/S + H287D + E289A |
| DS695 | L131P + C173R + R325P + E328N | L52F + A108V + R354K and/or G284L/S + H287D + E289A |
| DS696 | L131P + C173R + R325P | L52F + A108V + R354K and/or G284L/S + H287D + E289A |
| DS697 | L131P + C173R + R325A + E328L | L52F + A108V + R354K and/or G284L/S + H287D + E289A |
| DS698 | L131P + C173R + R325A + E328N | L52F + A108V + R354K and/or G284L/S + H287D + E289A |
| DS699 | L131P + C173R + R325A | L52F + A108V + R354K and/or G284L/S + H287D + E289A |
| DS700 | L131P + C173R + E328L | L52F + A108V + R354K and/or G284L/S + H287D + E289A |
| DS701 | L131P + C173R + E328N | L52F + A108V + R354K and/or G284L/S + H287D + E289A |
| DS702 | L131P + C173R | L52F + A108V + R354K and/or G284L/S + H287D + E289A |
| DS703 | L131P + C173G + R207L + D250V + R325P + E328L | L52F + A108V + R354K and/or G284L/S + H287D + E289A |
| DS704 | L131P + C173G + R207L + D250V + R325P + E328N | L52F + A108V + R354K and/or G284L/S + H287D + E289A |
| DS705 | L131P + C173G + R207L + D250V + R325P | L52F + A108V + R354K and/or G284L/S + H287D + E289A |
| DS706 | L131P + C173G + R207L + D250V + R325A + E328L | L52F + A108V + R354K and/or G284L/S + H287D + E289A |
| DS707 | L131P + C173G + R207L + D250V + R325A + E328N | L52F + A108V + R354K and/or G284L/S + H287D + E289A |
| DS708 | L131P + C173G + R207L + D250V + R325A | L52F + A108V + R354K and/or G284L/S + H287D + E289A |
| DS709 | L131P + C173G + R207L + D250V + E328L | L52F + A108V + R354K and/or G284L/S + H287D + E289A |
| DS710 | L131P + C173G + R207L + D250V + E328N | L52F + A108V + R354K and/or G284L/S + H287D + E289A |
| DS711 | L131P + C173G + R207L + D250V | L52F + A108V + R354K and/or G284L/S + H287D + E289A |
| DS712 | L131P + C173G + R207L + R325P + E328L | L52F + A108V + R354K and/or G284L/S + H287D + E289A |
| DS713 | L131P + C173G + R207L + R325P + E328N | L52F + A108V + R354K and/or G284L/S + H287D + E289A |
| DS714 | L131P + C173G + R207L + R325P | L52F + A108V + R354K and/or G284L/S + H287D + E289A |
| DS715 | L131P + C173G + R207L + R325A + E328L | L52F + A108V + R354K and/or G284L/S + H287D + E289A |
| DS716 | L131P + C173G + R207L + R325A + E328N | L52F + A108V + R354K and/or G284L/S + H287D + E289A |
| DS717 | L131P + C173G + R207L + R325A | L52F + A108V + R354K and/or G284L/S + H287D + E289A |
| DS718 | L131P + C173G + R207L + E328L | L52F + A108V + R354K and/or G284L/S + H287D + E289A |
| DS719 | L131P + C173G + R207L + E328N | L52F + A108V + R354K and/or G284L/S + H287D + E289A |
| DS720 | L131P + C173G + R207L | L52F + A108V + R354K and/or G284L/S + H287D + E289A |
| DS721 | L131P + C173G + R207N + D250V + R325P + E328L | L52F + A108V + R354K and/or G284L/S + H287D + E289A |
| DS722 | L131P + C173G + R207N + D250V + R325P + E328N | L52F + A108V + R354K and/or G284L/S + H287D + E289A |
| DS723 | L131P + C173G + R207N + D250V + R325P | L52F + A108V + R354K and/or G284L/S + H287D + E289A |
| DS724 | L131P + C173G + R207N + D250V + R325A + E328L | L52F + A108V + R354K and/or G284L/S + H287D + E289A |
| DS725 | L131P + C173G + R207N + D250V + R325A + E328N | L52F + A108V + R354K and/or G284L/S + H287D + E289A |
| DS726 | L131P + C173G + R207N + D250V + R325A | L52F + A108V + R354K and/or G284L/S + H287D + E289A |
| DS727 | L131P + C173G + R207N + D250V + E328L | L52F + A108V + R354K and/or G284L/S + H287D + E289A |
| DS728 | L131P + C173G + R207N + D250V + E328N | L52F + A108V + R354K and/or G284L/S + H287D + E289A |
| DS729 | L131P + C173G + R207N + D250V | L52F + A108V + R354K and/or G284L/S + H287D + E289A |
| DS730 | L131P + C173G + R207N + R325P + E328L | L52F + A108V + R354K and/or G284L/S + H287D + E289A |
| DS731 | L131P + C173G + R207N + R325P + E328N | L52F + A108V + R354K and/or G284L/S + H287D + E289A |
| DS732 | L131P + C173G + R207N + R325P | L52F + A108V + R354K and/or G284L/S + H287D + E289A |
| DS733 | L131P + C173G + R207N + R325A + E328L | L52F + A108V + R354K and/or G284L/S + H287D + E289A |
| DS734 | L131P + C173G + R207N + R325A + E328N | L52F + A108V + R354K and/or G284L/S + H287D + E289A |
| DS735 | L131P + C173G + R207N + R325A | L52F + A108V + R354K and/or G284L/S + H287D + E289A |
| DS736 | L131P + C173G + R207N + E328L | L52F + A108V + R354K and/or G284L/S + H287D + E289A |
| DS737 | L131P + C173G + R207N + E328N | L52F + A108V + R354K and/or G284L/S + H287D + E289A |
| DS738 | L131P + C173G + R207N | L52F + A108V + R354K and/or G284L/S + H287D + E289A |
| DS739 | L131P + C173G + D250V + R325P + E328L | L52F + A108V + R354K and/or G284L/S + H287D + E289A |
| DS740 | L131P + C173G + D250V + R325P + E328N | L52F + A108V + R354K and/or G284L/S + H287D + E289A |
| DS741 | L131P + C173G + D250V + R325P | L52F + A108V + R354K and/or G284L/S + H287D + E289A |
| DS742 | L131P + C173G + D250V + R325A + E328L | L52F + A108V + R354K and/or G284L/S + H287D + E289A |
| DS743 | L131P + C173G + D250V + R325A + E328N | L52F + A108V + R354K and/or G284L/S + H287D + E289A |
| DS744 | L131P + C173G + D250V + R325A | L52F + A108V + R354K and/or G284L/S + H287D + E289A |
| DS745 | L131P + C173G + D250V + E328L | L52F + A108V + R354K and/or G284L/S + H287D + E289A |
| DS746 | L131P + C173G + D250V + E328N | L52F + A108V + R354K and/or G284L/S + H287D + E289A |
| DS747 | L131P + C173G + D250V | L52F + A108V + R354K and/or G284L/S + H287D + E289A |
| DS748 | L131P + C173G + R325P + E328L | L52F + A108V + R354K and/or G284L/S + H287D + E289A |
| DS749 | L131P + C173G + R325P + E328N | L52F + A108V + R354K and/or G284L/S + H287D + E289A |
| DS750 | L131P + C173G + R325P | L52F + A108V + R354K and/or G284L/S + H287D + E289A |
| DS751 | L131P + C173G + R325A + E328L | L52F + A108V + R354K and/or G284L/S + H287D + E289A |
| DS752 | L131P + C173G + R325A + E328N | L52F + A108V + R354K and/or G284L/S + H287D + E289A |
| DS753 | L131P + C173G + R325A | L52F + A108V + R354K and/or G284L/S + H287D + E289A |
| DS754 | L131P + C173G + E328L | L52F + A108V + R354K and/or G284L/S + H287D + E289A |
| DS755 | L131P + C173G + E328N | L52F + A108V + R354K and/or G284L/S + H287D + E289A |
| DS756 | L131P + C173G | L52F + A108V + R354K and/or G284L/S + H287D + E289A |
| DS811 | C173R + R207L + D250V + R325P + E328L | L52F + A108V + R354K and/or G284L/S + H287D + E289A |
| DS812 | C173R + R207L + D250V + R325P + E328N | L52F + A108V + R354K and/or G284L/S + H287D + E289A |
| DS813 | C173R + R207L + D250V + R325P | L52F + A108V + R354K and/or G284L/S + H287D + E289A |
| DS814 | C173R + R207L + D250V + R325A + E328L | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
| --- | --- | --- |
| DS815 | C173R + R207L + D250V + R325A + E328N | L52F + A108V + R354K and/or G284L/S + H287D + E289A |
| DS816 | C173R + R207L + D250V + R325A | L52F + A108V + R354K and/or G284L/S + H287D + E289A |
| DS817 | C173R + R207L + D250V + E328L | L52F + A108V + R354K and/or G284L/S + H287D + E289A |
| DS818 | C173R + R207L + D250V + E328N | L52F + A108V + R354K and/or G284L/S + H287D + E289A |
| DS819 | C173R + R207L + D250V | L52F + A108V + R354K and/or G284L/S + H287D + E289A |
| DS820 | C173R + R207L + R325P + E328L | L52F + A108V + R354K and/or G284L/S + H287D + E289A |
| DS821 | C173R + R207L + R325P + E328N | L52F + A108V + R354K and/or G284L/S + H287D + E289A |
| DS822 | C173R + R207L + R325P | L52F + A108V + R354K and/or G284L/S + H287D + E289A |
| DS823 | C173R + R207L + R325A + E328L | L52F + A108V + R354K and/or G284L/S + H287D + E289A |
| DS824 | C173R + R207L + R325A + E328N | L52F + A108V + R354K and/or G284L/S + H287D + E289A |
| DS825 | C173R + R207L + R325A | L52F + A108V + R354K and/or G284L/S + H287D + E289A |
| DS826 | C173R + R207L + E328L | L52F + A108V + R354K and/or G284L/S + H287D + E289A |
| DS827 | C173R + R207L + E328N | L52F + A108V + R354K and/or G284L/S + H287D + E289A |
| DS828 | C173R + R207L | L52F + A108V + R354K and/or G284L/S + H287D + E289A |
| DS829 | C173R + R207N + D250V + R325P + E328L | L52F + A108V + R354K and/or G284L/S + H287D + E289A |
| DS830 | C173R + R207N + D250V + R325P + E328N | L52F + A108V + R354K and/or G284L/S + H287D + E289A |
| DS831 | C173R + R207N + D250V + R325P | L52F + A108V + R354K and/or G284L/S + H287D + E289A |
| DS832 | C173R + R207N + D250V + R325A + E328L | L52F + A108V + R354K and/or G284L/S + H287D + E289A |
| DS833 | C173R + R207N + D250V + R325A + E328N | L52F + A108V + R354K and/or G284L/S + H287D + E289A |
| DS834 | C173R + R207N + D250V + R325A | L52F + A108V + R354K and/or G284L/S + H287D + E289A |
| DS835 | C173R + R207N + D250V + E328L | L52F + A108V + R354K and/or G284L/S + H287D + E289A |
| DS836 | C173R + R207N + D250V + E328N | L52F + A108V + R354K and/or G284L/S + H287D + E289A |
| DS837 | C173R + R207N + D250V | L52F + A108V + R354K and/or G284L/S + H287D + E289A |
| DS838 | C173R + R207N + R325P + E328L | L52F + A108V + R354K and/or G284L/S + H287D + E289A |
| DS839 | C173R + R207N + R325P + E328N | L52F + A108V + R354K and/or G284L/S + H287D + E289A |
| DS840 | C173R + R207N + R325P | L52F + A108V + R354K and/or G284L/S + H287D + E289A |
| DS841 | C173R + R207N + R325A + E328L | L52F + A108V + R354K and/or G284L/S + H287D + E289A |
| DS842 | C173R + R207N + R325A + E328N | L52F + A108V + R354K and/or G284L/S + H287D + E289A |
| DS843 | C173R + R207N + R325A | L52F + A108V + R354K and/or G284L/S + H287D + E289A |
| DS844 | C173R + R207N + E328L | L52F + A108V + R354K and/or G284L/S + H287D + E289A |
| DS845 | C173R + R207N + E328N | L52F + A108V + R354K and/or G284L/S + H287D + E289A |
| DS846 | C173R + R207N | L52F + A108V + R354K and/or G284L/S + H287D + E289A |
| DS847 | C173R + D250V + R325P + E328L | L52F + A108V + R354K and/or G284L/S + H287D + E289A |
| DS848 | C173R + D250V + R325P + E328N | L52F + A108V + R354K and/or G284L/S + H287D + E289A |
| DS849 | C173R + D250V + R325P | L52F + A108V + R354K and/or G284L/S + H287D + E289A |
| DS850 | C173R + D250V + R325A + E328L | L52F + A108V + R354K and/or G284L/S + H287D + E289A |
| DS851 | C173R + D250V + R325A + E328N | L52F + A108V + R354K and/or G284L/S + H287D + E289A |
| DS852 | C173R + D250V + R325A | L52F + A108V + R354K and/or G284L/S + H287D + E289A |
| DS853 | C173R + D250V + E328L | L52F + A108V + R354K and/or G284L/S + H287D + E289A |
| DS854 | C173R + D250V + E328N | L52F + A108V + R354K and/or G284L/S + H287D + E289A |
| DS855 | C173R + D250V | L52F + A108V + R354K and/or G284L/S + H287D + E289A |
| DS856 | C173R + R325P + E328L | L52F + A108V + R354K and/or G284L/S + H287D + E289A |
| DS857 | C173R + R325P + E328N | L52F + A108V + R354K and/or G284L/S + H287D + E289A |
| DS858 | C173R + R325P | L52F + A108V + R354K and/or G284L/S + H287D + E289A |
| DS859 | C173R + R325A + E328L | L52F + A108V + R354K and/or G284L/S + H287D + E289A |
| DS860 | C173R + R325A + E328N | L52F + A108V + R354K and/or G284L/S + H287D + E289A |
| DS861 | C173R + R325A | L52F + A108V + R354K and/or G284L/S + H287D + E289A |
| DS862 | C173R + E328L | L52F + A108V + R354K and/or G284L/S + H287D + E289A |
| DS863 | C173R + E328N | L52F + A108V + R354K and/or G284L/S + H287D + E289A |
| DS864 | C173R | L52F + A108V + R354K and/or G284L/S + H287D + E289A |
| DS865 | C173G + R207L + D250V + R325P + E328L | L52F + A108V + R354K and/or G284L/S + H287D + E289A |
| DS866 | C173G + R207L + D250V + R325P + E328N | L52F + A108V + R354K and/or G284L/S + H287D + E289A |
| DS867 | C173G + R207L + D250V + R325P | L52F + A108V + R354K and/or G284L/S + H287D + E289A |
| DS868 | C173G + R207L + D250V + R325A + E328L | L52F + A108V + R354K and/or G284L/S + H287D + E289A |
| DS869 | C173G + R207L + D250V + R325A + E328N | L52F + A108V + R354K and/or G284L/S + H287D + E289A |
| DS870 | C173G + R207L + D250V + R325A | L52F + A108V + R354K and/or G284L/S + H287D + E289A |
| DS871 | C173G + R207L + D250V + E328L | L52F + A108V + R354K and/or G284L/S + H287D + E289A |
| DS872 | C173G + R207L + D250V + E328N | L52F + A108V + R354K and/or G284L/S + H287D + E289A |
| DS873 | C173G + R207L + D250V | L52F + A108V + R354K and/or G284L/S + H287D + E289A |
| DS874 | C173G + R207L + R325P + E328L | L52F + A108V + R354K and/or G284L/S + H287D + E289A |
| DS875 | C173G + R207L + R325P + E328N | L52F + A108V + R354K and/or G284L/S + H287D + E289A |
| DS876 | C173G + R207L + R325P | L52F + A108V + R354K and/or G284L/S + H287D + E289A |
| DS877 | C173G + R207L + R325A + E328L | L52F + A108V + R354K and/or G284L/S + H287D + E289A |
| DS878 | C173G + R207L + R325A + E328N | L52F + A108V + R354K and/or G284L/S + H287D + E289A |
| DS879 | C173G + R207L + R325A | L52F + A108V + R354K and/or G284L/S + H287D + E289A |
| DS880 | C173G + R207L + E328L | L52F + A108V + R354K and/or G284L/S + H287D + E289A |
| DS881 | C173G + R207L + E328N | L52F + A108V + R354K and/or G284L/S + H287D + E289A |
| DS882 | C173G + R207L | L52F + A108V + R354K and/or G284L/S + H287D + E289A |
| DS883 | C173G + R207N + D250V + R325P + E328L | L52F + A108V + R354K and/or G284L/S + H287D + E289A |
| DS884 | C173G + R207N + D250V + R325P + E328N | L52F + A108V + R354K and/or G284L/S + H287D + E289A |
| DS885 | C173G + R207N + D250V + R325P | L52F + A108V + R354K and/or G284L/S + H287D + E289A |
| DS886 | C173G + R207N + D250V + R325A + E328L | L52F + A108V + R354K and/or G284L/S + H287D + E289A |
| DS887 | C173G + R207N + D250V + R325A + E328N | L52F + A108V + R354K and/or G284L/S + H287D + E289A |
| DS888 | C173G + R207N + D250V + R325A | L52F + A108V + R354K and/or G284L/S + H287D + E289A |

TABLE 5-continued

Variants of TdT having the amino acid sequence of SEQ ID NO: 2 or an amino acid sequence within a specified percent sequence identity thereof, with at least a substitution on residue C173 and other residues as indicated (wherein the amino acid position numbers are with respect to SEQ ID NO: 2).

| Name | Variable Mutations | Optional Constant Mutations |
|---|---|---|
| DS889 | C173G + R207N + D250V + E328L | L52F + A108V + R354K and/or G284L/S + H287D + E289A |
| DS890 | C173G + R207N + D250V + E328N | L52F + A108V + R354K and/or G284L/S + H287D + E289A |
| DS891 | C173G + R207N + D250V | L52F + A108V + R354K and/or G284L/S + H287D + E289A |
| DS892 | C173G + R207N + R325P + E328L | L52F + A108V + R354K and/or G284L/S + H287D + E289A |
| DS893 | C173G + R207N + R325P + E328N | L52F + A108V + R354K and/or G284L/S + H287D + E289A |
| DS894 | C173G + R207N + R325P | L52F + A108V + R354K and/or G284L/S + H287D + E289A |
| DS895 | C173G + R207N + R325A + E328L | L52F + A108V + R354K and/or G284L/S + H287D + E289A |
| DS896 | C173G + R207N + R325A + E328N | L52F + A108V + R354K and/or G284L/S + H287D + E289A |
| DS897 | C173G + R207N + R325A | L52F + A108V + R354K and/or G284L/S + H287D + E289A |
| DS898 | C173G + R207N + E328L | L52F + A108V + R354K and/or G284L/S + H287D + E289A |
| DS899 | C173G + R207N + E328N | L52F + A108V + R354K and/or G284L/S + H287D + E289A |
| DS900 | C173G + R207N | L52F + A108V + R354K and/or G284L/S + H287D + E289A |
| DS901 | C173G + D250V + R325P + E328L | L52F + A108V + R354K and/or G284L/S + H287D + E289A |
| DS902 | C173G + D250V + R325P + E328N | L52F + A108V + R354K and/or G284L/S + H287D + E289A |
| DS903 | C173G + D250V + R325P | L52F + A108V + R354K and/or G284L/S + H287D + E289A |
| DS904 | C173G + D250V + R325A + E328L | L52F + A108V + R354K and/or G284L/S + H287D + E289A |
| DS905 | C173G + D250V + R325A + E328N | L52F + A108V + R354K and/or G284L/S + H287D + E289A |
| DS906 | C173G + D250V + R325A | L52F + A108V + R354K and/or G284L/S + H287D + E289A |
| DS907 | C173G + D250V + E328L | L52F + A108V + R354K and/or G284L/S + H287D + E289A |
| DS908 | C173G + D250V + E328N | L52F + A108V + R354K and/or G284L/S + H287D + E289A |
| DS909 | C173G + D250V | L52F + A108V + R354K and/or G284L/S + H287D + E289A |
| DS910 | C173G + R325P + E328L | L52F + A108V + R354K and/or G284L/S + H287D + E289A |
| DS911 | C173G + R325P + E328N | L52F + A108V + R354K and/or G284L/S + H287D + E289A |
| DS912 | C173G + R325P | L52F + A108V + R354K and/or G284L/S + H287D + E289A |
| DS913 | C173G + R325A + E328L | L52F + A108V + R354K and/or G284L/S + H287D + E289A |
| DS914 | C173G + R325A + E328N | L52F + A108V + R354K and/or G284L/S + H287D + E289A |
| DS915 | C173G + R325A | L52F + A108V + R354K and/or G284L/S + H287D + E289A |
| DS916 | C173G + E328L | L52F + A108V + R354K and/or G284L/S + H287D + E289A |
| DS917 | C173G + E328N | L52F + A108V + R354K and/or G284L/S + H287D + E289A |
| DS918 | C173G | L52F + A108V + R354K and/or G284L/S + H287D + E289A |

In a particular embodiment, the variants of the invention comprise the amino acid sequence of SEQ ID NO:2 (or functionally equivalent sequence) and optionally additional amino acid fragments at the C-ter or N-ter. In another embodiment, the variants of the invention consist solely on the amino acid sequence of SEQ ID NO:2 (or functionally equivalent sequence). More particularly, in a particular embodiment, the variants of the invention are deprived of the BRTC-like domain, which corresponds to residues 1 to 129 of SEQ ID NO:1.

According to a second aspect of the invention, the variant of Terminal deoxynucleotidyl Transferase (TdT) (i) comprises an amino acid sequence as set forth in SEQ ID NO:2 or a functionally equivalent sequence (such as, SEQ ID NOs:11, 13, 15, 17, 19, 21, 23, 25, 27, 29, 31, 33 or 35) or an amino acid sequence having a specified percent sequence identity of any of the foregoing sequences, with at least three amino acid substitutions selected from M63R/Q, L131P, C173G/R, R207L/N, D250V, R325P/N and E328N/L/T/S, or a functionally equivalent residue, wherein the positions are numbered by reference to the amino acid sequence set forth in SEQ ID NO:1 or as set forth directly elsewhere herein in respect of their individual SEQ ID NOs, (ii) is able to synthesize a nucleic acid fragment without template and (iii) is able to incorporate a modified nucleotide, such as a 3'-O-modified nucleotide, into the nucleic fragment.

For instance, the variant of TdT comprises an amino acid sequence within a specified percent sequence identity of SEQ ID NO:2 and a combination of substitutions selected from M63R+L131P+R207L, M63R+L131P+R207N, M63R+L131P+D250V, M63R+L131P+R325P, M63R+L131P+R325A, M63R+L131P+E328L, M63R+L131P+E328N, M63R+R207L+D250V, M63R+R207L+R325P, M63R+R207L+R325A, M63R+R207L+E328L, M63R+R207L+E328N, M63R+R207N+D250V, M63R+R207N+R325P, M63R+R207N+R325A, M63R+R207N+E328L, M63R+R207N+E328N, M63R+D250V+R325P, M63R+D250V+R325A, M63R+R325P+E328L, M63R+R325P+E328N, M63R+R325A+E328L, M63R+R325A+E328N, M63Q+L131P+R207L, M63Q+L131P+R207N, M63Q+L131P+D250V, M63Q+L131P+R325P, M63Q+L131P+R325A, M63Q+L131P+E328L, M63Q+L131P+E328N, M63Q+R207L+D250V, M63Q+R207L+R325P, M63Q+R207L+R325A, M63Q+R207L+E328L, M63Q+R207L+E328N, M63Q+D250V+R325P, M63Q+D250V+R325A, M63Q+D250V+E328L, M63Q+D250V+E328N, M63Q+R325P+E328L, M63Q+R325P+E328N, M63Q+R325A+E328L, M63Q+R325A+E328N, L131P+R207L+D250V, L131P+R207L+R325A, L131P+R207L+E328L, L131P+R207L+E328N, L131P+R207N+D250V, L131P+R207N+R325P, L131P+R207N+R325A, L131P+R207N+E328L, L131P+R207N+E328N, L131P+D250V+R325P, L131P+D250V+R325A, L131P+D250V+E328L, L131P+D250V+E328N, L131P+R325P+E328L, L131P+R325P+E328N, L131P+R325A+E328L, L131P+R325A+E328N, R207L+D250V+R325P, R207L+D250V+R325A, R207L+D250V+E328L, R207L+D250V+E328N, R207L+R325P+E328L, R207L+R325P+E328N, R207L+R325A+E328L, R207L+R325A+E328N, R207N+D250V+R325P, R207N+D250V+R325A, R207N+D250V+E328L, R207N+D250V+E328N, R207N+R325P+E328L, R207N+R325P+E328N, R207N+R325A+E328L, R207N+R325A+E328N, D250V+R325P+E328L, D250V+R325P+E328N, D250V+R325A+E328L, D250V+R325A+E328N and R207L+D250V+R325P, or functionally equivalent residue(s) wherein the above position numbers are with respect to SEQ ID NO:2.

In a particular embodiment, the variant of TdT comprises an amino acid sequence within a specified percent sequence identity of SEQ ID NO:2, or functionally equivalent sequence, with the combination of substitutions R207L+R325P+E328L (DS928), or functionally equivalent residues.

In a particular embodiment, the variant of TdT comprises an amino acid sequence within a specified percent sequence identity of SEQ ID NO:2, or functionally equivalent sequence, with the combination of substitutions R207N+R325A+E328N (DS950), or functionally equivalent residues.

Such variant may further comprise at least one substitution at position corresponding to residues selected from L52, A108, L131, T340, G284, H287, E289, W450, R354 and A510, or functionally equivalent residue(s).

As exposed above, said variant may also comprise the combination of constant mutations L52F+A108V+R354K and/or G284L/S+H287D+E289A, or functionally equivalent residue(s).

According to a further aspect, the invention provides a variant of Terminal deoxynucleotidyl Transferase (TdT) which (i) comprises an amino acid sequence within a specified percent sequence identity of SEQ ID NO:2 or a functionally equivalent sequence, with at least one amino acid substitution selected from M63R, M63Q, L131P, R207L, R207N, D250V, R325P, R325A, E328L, E328N, or functionally equivalent residue(s), (ii) is able to synthesize a nucleic acid fragment without a template and (iii) is able to incorporate a 3'-O-modified nucleotide into the nucleic fragment.

In another aspect, the invention provides a variant of Terminal deoxynucleotidyl Transferase (TdT) which (i) comprises an amino acid sequence within a specified percent sequence identity of SEQ ID NO:2 or a functionally equivalent sequence, with at least the combination of substitutions selected from M63R+L131P, M63R+R207L, M63R+R207N, M63R+D250V, M63R+R325P, M63R+R325A, M63R+E328L, M63R+E328N, M63Q+L131P, M63Q+R207L, M63Q+R207N, M63Q+D250V, M63Q+R325P, M63Q+R325A, M63Q+E328L, M63Q+E328N, L131P+R207L, L131P+R207N, L131P+D250V, L131P+R325P, L131P+R325A, L131P+E328L, L131P+E328N, R207L+D250V, R207L+R325P, R207L+R325A, R207L+E328L, R207L+E328N, R207N+D250V, R207N+R325P, R207N+R325A, R207N+E328L, R207N+E328N, D250V+R325P, D250V+R325A, D250V+E328L, D250V+E328N, R325P+E328L, R325P+E328N, R325A+E328L and R325A+E328N, or functionally equivalent residue(s), wherein the positions are numbered by reference to the amino acid sequence set forth in SEQ ID NO:2, (ii) is able to synthesize a nucleic acid fragment without a template and (iii) is able to incorporate a 3'-O-modified nucleotide into the nucleic acid fragment.

It is thus an object of the invention to provide a TdT variant having an amino acid sequence within a specified percent sequence identity of SEQ ID NO:2, or functionally equivalent sequence, with any substitution or combination of substitutions listed in Table 6, listed as "Variable Mutations", or functionally equivalent residue(s) and optionally one or both combinations of constant mutations L52F+A108V+R354K an G284L/S+H287D+E289A, or functionally equivalent residue(s).

According to a particular embodiment, the variant comprises at least one substitution or combination of substitutions as listed in Table 6, and optionally one or more additional mutation(s).

TABLE 2

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
|---|---|---|
| DS109 | M63R + L131P + R207L + D250V + R325P + E328L | L52F + A108V + R354K and/or G284L/S + H287D + E289A |
| DS110 | M63R + L131P + R207L + D250V + R325P + E328N | L52F + A108V + R354K and/or G284L/S + H287D + E289A |
| DS111 | M63R + L131P + R207L + D250V + R325P | L52F + A108V + R354K and/or G284L/S + H287D + E289A |
| DS112 | M63R + L131P + R207L + D250V + R325A + E328L | L52F + A108V + R354K and/or G284L/S + H287D + E289A |
| DS113 | M63R + L131P + R207L + D250V + R325A + E328N | L52F + A108V + R354K and/or G284L/S + H287D + E289A |
| DS114 | M63R + L131P + R207L + D250V + R325A | L52F + A108V + R354K and/or G284L/S + H287D + E289A |
| DS115 | M63R + L131P + R207L + D250V + E328L | L52F + A108V + R354K and/or G284L/S + H287D + E289A |
| DS116 | M63R + L131P + R207L + D250V + E328N | L52F + A108V + R354K and/or G284L/S + H287D + E289A |
| DS117 | M63R + L131P + R207L + D250V | L52F + A108V + R354K and/or G284L/S + H287D + E289A |
| DS118 | M63R + L131P + R207L + R325P + E328L | L52F + A108V + R354K and/or G284L/S + H287D + E289A |
| DS119 | M63R + L131P + R207L + R325P + E328N | L52F + A108V + R354K and/or G284L/S + H287D + E289A |
| DS120 | M63R + L131P + R207L + R325P | L52F + A108V + R354K and/or G284L/S + H287D + E289A |
| DS121 | M63R + L131P + R207L + R325A + E328L | L52F + A108V + R354K and/or G284L/S + H287D + E289A |
| DS122 | M63R + L131P + R207L + R325A + E328N | L52F + A108V + R354K and/or G284L/S + H287D + E289A |
| DS123 | M63R + L131P + R207L + R325A | L52F + A108V + R354K and/or G284L/S + H287D + E289A |
| DS124 | M63R + L131P + R207L + E328L | L52F + A108V + R354K and/or G284L/S + H287D + E289A |
| DS125 | M63R + L131P + R207L + E328N | L52F + A108V + R354K and/or G284L/S + H287D + E289A |
| DS126 | M63R + L131P + R207L | L52F + A108V + R354K and/or G284L/S + H287D + E289A |
| DS127 | M63R + L131P + R207N + D250V + R325P + E328L | L52F + A108V + R354K and/or G284L/S + H287D + E289A |
| DS128 | M63R + L131P + R207N + D250V + R325P + E328N | L52F + A108V + R354K and/or G284L/S + H287D + E289A |
| DS129 | M63R + L131P + R207N + D250V + R325P | L52F + A108V + R354K and/or G284L/S + H287D + E289A |
| DS130 | M63R + L131P + R207N + D250V + R325A + E328L | L52F + A108V + R354K and/or G284L/S + H287D + E289A |
| DS131 | M63R + L131P + R207N + D250V + R325A + E328N | L52F + A108V + R354K and/or G284L/S + H287D + E289A |
| DS132 | M63R + L131P + R207N + D250V + R325A | L52F + A108V + R354K and/or G284L/S + H287D + E289A |
| DS133 | M63R + L131P + R207N + D250V + E328L | L52F + A108V + R354K and/or G284L/S + H287D + E289A |
| DS134 | M63R + L131P + R207N + D250V + E328N | L52F + A108V + R354K and/or G284L/S + H287D + E289A |
| DS135 | M63R + L131P + R207N + D250V | L52F + A108V + R354K and/or G284L/S + H287D + E289A |
| DS136 | M63R + L131P + R207N + R325P + E328L | L52F + A108V + R354K and/or G284L/S + H287D + E289A |
| DS137 | M63R + L131P + R207N + R325P + E328N | L52F + A108V + R354K and/or G284L/S + H287D + E289A |
| DS138 | M63R + L131P + R207N + R325P | L52F + A108V + R354K and/or G284L/S + H287D + E289A |
| DS139 | M63R + L131P + R207N + R325A + E328L | L52F + A108V + R354K and/or G284L/S + H287D + E289A |
| DS140 | M63R + L131P + R207N + R325A + E328N | L52F + A108V + R354K and/or G284L/S + H287D + E289A |

TABLE 2-continued

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
|---|---|---|
| DS141 | M63R + L131P + R207N + R325A | L52F + A108V + R354K and/or G284L/S + H287D + E289A |
| DS142 | M63R + L131P + R207N + E328L | L52F + A108V + R354K and/or G284L/S + H287D + E289A |
| DS143 | M63R + L131P + R207N + E328N | L52F + A108V + R354K and/or G284L/S + H287D + E289A |
| DS144 | M63R + L131P + R207N | L52F + A108V + R354K and/or G284L/S + H287D + E289A |
| DS145 | M63R + L131P + D250V + R325P + E328L | L52F + A108V + R354K and/or G284L/S + H287D + E289A |
| DS146 | M63R + L131P + D250V + R325P + E328N | L52F + A108V + R354K and/or G284L/S + H287D + E289A |
| DS147 | M63R + L131P + D250V + R325P | L52F + A108V + R354K and/or G284L/S + H287D + E289A |
| DS148 | M63R + L131P + D250V + R325A + E328L | L52F + A108V + R354K and/or G284L/S + H287D + E289A |
| DS149 | M63R + L131P + D250V + R325A + E328N | L52F + A108V + R354K and/or G284L/S + H287D + E289A |
| DS150 | M63R + L131P + D250V + R325A | L52F + A108V + R354K and/or G284L/S + H287D + E289A |
| DS151 | M63R + L131P + D250V + E328L | L52F + A108V + R354K and/or G284L/S + H287D + E289A |
| DS152 | M63R + L131P + D250V + E328N | L52F + A108V + R354K and/or G284L/S + H287D + E289A |
| DS153 | M63R + L131P + D250V | L52F + A108V + R354K and/or G284L/S + H287D + E289A |
| DS154 | M63R + L131P + R325P + E328L | L52F + A108V + R354K and/or G284L/S + H287D + E289A |
| DS155 | M63R + L131P + R325P + E328N | L52F + A108V + R354K and/or G284L/S + H287D + E289A |
| DS156 | M63R + L131P + R325P | L52F + A108V + R354K and/or G284L/S + H287D + E289A |
| DS157 | M63R + L131P + R325A + E328L | L52F + A108V + R354K and/or G284L/S + H287D + E289A |
| DS158 | M63R + L131P + R325A + E328N | L52F + A108V + R354K and/or G284L/S + H287D + E289A |
| DS159 | M63R + L131P + R325A | L52F + A108V + R354K and/or G284L/S + H287D + E289A |
| DS160 | M63R + L131P + E328L | L52F + A108V + R354K and/or G284L/S + H287D + E289A |
| DS161 | M63R + L131P + E328N | L52F + A108V + R354K and/or G284L/S + H287D + E289A |
| DS162 | M63R + L131P | L52F + A108V + R354K and/or G284L/S + H287D + E289A |
| DS271 | M63R + R207L + D250V + R325P + E328L | L52F + A108V + R354K and/or G284L/S + H287D + E289A |
| DS272 | M63R + R207L + D250V + R325P + E328N | L52F + A108V + R354K and/or G284L/S + H287D + E289A |
| DS273 | M63R + R207L + D250V + R325P | L52F + A108V + R354K and/or G284L/S + H287D + E289A |
| DS274 | M63R + R207L + D250V + R325A + E328L | L52F + A108V + R354K and/or G284L/S + H287D + E289A |
| DS275 | M63R + R207L + D250V + R325A + E328N | L52F + A108V + R354K and/or G284L/S + H287D + E289A |
| DS276 | M63R + R207L + D250V + R325A | L52F + A108V + R354K and/or G284L/S + H287D + E289A |
| DS277 | M63R + R207L + D250V + E328L | L52F + A108V + R354K and/or G284L/S + H287D + E289A |
| DS278 | M63R + R207L + D250V + E328N | L52F + A108V + R354K and/or G284L/S + H287D + E289A |
| DS279 | M63R + R207L + D250V | L52F + A108V + R354K and/or G284L/S + H287D + E289A |
| DS280 | M63R + R207L + R325P + E328L | L52F + A108V + R354K and/or G284L/S + H287D + E289A |
| DS281 | M63R + R207L + R325P + E328N | L52F + A108V + R354K and/or G284L/S + H287D + E289A |
| DS282 | M63R + R207L + R325P | L52F + A108V + R354K and/or G284L/S + H287D + E289A |
| DS283 | M63R + R207L + R325A + E328L | L52F + A108V + R354K and/or G284L/S + H287D + E289A |
| DS284 | M63R + R207L + R325A + E328N | L52F + A108V + R354K and/or G284L/S + H287D + E289A |
| DS285 | M63R + R207L + R325A | L52F + A108V + R354K and/or G284L/S + H287D + E289A |
| DS286 | M63R + R207L + E328L | L52F + A108V + R354K and/or G284L/S + H287D + E289A |
| DS287 | M63R + R207L + E328N | L52F + A108V + R354K and/or G284L/S + H287D + E289A |
| DS288 | M63R + R207L | L52F + A108V + R354K and/or G284L/S + H287D + E289A |
| DS289 | M63R + R207N + D250V + R325P + E328L | L52F + A108V + R354K and/or G284L/S + H287D + E289A |
| DS290 | M63R + R207N + D250V + R325P + E328N | L52F + A108V + R354K and/or G284L/S + H287D + E289A |
| DS291 | M63R + R207N + D250V + R325P | L52F + A108V + R354K and/or G284L/S + H287D + E289A |
| DS292 | M63R + R207N + D250V + R325A + E328L | L52F + A108V + R354K and/or G284L/S + H287D + E289A |
| DS293 | M63R + R207N + D250V + R325A + E328N | L52F + A108V + R354K and/or G284L/S + H287D + E289A |
| DS294 | M63R + R207N + D250V + R325A | L52F + A108V + R354K and/or G284L/S + H287D + E289A |
| DS295 | M63R + R207N + D250V + E328L | L52F + A108V + R354K and/or G284L/S + H287D + E289A |
| DS296 | M63R + R207N + D250V + E328N | L52F + A108V + R354K and/or G284L/S + H287D + E289A |
| DS297 | M63R + R207N + D250V | L52F + A108V + R354K and/or G284L/S + H287D + E289A |
| DS298 | M63R + R207N + R325P + E328L | L52F + A108V + R354K and/or G284L/S + H287D + E289A |
| DS299 | M63R + R207N + R325P + E328N | L52F + A108V + R354K and/or G284L/S + H287D + E289A |
| DS300 | M63R + R207N + R325P | L52F + A108V + R354K and/or G284L/S + H287D + E289A |
| DS301 | M63R + R207N + R325A + E328L | L52F + A108V + R354K and/or G284L/S + H287D + E289A |
| DS173 | M63R + R207N + R325A + E328N | L52F + A108V + R354K and/or G284L/S + H287D + E289A |
| DS303 | M63R + R207N + R325A | L52F + A108V + R354K and/or G284L/S + H287D + E289A |
| DS304 | M63R + R207N + E328L | L52F + A108V + R354K and/or G284L/S + H287D + E289A |
| DS305 | M63R + R207N + E328N | L52F + A108V + R354K and/or G284L/S + H287D + E289A |
| DS306 | M63R + R207N | L52F + A108V + R354K and/or G284L/S + H287D + E289A |
| DS307 | M63R + D250V + R325P + E328L | L52F + A108V + R354K and/or G284L/S + H287D + E289A |
| DS308 | M63R + D250V + R325P + E328N | L52F + A108V + R354K and/or G284L/S + H287D + E289A |
| DS309 | M63R + D250V + R325P | L52F + A108V + R354K and/or G284L/S + H287D + E289A |
| DS310 | M63R + D250V + R325A + E328L | L52F + A108V + R354K and/or G284L/S + H287D + E289A |
| DS311 | M63R + D250V + R325A + E328N | L52F + A108V + R354K and/or G284L/S + H287D + E289A |
| DS312 | M63R + D250V + R325A | L52F + A108V + R354K and/or G284L/S + H287D + E289A |
| DS313 | M63R + D250V + E328L | L52F + A108V + R354K and/or G284L/S + H287D + E289A |
| DS314 | M63R + D250V + E328N | L52F + A108V + R354K and/or G284L/S + H287D + E289A |
| DS315 | M63R + D250V | L52F + A108V + R354K and/or G284L/S + H287D + E289A |
| DS316 | M63R + R325P + E328L | L52F + A108V + R354K and/or G284L/S + H287D + E289A |
| DS317 | M63R + R325P + E328N | L52F + A108V + R354K and/or G284L/S + H287D + E289A |
| DS318 | M63R + R325P | L52F + A108V + R354K and/or G284L/S + H287D + E289A |
| DS319 | M63R + R325A + E328L | L52F + A108V + R354K and/or G284L/S + H287D + E289A |
| DS320 | M63R + R325A + E328N | L52F + A108V + R354K and/or G284L/S + H287D + E289A |
| DS321 | M63R + R325A | L52F + A108V + R354K and/or G284L/S + H287D + E289A |
| DS322 | M63R + E328L | L52F + A108V + R354K and/or G284L/S + H287D + E289A |

TABLE 2-continued

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
|---|---|---|
| DS323 | M63R + E328N | L52F + A108V + R354K and/or G284L/S + H287D + E289A |
| DS324 | M63R | L52F + A108V + R354K and/or G284L/S + H287D + E289A |
| DS433 | M63Q + L131P + R207L + D250V + R325P + E328L | L52F + A108V + R354K and/or G284L/S + H287D + E289A |
| DS434 | M63Q + L131P + R207L + D250V + R325P + E328N | L52F + A108V + R354K and/or G284L/S + H287D + E289A |
| DS435 | M63Q + L131P + R207L + D250V + R325P | L52F + A108V + R354K and/or G284L/S + H287D + E289A |
| DS436 | M63Q + L131P + R207L + D250V + R325A + E328L | L52F + A108V + R354K and/or G284L/S + H287D + E289A |
| DS437 | M63Q + L131P + R207L + D250V + R325A + E328N | L52F + A108V + R354K and/or G284L/S + H287D + E289A |
| DS438 | M63Q + L131P + R207L + D250V + R325A | L52F + A108V + R354K and/or G284L/S + H287D + E289A |
| DS439 | M63Q + L131P + R207L + D250V + E328L | L52F + A108V + R354K and/or G284L/S + H287D + E289A |
| DS440 | M63Q + L131P + R207L + D250V + E328N | L52F + A108V + R354K and/or G284L/S + H287D + E289A |
| DS441 | M63Q + L131P + R207L + D250V | L52F + A108V + R354K and/or G284L/S + H287D + E289A |
| DS442 | M63Q + L131P + R207L + R325P + E328L | L52F + A108V + R354K and/or G284L/S + H287D + E289A |
| DS443 | M63Q + L131P + R207L + R325P + E328N | L52F + A108V + R354K and/or G284L/S + H287D + E289A |
| DS444 | M63Q + L131P + R207L + R325P | L52F + A108V + R354K and/or G284L/S + H287D + E289A |
| DS445 | M63Q + L131P + R207L + R325A + E328L | L52F + A108V + R354K and/or G284L/S + H287D + E289A |
| DS446 | M63Q + L131P + R207L + R325A + E328N | L52F + A108V + R354K and/or G284L/S + H287D + E289A |
| DS447 | M63Q + L131P + R207L + R325A | L52F + A108V + R354K and/or G284L/S + H287D + E289A |
| DS448 | M63Q + L131P + R207L + E328L | L52F + A108V + R354K and/or G284L/S + H287D + E289A |
| DS449 | M63Q + L131P + R207L + E328N | L52F + A108V + R354K and/or G284L/S + H287D + E289A |
| DS450 | M63Q + L131P + R207L | L52F + A108V + R354K and/or G284L/S + H287D + E289A |
| DS451 | M63Q + L131P + R207N + D250V + R325P + E328L | L52F + A108V + R354K and/or G284L/S + H287D + E289A |
| DS452 | M63Q + L131P + R207N + D250V + R325P + E328N | L52F + A108V + R354K and/or G284L/S + H287D + E289A |
| DS453 | M63Q + L131P + R207N + D250V + R325P | L52F + A108V + R354K and/or G284L/S + H287D + E289A |
| DS325 | M63Q + L131P + R207N + D250V + R325A + E328L | L52F + A108V + R354K and/or G284L/S + H287D + E289A |
| DS455 | M63Q + L131P + R207N + D250V + R325A + E328N | L52F + A108V + R354K and/or G284L/S + H287D + E289A |
| DS456 | M63Q + L131P + R207N + D250V + R325A | L52F + A108V + R354K and/or G284L/S + H287D + E289A |
| DS328 | M63Q + L131P + R207N + D250V + E328L | L52F + A108V + R354K and/or G284L/S + H287D + E289A |
| DS458 | M63Q + L131P + R207N + D250V + E328N | L52F + A108V + R354K and/or G284L/S + H287D + E289A |
| DS459 | M63Q + L131P + R207N + D250V | L52F + A108V + R354K and/or G284L/S + H287D + E289A |
| DS460 | M63Q + L131P + R207N + R325P + E328L | L52F + A108V + R354K and/or G284L/S + H287D + E289A |
| DS461 | M63Q + L131P + R207N + R325P + E328N | L52F + A108V + R354K and/or G284L/S + H287D + E289A |
| DS462 | M63Q + L131P + R207N + R325P | L52F + A108V + R354K and/or G284L/S + H287D + E289A |
| DS463 | M63Q + L131P + R207N + R325A + E328L | L52F + A108V + R354K and/or G284L/S + H287D + E289A |
| DS464 | M63Q + L131P + R207N + R325A + E328N | L52F + A108V + R354K and/or G284L/S + H287D + E289A |
| DS465 | M63Q + L131P + R207N + R325A | L52F + A108V + R354K and/or G284L/S + H287D + E289A |
| DS466 | M63Q + L131P + R207N + E328L | L52F + A108V + R354K and/or G284L/S + H287D + E289A |
| DS467 | M63Q + L131P + R207N + E328N | L52F + A108V + R354K and/or G284L/S + H287D + E289A |
| DS468 | M63Q + L131P + R207N | L52F + A108V + R354K and/or G284L/S + H287D + E289A |
| DS469 | M63Q + L131P + D250V + R325P + E328L | L52F + A108V + R354K and/or G284L/S + H287D + E289A |
| DS470 | M63Q + L131P + D250V + R325P + E328N | L52F + A108V + R354K and/or G284L/S + H287D + E289A |
| DS471 | M63Q + L131P + D250V + R325P | L52F + A108V + R354K and/or G284L/S + H287D + E289A |
| DS472 | M63Q + L131P + D250V + R325A + E328L | L52F + A108V + R354K and/or G284L/S + H287D + E289A |
| DS473 | M63Q + L131P + D250V + R325A + E328N | L52F + A108V + R354K and/or G284L/S + H287D + E289A |
| DS474 | M63Q + L131P + D250V + R325A | L52F + A108V + R354K and/or G284L/S + H287D + E289A |
| DS475 | M63Q + L131P + D250V + E328L | L52F + A108V + R354K and/or G284L/S + H287D + E289A |
| DS476 | M63Q + L131P + D250V + E328N | L52F + A108V + R354K and/or G284L/S + H287D + E289A |
| DS477 | M63Q + L131P + D250V | L52F + A108V + R354K and/or G284L/S + H287D + E289A |
| DS478 | M63Q + L131P + R325P + E328L | L52F + A108V + R354K and/or G284L/S + H287D + E289A |
| DS479 | M63Q + L131P + R325P + E328N | L52F + A108V + R354K and/or G284L/S + H287D + E289A |
| DS354 | M63Q + L131P + R325P | L52F + A108V + R354K and/or G284L/S + H287D + E289A |
| DS481 | M63Q + L131P + R325A + E328L | L52F + A108V + R354K and/or G284L/S + H287D + E289A |
| DS482 | M63Q + L131P + R325A + E328N | L52F + A108V + R354K and/or G284L/S + H287D + E289A |
| DS483 | M63Q + L131P + R325A | L52F + A108V + R354K and/or G284L/S + H287D + E289A |
| DS484 | M63Q + L131P + E328L | L52F + A108V + R354K and/or G284L/S + H287D + E289A |
| DS485 | M63Q + L131P + E328N | L52F + A108V + R354K and/or G284L/S + H287D + E289A |
| DS486 | M63Q + L131P | L52F + A108V + R354K and/or G284L/S + H287D + E289A |
| DS595 | M63Q + R207L + D250V + R325P + E328L | L52F + A108V + R354K and/or G284L/S + H287D + E289A |
| DS596 | M63Q + R207L + D250V + R325P + E328N | L52F + A108V + R354K and/or G284L/S + H287D + E289A |
| DS597 | M63Q + R207L + D250V + R325P | L52F + A108V + R354K and/or G284L/S + H287D + E289A |
| DS598 | M63Q + R207L + D250V + R325A + E328L | L52F + A108V + R354K and/or G284L/S + H287D + E289A |
| DS599 | M63Q + R207L + D250V + R325A + E328N | L52F + A108V + R354K and/or G284L/S + H287D + E289A |
| DS600 | M63Q + R207L + D250V + R325A | L52F + A108V + R354K and/or G284L/S + H287D + E289A |
| DS601 | M63Q + R207L + D250V + E328L | L52F + A108V + R354K and/or G284L/S + H287D + E289A |
| DS602 | M63Q + R207L + D250V + E328N | L52F + A108V + R354K and/or G284L/S + H287D + E289A |
| DS603 | M63Q + R207L + D250V | L52F + A108V + R354K and/or G284L/S + H287D + E289A |
| DS604 | M63Q + R207L + R325P + E328L | L52F + A108V + R354K and/or G284L/S + H287D + E289A |
| DS605 | M63Q + R207L + R325P + E328N | L52F + A108V + R354K and/or G284L/S + H287D + E289A |
| DS606 | M63Q + R207L + R325P | L52F + A108V + R354K and/or G284L/S + H287D + E289A |
| DS607 | M63Q + R207L + R325A+ E328L | L52F + A108V + R354K and/or G284L/S + H287D + E289A |
| DS608 | M63Q + R207L + R325A+ E328N | L52F + A108V + R354K and/or G284L/S + H287D + E289A |
| DS609 | M63Q + R207L + R325A | L52F + A108V + R354K and/or G284L/S + H287D + E289A |
| DS610 | M63Q + R207L + E328L | L52F + A108V + R354K and/or G284L/S + H287D + E289A |
| DS611 | M63Q + R207L + E328N | L52F + A108V + R354K and/or G284L/S + H287D + E289A |
| DS612 | M63Q + R207L | L52F + A108V + R354K and/or G284L/S + H287D + E289A |

TABLE 2-continued

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
|---|---|---|
| DS613 | M63Q + R207N + D250V + R325P + E328L | L52F + A108V + R354K and/or G284L/S + H287D + E289A |
| DS614 | M63Q + R207N + D250V + R325P + E328N | L52F + A108V + R354K and/or G284L/S + H287D + E289A |
| DS615 | M63Q + R207N + D250V + R325P | L52F + A108V + R354K and/or G284L/S + H287D + E289A |
| DS616 | M63Q + R207N + D250V + R325A + E328L | L52F + A108V + R354K and/or G284L/S + H287D + E289A |
| DS617 | M63Q + R207N + D250V + R325A + E328N | L52F + A108V + R354K and/or G284L/S + H287D + E289A |
| DS618 | M63Q + R207N + D250V + R325A | L52F + A108V + R354K and/or G284L/S + H287D + E289A |
| DS619 | M63Q + R207N + D250V + E328L | L52F + A108V + R354K and/or G284L/S + H287D + E289A |
| DS620 | M63Q + R207N + D250V + E328N | L52F + A108V + R354K and/or G284L/S + H287D + E289A |
| DS621 | M63Q + R207N + D250V | L52F + A108V + R354K and/or G284L/S + H287D + E289A |
| DS622 | M63Q + R207N + R325P + E328L | L52F + A108V + R354K and/or G284L/S + H287D + E289A |
| DS623 | M63Q + R207N + R325P + E328N | L52F + A108V + R354K and/or G284L/S + H287D + E289A |
| DS624 | M63Q + R207N + R325P | L52F + A108V + R354K and/or G284L/S + H287D + E289A |
| DS625 | M63Q + R207N + R325A + E328L | L52F + A108V + R354K and/or G284L/S + H287D + E289A |
| DS626 | M63Q + R207N + R325A + E328N | L52F + A108V + R354K and/or G284L/S + H287D + E289A |
| DS627 | M63Q + R207N + R325A | L52F + A108V + R354K and/or G284L/S + H287D + E289A |
| DS628 | M63Q + R207N + E328L | L52F + A108V + R354K and/or G284L/S + H287D + E289A |
| DS629 | M63Q + R207N + E328N | L52F + A108V + R354K and/or G284L/S + H287D + E289A |
| DS630 | M63Q + R207N | L52F + A108V + R354K and/or G284L/S + H287D + E289A |
| DS631 | M63Q + D250V + R325P + E328L | L52F + A108V + R354K and/or G284L/S + H287D + E289A |
| DS632 | M63Q + D250V + R325P + E328N | L52F + A108V + R354K and/or G284L/S + H287D + E289A |
| DS633 | M63Q + D250V + R325P | L52F + A108V + R354K and/or G284L/S + H287D + E289A |
| DS634 | M63Q + D250V + R325A + E328L | L52F + A108V + R354K and/or G284L/S + H287D + E289A |
| DS635 | M63Q + D250V + R325A + E328N | L52F + A108V + R354K and/or G284L/S + H287D + E289A |
| DS636 | M63Q + D250V + R325A | L52F + A108V + R354K and/or G284L/S + H287D + E289A |
| DS637 | M63Q + D250V + E328L | L52F + A108V + R354K and/or G284L/S + H287D + E289A |
| DS638 | M63Q + D250V + E328N | L52F + A108V + R354K and/or G284L/S + H287D + E289A |
| DS639 | M63Q + D250V | L52F + A108V + R354K and/or G284L/S + H287D + E289A |
| DS640 | M63Q + R325P + E328L | L52F + A108V + R354K and/or G284L/S + H287D + E289A |
| DS641 | M63Q + R325P + E328N | L52F + A108V + R354K and/or G284L/S + H287D + E289A |
| DS642 | M63Q + R325P | L52F + A108V + R354K and/or G284L/S + H287D + E289A |
| DS643 | M63Q + R325A + E328L | L52F + A108V + R354K and/or G284L/S + H287D + E289A |
| DS644 | M63Q + R325A + E328N | L52F + A108V + R354K and/or G284L/S + H287D + E289A |
| DS645 | M63Q + R325A | L52F + A108V + R354K and/or G284L/S + H287D + E289A |
| DS646 | M63Q + E328L | L52F + A108V + R354K and/or G284L/S + H287D + E289A |
| DS647 | M63Q + E328N | L52F + A108V + R354K and/or G284L/S + H287D + E289A |
| DS648 | M63Q | L52F + A108V + R354K and/or G284L/S + H287D + E289A |
| DS757 | L131P + R207L + D250V + R325P + E328L | L52F + A108V + R354K and/or G284L/S + H287D + E289A |
| DS758 | L131P + R207L + D250V + R325P + E328N | L52F + A108V + R354K and/or G284L/S + H287D + E289A |
| DS759 | L131P + R207L + D250V + R325P | L52F + A108V + R354K and/or G284L/S + H287D + E289A |
| DS760 | L131P + R207L + D250V + R325A + E328L | L52F + A108V + R354K and/or G284L/S + H287D + E289A |
| DS761 | L131P + R207L + D250V + R325A + E328N | L52F + A108V + R354K and/or G284L/S + H287D + E289A |
| DS762 | L131P + R207L + D250V + R325A | L52F + A108V + R354K and/or G284L/S + H287D + E289A |
| DS763 | L131P + R207L + D250V + E328L | L52F + A108V + R354K and/or G284L/S + H287D + E289A |
| DS764 | L131P + R207L + D250V + E328N | L52F + A108V + R354K and/or G284L/S + H287D + E289A |
| DS765 | L131P + R207L + D250V | L52F + A108V + R354K and/or G284L/S + H287D + E289A |
| DS766 | L131P + R207L + R325P + E328L | L52F + A108V + R354K and/or G284L/S + H287D + E289A |
| DS767 | L131P + R207L + R325P + E328N | L52F + A108V + R354K and/or G284L/S + H287D + E289A |
| DS768 | L131P + R207L + R325P | L52F + A108V + R354K and/or G284L/S + H287D + E289A |
| DS769 | L131P + R207L + R325A + E328L | L52F + A108V + R354K and/or G284L/S + H287D + E289A |
| DS770 | L131P + R207L + R325A + E328N | L52F + A108V + R354K and/or G284L/S + H287D + E289A |
| DS771 | L131P + R207L + R325A | L52F + A108V + R354K and/or G284L/S + H287D + E289A |
| DS772 | L131P + R207L + E328L | L52F + A108V + R354K and/or G284L/S + H287D + E289A |
| DS773 | L131P + R207L + E328N | L52F + A108V + R354K and/or G284L/S + H287D + E289A |
| DS774 | L131P + R207L | L52F + A108V + R354K and/or G284L/S + H287D + E289A |
| DS775 | L131P + R207N + D250V + R325P + E328L | L52F + A108V + R354K and/or G284L/S + H287D + E289A |
| DS776 | L131P + R207N + D250V + R325P + E328N | L52F + A108V + R354K and/or G284L/S + H287D + E289A |
| DS777 | L131P + R207N + D250V + R325P | L52F + A108V + R354K and/or G284L/S + H287D + E289A |
| DS778 | L131P + R207N + D250V + R325A + E328L | L52F + A108V + R354K and/or G284L/S + H287D + E289A |
| DS779 | L131P + R207N + D250V + R325A + E328N | L52F + A108V + R354K and/or G284L/S + H287D + E289A |
| DS780 | L131P + R207N + D250V + R325A | L52F + A108V + R354K and/or G284L/S + H287D + E289A |
| DS781 | L131P + R207N + D250V + E328L | L52F + A108V + R354K and/or G284L/S + H287D + E289A |
| DS782 | L131P + R207N + D250V + E328N | L52F + A108V + R354K and/or G284L/S + H287D + E289A |
| DS783 | L131P + R207N + D250V | L52F + A108V + R354K and/or G284L/S + H287D + E289A |
| DS784 | L131P + R207N + R325P + E328L | L52F + A108V + R354K and/or G284L/S + H287D + E289A |
| DS785 | L131P + R207N + R325P + E328N | L52F + A108V + R354K and/or G284L/S + H287D + E289A |
| DS786 | L131P + R207N + R325P | L52F + A108V + R354K and/or G284L/S + H287D + E289A |
| DS787 | L131P + R207N + R325A + E328L | L52F + A108V + R354K and/or G284L/S + H287D + E289A |
| DS788 | L131P + R207N + R325A + E328N | L52F + A108V + R354K and/or G284L/S + H287D + E289A |
| DS789 | L131P + R207N + R325A | L52F + A108V + R354K and/or G284L/S + H287D + E289A |
| DS790 | L131P + R207N + E328L | L52F + A108V + R354K and/or G284L/S + H287D + E289A |
| DS791 | L131P + R207N + E328N | L52F + A108V + R354K and/or G284L/S + H287D + E289A |
| DS792 | L131P + R207N | L52F + A108V + R354K and/or G284L/S + H287D + E289A |
| DS793 | L131P + D250V + R325P + E328L | L52F + A108V + R354K and/or G284L/S + H287D + E289A |
| DS794 | L131P + D250V + R325P + E328N | L52F + A108V + R354K and/or G284L/S + H287D + E289A |

TABLE 2-continued

Variants of TdT having the amino acid sequence of SEQ ID NO: 2, or an amino acid sequence within a specified percent sequence identity thereof, and further including the following Variable Mutations and Optional Constant Mutations (wherein amino acid position numbers are with respect to SEQ ID NO: 2).

| Name | Variable Mutations | Optional Constant Mutations |
| --- | --- | --- |
| DS795 | L131P + D250V + R325P | L52F + A108V + R354K and/or G284L/S + H287D + E289A |
| DS796 | L131P + D250V + R325A + E328L | L52F + A108V + R354K and/or G284L/S + H287D + E289A |
| DS797 | L131P + D250V + R325A + E328N | L52F + A108V + R354K and/or G284L/S + H287D + E289A |
| DS798 | L131P + D250V + R325A | L52F + A108V + R354K and/or G284L/S + H287D + E289A |
| DS799 | L131P + D250V + E328L | L52F + A108V + R354K and/or G284L/S + H287D + E289A |
| DS800 | L131P + D250V + E328N | L52F + A108V + R354K and/or G284L/S + H287D + E289A |
| DS801 | L131P + D250V | L52F + A108V + R354K and/or G284L/S + H287D + E289A |
| DS802 | L131P + R325P + E328L | L52F + A108V + R354K and/or G284L/S + H287D + E289A |
| DS803 | L131P + R325P + E328N | L52F + A108V + R354K and/or G284L/S + H287D + E289A |
| DS804 | L131P + R325P | L52F + A108V + R354K and/or G284L/S + H287D + E289A |
| DS805 | L131P + R325A + E328L | L52F + A108V + R354K and/or G284L/S + H287D + E289A |
| DS806 | L131P + R325A + E328N | L52F + A108V + R354K and/or G284L/S + H287D + E289A |
| DS807 | L131P + R325A | L52F + A108V + R354K and/or G284L/S + H287D + E289A |
| DS808 | L131P + E328L | L52F + A108V + R354K and/or G284L/S + H287D + E289A |
| DS809 | L131P + E328N | L52F + A108V + R354K and/or G284L/S + H287D + E289A |
| DS810 | L131P | L52F + A108V + R354K and/or G284L/S + H287D + E289A |
| DS921 | R207L + D250V + R325P | L52F + A108V + R354K and/or G284L/S + H287D + E289A |
| DS922 | R207L + D250V + R325A + E328L | L52F + A108V + R354K and/or G284L/S + H287D + E289A |
| DS923 | R207L + D250V + R325A + E328N | L52F + A108V + R354K and/or G284L/S + H287D + E289A |
| DS924 | R207L + D250V + R325A | L52F + A108V + R354K and/or G284L/S + H287D + E289A |
| DS925 | R207L + D250V + E328L | L52F + A108V + R354K and/or G284L/S + H287D + E289A |
| DS926 | R207L + D250V + E328N | L52F + A108V + R354K and/or G284L/S + H287D + E289A |
| DS927 | R207L + D250V | L52F + A108V + R354K and/or G284L/S + H287D + E289A |
| DS928 | R207L + R325P + E328L | L52F + A108V + R354K and/or G284L/S + H287D + E289A |
| DS929 | R207L + R325P + E328N | L52F + A108V + R354K and/or G284L/S + H287D + E289A |
| DS930 | R207L + R325P | L52F + A108V + R354K and/or G284L/S + H287D + E289A |
| DS931 | R207L + R325A + E328L | L52F + A108V + R354K and/or G284L/S + H287D + E289A |
| DS932 | R207L + R325A + E328N | L52F + A108V + R354K and/or G284L/S + H287D + E289A |
| DS933 | R207L + R325A | L52F + A108V + R354K and/or G284L/S + H287D + E289A |
| DS934 | R207L + E328L | L52F + A108V + R354K and/or G284L/S + H287D + E289A |
| DS935 | R207L + E328N | L52F + A108V + R354K and/or G284L/S + H287D + E289A |
| DS936 | R207L | L52F + A108V + R354K and/or G284L/S + H287D + E289A |
| DS937 | R207N + D250V + R325P + E328L | L52F + A108V + R354K and/or G284L/S + H287D + E289A |
| DS938 | R207N + D250V + R325P + E328N | L52F + A108V + R354K and/or G284L/S + H287D + E289A |
| DS939 | R207N + D250V + R325P | L52F + A108V + R354K and/or G284L/S + H287D + E289A |
| DS940 | R207N + D250V + R325A + E328L | L52F + A108V + R354K and/or G284L/S + H287D + E289A |
| DS941 | R207N + D250V + R325A + E328N | L52F + A108V + R354K and/or G284L/S + H287D + E289A |
| DS942 | R207N + D250V + R325A | L52F + A108V + R354K and/or G284L/S + H287D + E289A |
| DS943 | R207N + D250V + E328L | L52F + A108V + R354K and/or G284L/S + H287D + E289A |
| DS944 | R207N + D250V + E328N | L52F + A108V + R354K and/or G284L/S + H287D + E289A |
| DS945 | R207N + D250V | L52F + A108V + R354K and/or G284L/S + H287D + E289A |
| DS946 | R207N + R325P + E328L | L52F + A108V + R354K and/or G284L/S + H287D + E289A |
| DS947 | R207N + R325P + E328N | L52F + A108V + R354K and/or G284L/S + H287D + E289A |
| DS948 | R207N + R325P | L52F + A108V + R354K and/or G284L/S + H287D + E289A |
| DS949 | R207N + R325A + E328L | L52F + A108V + R354K and/or G284L/S + H287D + E289A |
| DS950 | R207N + R325A + E328N | L52F + A108V + R354K and/or G284L/S + H287D + E289A |
| DS951 | R207N + R325A | L52F + A108V + R354K and/or G284L/S + H287D + E289A |
| DS952 | R207N + E328L | L52F + A108V + R354K and/or G284L/S + H287D + E289A |
| DS953 | R207N + E328N | L52F + A108V + R354K and/or G284L/S + H287D + E289A |
| DS954 | R207N | L52F + A108V + R354K and/or G284L/S + H287D + E289A |
| DS955 | D250V + R325P + E328L | L52F + A108V + R354K and/or G284L/S + H287D + E289A |
| DS956 | D250V + R325P + E328N | L52F + A108V + R354K and/or G284L/S + H287D + E289A |
| DS957 | D250V + R325P | L52F + A108V + R354K and/or G284L/S + H287D + E289A |
| DS958 | D250V + R325A + E328L | L52F + A108V + R354K and/or G284L/S + H287D + E289A |
| DS959 | D250V + R325A + E328N | L52F + A108V + R354K and/or G284L/S + H287D + E289A |
| DS960 | D250V + R325A | L52F + A108V + R354K and/or G284L/S + H287D + E289A |
| DS961 | D250V + E328L | L52F + A108V + R354K and/or G284L/S + H287D + E289A |
| DS962 | D250V + E328N | L52F + A108V + R354K and/or G284L/S + H287D + E289A |
| DS963 | D250V | L52F + A108V + R354K and/or G284L/S + H287D + E289A |
| DS964 | R325P + E328L | L52F + A108V + R354K and/or G284L/S + H287D + E289A |
| DS965 | R325P + E328N | L52F + A108V + R354K and/or G284L/S + H287D + E289A |
| DS966 | R325P | L52F + A108V + R354K and/or G284L/S + H287D + E289A |
| DS967 | R325A + E328L | L52F + A108V + R354K and/or G284L/S + H287D + E289A |
| DS968 | R325A + E328N | L52F + A108V + R354K and/or G284L/S + H287D + E289A |
| DS969 | R325A | L52F + A108V + R354K and/or G284L/S + H287D + E289A |
| DS970 | E328L | L52F + A108V + R354K and/or G284L/S + H287D + E289A |
| DS971 | E328N | L52F + A108V + R354K and/or G284L/S + H287D + E289A |
| DS919 | R207L + D250V + R325P + E328L | L52F + A108V + R354K and/or G284L/S + H287D + E289A |
| DS920 | R207L + D250V + R325P + E328N | L52F + A108V + R354K and/or G284L/S + H287D + E289A |

According to some embodiments, a variant of TdT has a substitution or combination of substitutions described above and has an amino acid sequence within at least 80% identity with SEQ ID NO:2 or with a functionally equivalent sequence (such as, SEQ ID NOs:11, 13, 15, 17, 19, 21, 23, 25, 27, 29, 31, 33 or 35); in some embodiments, such amino acid sequence is within at least 85%, 90%, 95%, 96%, 97%, 98%, or 99% identity with SEQ ID NO:2 or functionally equivalent sequence (such as, SEQ ID NOs:11, 13, 15, 17, 19, 21, 23, 25, 27, 29, 31, 33 or 35).

Additional Modifications

In an embodiment, the variant of TdT further includes any type of tagging peptide in its N-terminal, C-terminal or both extremity, such as a His-tag sequence. Said tagging peptide could be used for purification, identification, increasing expression, secretability or increasing catalytic activity. It will be understood that such different tags are extensively described in the literature and thus all tag known to a skilled person are covered by the present invention.

The variants of the invention can also include one or more exogenous or heterologous features at the N- and/or C-terminal regions of the protein for use, e.g., in the purification of the recombinant polymerase.

The variant of the invention may further comprise a substitution of residues between positions C378 to L406, wherein the positions are numbered by reference to the amino acid sequence set forth in SEQ ID NO1, or functionally equivalent residues, by residues H363 to C390 of the Polu polymerase of sequence SEQ ID NO:3, wherein the positions are numbered by reference to the amino acid sequence set forth in SEQ ID NO:3 or functionally equivalent residues.

Advantageously, the variant of TdT comprises at least the amino acid sequence SEQ ID NO:2, 11, 13, 15, 17, 19, 21, 23, 25, 27, 29, 31, 33 or 35, with the disclosed substitution(s) and percent sequence identity values.

Nucleic Acids, Expression Cassette, Vector

It is also the purpose of the invention to provide a nucleic acid molecule encoding a variant of the invention. As used herein, the term "nucleic acid", "nucleic sequence," "polynucleotide", "oligonucleotide" and "nucleotide sequence" are used interchangeably and refer to a sequence of deoxyribonucleotides and/or ribonucleotides. In one embodiment, the nucleic acid is a DNA. In an alternative embodiment, the nucleic acid is RNA. In an alternative embodiment, the nucleic acid is XNA.

The nucleic acids can be in single stranded form or in duplex form or a mixture of the two. It can be of recombinant, artificial and/or synthetic origin and it can comprise modified nucleotides. Such modifications could be natural modifications such as epigenetic modifications, or unnatural modification such as labels, modified bond, a modified purine or pyrimidine base, or a modified sugar. In one embodiment, nucleic acid molecules are DNA, RNA or XNA bearing naturally occurring epigenetic modifications such as methylation, hydroxymethylation, formylation or 5-carboxylation. In one embodiment, nucleic acid molecules are DNA, RNA or XNA bearing unnaturally occurring modifications such as fluorescent tag, fluorescent label, interaction groups.

The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding a TdT variant as defined above. Such stringent conditions include incubations of hybridization filters at about 42° C for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding a TdT variant of the invention, wherein the sequence of said nucleic acids, or a portion of said sequence at least, has been engineered using optimized codon usage.

Alternatively, the nucleic acids according to the invention may be deduced from the sequence of the TdT variant according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

In one embodiment, nucleic acid molecules are polymeric molecules having length of more than 50, 100, 200, 300, 400, 500, 600, 700, 800, 900, 1 000, 2 000, 3 000, 4 000, 5 000, 6 000, 7 000, 8 000, 9 000, 10 000, 15 000, 20 000, 30 000, 40 000, 50 000 or 100 000 nucleotides.

Nucleic acids of the invention may further comprise additional nucleotide sequences, such as regulatory regions, i.e., promoters, enhancers, silencers, terminators, signal peptides and the like that can be used to cause or regulate expression of the polypeptide in a selected host cell or system.

The present invention further relates to an expression cassette comprising a nucleic acid according to the invention operably linked to one or more control sequences that direct the expression of said nucleic acid in a suitable host cell. Typically, the expression cassette comprises, or consists of, a nucleic acid according to the invention operably linked to a control sequence such as transcriptional promoter and/or transcription terminator. The control sequence may include a promoter that is recognized by a host cell or an in vitro expression system for expression of a nucleic acid encoding a TdT variant of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. The control sequence may also be a transcription terminator, which is recognized by a host cell to terminate transcription. The terminator is operably linked to the 3'-terminus of the nucleic acid encoding the esterase. Any terminator that is functional in the host cell may be used in the present invention. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA molecule used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally present operator. An expression vector can also contain an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. The choice of the vector will typically depend on the compatibility of the vector with the host cell into which the vector is to be introduced.

It is another object of the invention to provide a host cell comprising a nucleic acid, an expression cassette or a vector as described above. The present invention thus relates to the use of a nucleic acid, expression cassette or vector according to the invention to transform, transfect or transduce a host cell. The choice of the vector will typically depend on the compatibility of the vector with the host cell into which it must be introduced.

According to the invention, the host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The term "host cell" also encompasses any progeny of a parent host cell that is not identical to the parent host cell due to mutations that occur during replication. The host cell may be any cell useful in the production of a variant of the present invention, e.g., a prokaryote or a eukaryote. The prokaryotic host cell may be any Gram-positive or Gram-negative bacterium. The host cell may also be an eukaryotic cell, such as a yeast, fungal, mammalian, insect or plant cell.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation, Optionally, more than one copy of a nucleic acid, cassette or vector of the present invention may be inserted into a host cell to increase production of the variant.

Modified Nucleotides

According to the invention, the variants of TdT are able to incorporate modified nucleotides, such as modified 3'O-nucleotides, including 3'O-blocked nucleotides.

In the context of the invention, the expression "Modified Nucleotide" refers to a molecule containing a nucleoside (i.e. a base attached to a deoxyribose or ribose sugar molecule) bound to three phosphate groups which has at least one additional group on one of its extremity: 2', 3', 5' or base. Said additional group blocks further addition of nucleotides by preventing the formation of any phosphodiester bond (3'O-modification, 2' or 2'O modifications) or by sterically preventing the polymerase to attach to any nucleic acid fragments that comprises on its 3' extremity such modified nucleotide (5' or base modification). Furtherly, said additional group has advantageously a reversible nature allowing that group to be removed through a specific cleaving reaction.

Nucleosides or nucleotide triphosphates include deoxyadenosine triphosphate (dATP), deoxyguanosine triphosphate (dGTP), deoxycytidine triphosphate (dCTP) or deoxythymidine triphosphate (dTTP) for examples of nucleotide containing deoxyribose. Adenosine triphosphate (ATP), guanosine triphosphate (GTP), cytidine triphosphate (CTP) or uridine triphosphate (UTP) are further examples of nucleotide triphosphates containing ribose. Other types of nucleosides may be bound to three phosphates to form nucleotide triphosphates, such as naturally occurring modified nucleosides and artificial nucleosides.

In a particular embodiment, the modified nucleotide is a 3'O-blocked nucleotide, which comprises a group reversibly attached to the 3' end of the nucleotide triphosphate to prevent further nucleotide addition. Said group could have diverse chemical natures, such as azidomethyl, aminoxy, and allyl.

Advantageously, the modified nucleotide is selected from a 3'-O—NH2-nucleoside triphosphate, a 3'-O-azidomethyl-nucleoside triphosphate, a 3'-O-allyl-nucleoside triphosphate, a 3'O-(2-nitrobenzyl)-nucleoside triphosphate, or a 3'-O-propargyl-nucleoside triphosphate.

In some embodiments, the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure:

-O-Z wherein —Z is any of -C(R')$_2$-O-R", —C(R')$_2$-N(R")2, —C(R')$_2$-N(H)R", —C(R')$_2$-S-R" and —C(R')$_2$-F, wherein each R" is or is part of a removable protecting group; each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; with the proviso that in some embodiments such substituents have up to 10 carbon atoms and/or up to 5 oxygen or nitrogen heteroatoms; or (R')2 represents an alkylidene group of formula=C(R''')2 wherein each R''' may be the same or different and is selected from the group comprising hydrogen and halogen atoms and alkyl groups, with the proviso that in some embodiments the alkyl of each R''' has from 1 to 3 carbon atoms; and wherein the molecule may be reacted to yield an intermediate in which each R" is exchanged for H or, where Z is -(R')$_2$-F, the F is exchanged for OH, SH or NH2, preferably OH, which intermediate dissociates under aqueous conditions to afford a molecule with a free 3'-OH; with the proviso that where Z is —C(R')$_2$-S-R", both R' groups are not H. In certain embodiments, R' of the modified nucleotide or nucleoside is an alkyl or substituted alkyl, with the proviso that such alkyl or substituted alkyl has from 1 to 10 carbon atoms and from 0 to 4 oxygen or nitrogen heteroatoms. In certain embodiments, -Z of the modified nucleotide or nucleoside is of formula —C(R')$_2$-N3. In certain embodiments, Z is an azidomethyl group.

In some embodiments, Z is a cleavable organic moiety with or without heteroatoms having a molecular weight of 200 or less. In other embodiments, Z is a cleavable organic moiety with or without heteroatoms having a molecular weight of 100 or less. In other embodiments, Z is a cleavable organic moiety with or without heteroatoms having a molecular weight of 50 or less.

In a further particular embodiment, "3'O modified nucleotide" refers to nucleotide triphosphate bearing at the 3' extremity either a 3'-O-methyl, 3'-azido, 3'-O-azidomethyl, 3'-O-amino, 3'-aminoxy or 3'-O-allyl group. In a further embodiment, the 3'-blocked nucleotide triphosphate is blocked by either a 3'-O-azidomethyl, 3'-aminoxy or 3'-O-allyl group. In other embodiments, "3'O modified nucleotide" refers to nucleotide triphosphate bearing at the 3' extremity either esters, ethers, carbonitriles, phosphates, carbonates, carbamates, hydroxylamine, borates, nitrates, sugars, phosphoramide, phosphoramidates, phenylsulfenates, sulfates, sulfones or amino acids. In some embodiments, the foregoing 3'-O-blocking groups have a molecule weight of 100 or less.

In another embodiments, 3'-O-blocking groups of the invention include methyl, 3'-O-(2-nitrobenzyl), allyl, amine, azidomethyl, tert-butoxy ethoxy, or propargyl.

In further particular embodiment, "3'O modified nucleotide" refers to a nucleotide triphosphate having a terminator effector modifying group such as those described in WO2016034807.

Interestingly, the variants of the invention exhibit an increased affinity for modified nucleotides, as compared to wild type TdT, and thereby an increased ability to incorporate such modified nucleotide in a nucleic acid sequence during nucleic acid synthesis. More particularly, the variants of the invention are able to use and incorporate modified 3'O-nucleotides (and more particularly, 3'O-blocked nucleotide) in nucleic acid sequence, which is not possible with wild type TdT (see Knapp et al. Chem. Eur. J., 2011, 17:2903).

According to a particular aspect, the invention relates to variants of TdT able to work with modified nucleotides in a nucleic acids enzymatic synthesis process, particularly with 3'O-modified nucleotides (e.g., 3'O-blocked nucleotide), and having the ability to produce long length nucleic acid molecules or derivative of nucleic acid molecules.

Enzymatic Synthesis of Nucleic Acid

It is the purpose of the present invention to provide variants of TdT that may be used for the synthesis of nucleic acid, such as described in Ybert et al, WO2015/159023; Jensen et al, Biochemistry, 57: 1821-1832 (2018); Hiatt et al, U.S. Pat. No. 5,808,045. More particularly, it is the purpose of the present invention to provide variants of TdT suitable to add modified nucleotides to an initiating nucleic acid strand. The blocking group may be then removed for allowing a new addition of modified nucleotide.

According to the invention, by use of a variant of the invention, it is possible to implement successive cycles comprising additions and deprotections. This process will therefore allow by multiple cycles of addition of a reversible modified nucleotide and further removal of the blocking group to allow the controlled extension of an initiating nucleic acid strand into a defined sequence.

The present invention contemplates the use of modified TdT according to the present invention in any enzymatic nucleic acid synthesis process.

It is thus an object of the present invention to provide a method of synthesizing a polynucleotide having a predetermined sequence, comprising the steps of:
  a) providing an initiator having a 3'-terminal nucleotide having a free 3'-hydroxyl;
  b) repeating cycles of (i) contacting under elongation conditions the initiator or elongated fragments having free 3'-O-hydroxyls with a 3'-O-blocked nucleoside triphosphate and a TdT variant of the present invention, so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until the polynucleotide is formed.

It is also the purpose of the present invention to provide a process for synthesizing a nucleic acid molecule without template, comprising a step of contacting a nucleic acid primer with both at least one nucleotide, such as at least one 3'O-modified nucleotide, and a variant of the invention.

The present invention contemplates the concept of enzymatic nucleic acids synthesis process. In such process, nucleic acids molecules are de novo synthesized in absence of any template strand. Accordingly, ordered sequence of nucleotides are coupled to an initiator nucleic acid fragment with the help of the variant of the invention. It will be understood that quantitative coupling and more generally high coupling efficiency of each nucleotide to the growing nucleic acid chain is of great importance. It will also be understood that non-terminator nucleotides, such as natural nucleotides or permanent labeled nucleotides, will not permit any control over the sequence synthesized and will result, for example, in uncontrolled and undesired poly-additions.

In some embodiments, the method of synthesizing a polynucleotide comprises the steps of (a) providing an initiator having a free 3'-hydroxyl; (b) reacting under extension conditions the initiator or an extension intermediate having a free 3'-hydroxyl with a variant TdT of the invention in the presence of a 3'-O-blocked nucleoside triphosphate to produce a 3'-O-blocked extension intermediate; (c) deblocking the extension intermediate to produce an extension intermediate with a free 3'-hydroxyl; and (d) repeating steps (b) and (c) until the polynucleotide is synthesized.

In some embodiments, the method of synthesizing a polynucleotide comprises the steps of (a) providing an initiator attached to a solid support, the iniator being an oligonucleotide having a free 3'-hydroxyl; (b) reacting under extension conditions the initiator or an extension intermediate having a free 3'-hydroxyl with a variant TdT of the invention in the presence of a 3'-O-blocked nucleoside triphosphate to produce a 3'-O-blocked extension intermediate; (c) washing the solid support to remove unincorporated 3'-O-blocked nucleoside triphosphate; (d) deblocking the extension intermediate by exposing the solid support to a deblocking agent to produce an extension intermediate having a free 3'-hydroxyl; and (c) repeating steps (b) and (d) until the polynucleotide is synthesized. The method may include a further step of cleaving the completed polynucleotide from the solid support.

In some embodiments, for TdT catalyzed addition reactions, the enzymatic conditions may contain from about 0.20 and about 200 µM of the nucleotide having the removable blocking moiety protecting the 3'-hydroxyl and from about 0.20 to 200 µM of free and unmodified 3'-hydroxyls derived from the initiating substrate. In some embodiments, the reaction buffer contains from about 10 to about 500 mM potassium cacodylate buffer (pH between 6.5 and 7.5). and from about 0.01 to about 10 mM of a divalent cation (e.g. CoC12 or MnC12). Other buffer compositions and components may be suitable for particular desired embodiment of the present invention.

In the context of the invention, the expression "cleaving reaction" refers to any action of substance or physical conditions, which is able to cleave the additional group previously described on reversible modified nucleotides. A person skilled in the art is able to determine a cleaving reaction for any previously listed group.

In one embodiment, the cleaving agent is a chemical cleaving agent. In an alternative embodiment, the cleaving agent is an enzymatic cleaving agent.

It will be understood by the person skilled in the art that the selection of cleaving agent is dependent on the type of 3'-nucleotide blocking group used. For example, tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiment, the cleaving reaction is involving: TCEP, a palladium complex or sodium nitrite.

In particular embodimentd, the cleaving reaction is performed in the presence of additional components such as a denaturant (urea, guanidinium chloride, formamide or betaine for example). In a further embodiment, the cleavage reaction is performed with one or more buffers. It will be understood by the person skilled in the art that the choice of buffer is dependent on the exact mechanism of reaction.

The present invention relates to variants of TdT with the capacity to incorporate, in a quantitative way, modified nucleotides. By "quantitative way" or "quantitative reaction", it is meant a reaction that goes to completion, i.e. in which reactants are totally converted into the product. Polymerase that incorporates in a quantitative way reversible modified nucleotide is a polymerase able to elongate every fragment of nucleic acid with all the nucleotides available leading to the conversion of all the initiating fragments of length n, to fragments of length n+1.

As used herein, "initiating fragment" refers to a short oligonucleotide sequence with a free 3'-end, which can be further elongated. In one embodiment, the initiating fragment is a DNA initiating fragment. In an alternative embodiment, the initiating fragment is an RNA initiating fragment.

In one embodiment, the initiating fragment possesses between 3 and 100 nucleotides, in particular between 3 and 20 nucleotides.

In one embodiment, the initiating fragment is single-stranded. In an alternative embodiment, the initiating fragment is double-stranded.

In one embodiment, the initiating fragment is immobilized on a solid support. The initiating fragment may be attached with various method to a solid support resulting in a stable under the various enzymatic or synthesis reaction conditions that the fragment will undergo.

In one embodiment, the initiating fragment is immobilized on a solid support via a reversible interacting moiety, such as a chemically-cleavable linker, an antibody/immunogenic epitope, a biotin/biotin-binding protein or glutathione-GST tag. In a further embodiment, the initiating fragment is immobilized on a solid support via a chemically-cleavable linker, such as a disulfide, allyl, or azide-masked hemiaminal ether linker.

In an initiating fragment, the immobilized part contains at least one restriction site. The use of restriction enzymes and restriction sites to selectively hydrolyze nucleic acids chain at a specific site is describe in the literature. Any skilled person will be able to choose the appropriate restriction enzyme that will match the initiating fragment cleaving site sequence.

In an alternative embodiment, the initiating fragment contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Applications

Described herein is the use of variants of TdT to be used for nucleic acid synthesis, oligonucleotide synthesis, probe synthesis, tagging, nucleic acid amplification, aptamers, therapeutic nucleic acid molecules, drug target discovery and validation, disease diagnosis, metabolic engineering, data storage, crops improvement, library design, sequencing pools, nucleic acid labeling or attachment or any other application that is involving nucleic acid molecules.

Production of Variant TdTs

Variants of the invention may be produced by mutating known reference or wild type TdT-coding polynucleotides, then expressing it using conventional molecular biology techniques. For example, the mouse TdT gene (SEQ ID NO:1) may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or it may be directly cloned from mouse cells using protocols described by Boule et al, Mol. Biotechnology, 10: 199-208 (1998), or Bentolila et al, EMBO J., 14: 4221-4229 (1995); or the like.

For example, an isolated TdT gene may be inserted into an expression vector, such as pET32 (Novagen) to give a vector pCTdT which then may be used to make and express variant TdT proteins using conventional protocols. Vectors with the correct sequence may be transformed in E. coli producer strains.

Transformed strains are cultured using conventional techniques to pellets from which TdT protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h30 at 10,000 rpm. Centrifugate is pass through a 0.2 μm filter to remove any debris before column purification.

TdT protein may be purified from the centrifugate in a one-step affinity procedure. For example, Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDSPAGE gels.

Kits, Enzyme and Nucleotide Composition

A particular aspect of the invention is relative to the composition and the use of kits comprising a variant of TdT according to the invention, or to any particular aspect of the present invention, with optionally any combination of one or more components selected from: an initiating fragment, one or more reversible terminator nucleotides, additional enzyme and reagents used in a cleaving reaction. Said kits can be used in a method of enzymatic nucleic acid synthesis.

The present invention covers the composition of matter comprising variants of TdT according to the invention, or to any particular aspect of the present invention, with reversible modified nucleotide in a mix with appropriate buffer and ratio concentration.

EXAMPLES

Example 1—Generation, Expression and Purification of Variants of TdT According to the Invention Expression Strain Generation The TdT mouse gene has been generated from the pET28 plasmid described in [Boulé et al., 1998, *Mol. Biotechnol.* 10, 199-208]. Sequence SEQ ID N°4 (Tag TdT) has been amplified by using the following primers:

T7-pro: TAATACGACTCACTATAGGG (SEQ ID NO:5)
T7-ter: GCTAGTTATTGCTCAGCGG (SEQ ID NO:6)
through standard molecular biology techniques. The sequence is then cloned into plasmid pET32 backbone to give the new pCTdT plasmid.

After sequencing pCTdT is transformed into commercial *E. coli* cells, BL21 (DE3, from Novagen). Growing colonies on plate with kanamycin are isolated and named Ec-CTdT.

Polymerase Variants Generation

The pCTdT vector is used as starting vector. Specific primers comprising one or several point mutations have been generated from Agilent online software (http://www.genomics.agilent.com:80/primerDesignProgram.jsp). The commercially available kit QuickChange II (Agilent) has been used to generate the desired modified polymerase comprising the targeted mutations. Experimental procedure has followed the supplier's protocol. After generation of the different vectors, each of them have been sequenced. Vectors with the correct sequence have been transformed in *E. coli* producer strains, as described before. Clones able to grow on kanamycin LB-agar plates are isolated.

Expression

The Ec-CTdT and Ec-DSi or Ec-DSi' strains have been used for inoculating 250 ml erlens with 50 mL of LB media supplemented with appropriate amount of kanamycin. After overnight growth at 37° ° C., appropriate volumes of these pre-cultures have been used to inoculate 5L erlens with 2L LB media with kanamycin. The initial OD for the 5L cultures is chosen to be 0.01. The erlens are put at 37° C. under strong agitation and the OD of the different cultures are regularly checked. After reaching an OD comprised between 0.6 and 0.9 each erlen is supplemented by the addition of 1 mL of 1M IPTG (Isopropyl β-D-1-thiogalactopyranoside, Sigma). The erlens are put back to agitation under a controlled temperature of 37° C. After overnight expression, the cells are harvested in several pellets. Pellets expressing the same variants are pooled and stored at −20° C., eventually for several months.

Extraction

Previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptocthanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h30 at 10,000 rpm. Centrifugate is pass through a 0.2 µm filter to remove any debris before column purification.

Purification

A one-step affinity procedure is used to purify the produced and extracted polymerase enzymes. A Ni-NTA affinity column (GE Healthcare) is used to bind the polymerases. Initially the column has been washed and equilibrated with 15 column volumes of 50 mM tris-HCL (Sigma) pH 7.5, 150 mM NaCl (Sigma) and 20 mM imidazole (Sigma). Polymerases are bound to the column after equilibration. Then a washing buffer, composed of 50 mM tris-HCL (Sigma) pH 7.5, 500 mM NaCl (Sigma) and 20 mM imidazole (Sigma), is applied to the column for 15 column volumes. After wash the polymerases are eluted with 50 mM tris-HCL (Sigma) pH 7.5, 500 mM NaCl (Sigma) and 0.5M imidazole (Sigma). Fractions corresponding to the highest concentration of polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 µL of various fraction of the purified enzymes are analyzed in SDS-PAGE gels.

Results are presented by FIG. 1. The gel shows, for each TdT (both variants and wild-type), the column flowthrough (FT) and the different fractions F1 to F4, corresponding to the elution peaks. A molecular weight marker (M) was also loaded in the gel. FIG. 1 shows that the variants of TdT according to the invention present a high purity level (about 90%) and a good expression as compared to TdT wild-type (see columns F2 and/or F3).

Example 2—Evaluation of the Activity of Variants of TdT with Fluorescent Primers Activity Test Elongation performance of TdT variants of SEQ ID NO: 2: DS11 (M63R+L131P+C173R+R207L+R325P+E328N) DS29(M63R+L131P+C173R+R207N+R325P+E328N), DS173 (M63R+C173R+R207L+R325P+E328N), DS659 (L131P+C173R+R207L+R325P+E328N), DS874 (C173G+R207L+R325P+E328L) generated, expressed and purified according to example 1 is evaluated through the following assay. All the results are compared with each other and with the wild type TdT enzyme (SEQ ID N°1) and to a control tube lacking any polymerase enzyme.

TABLE 7

Activity test

| Reagent | Concentration | Volume |
|---|---|---|
| H$_2$O | — | 12 µL |
| Activity Buffer | 10× | 2 µL |
| dNTP | 250 µM | 2 µL |
| Purified enzyme | 20 µM | 2 µL |
| Fluorescent primer DNA | 500 nM | 2 µL |

The Activity buffer comprises, for example, TdT reaction buffer (available from New England Biolabs) supplemented with CoCl2. Primer used is the following:

5'-AAAAAAAAAAAAAAGGGG-3' (SEQ ID NO:7)

The primer has also an ATTO fluorescent dye on the 5' extremity.

Nucleotides used (noted as dNTP in table 7) are 3'-O-amino-2',3'-dideoxynucleotides-5'-triphosphate (ONH2, Firebird Biosciences) such as 3'-O-amino-2',3'-dideoxyadenosine-5'-triphosphate for example.

For each different variant tested, one tube is used for the reaction. The reagents are added in the tube, starting from water, and then in the order of Table 7. After 30 min at 37° C. the reaction is stopped by addition of formamide (Sigma).

Analysis

The analysis is involving polyacrylamide gel analysis,. Samples from activity test are analyzed through polyacrylamide 16% (biorad) denaturing gel. Gels are made just before the analysis by pouring polyacrylamide inside glass plates and let it polymerize. The gel inside the glass plates is mounted on an adapted tank filed with TBE buffer (Sigma) for the electrophoresis step. The samples to be analyzed are loaded on the top of the gel. A tension of 500 to 2,000V is applied between the top and bottom of the gel for 3 to 6 h at room temperature. Once migrated according to the sample target size, system is dismounted, and gel fluorescence is scanned through the use of Typhoon instrument (GE Life Sciences). After image acquisition, ImageJ software (imagej.nih.gov/ij/) is used to analyze the percentage of incorporation of the modified nucleotides.

Figure 2:
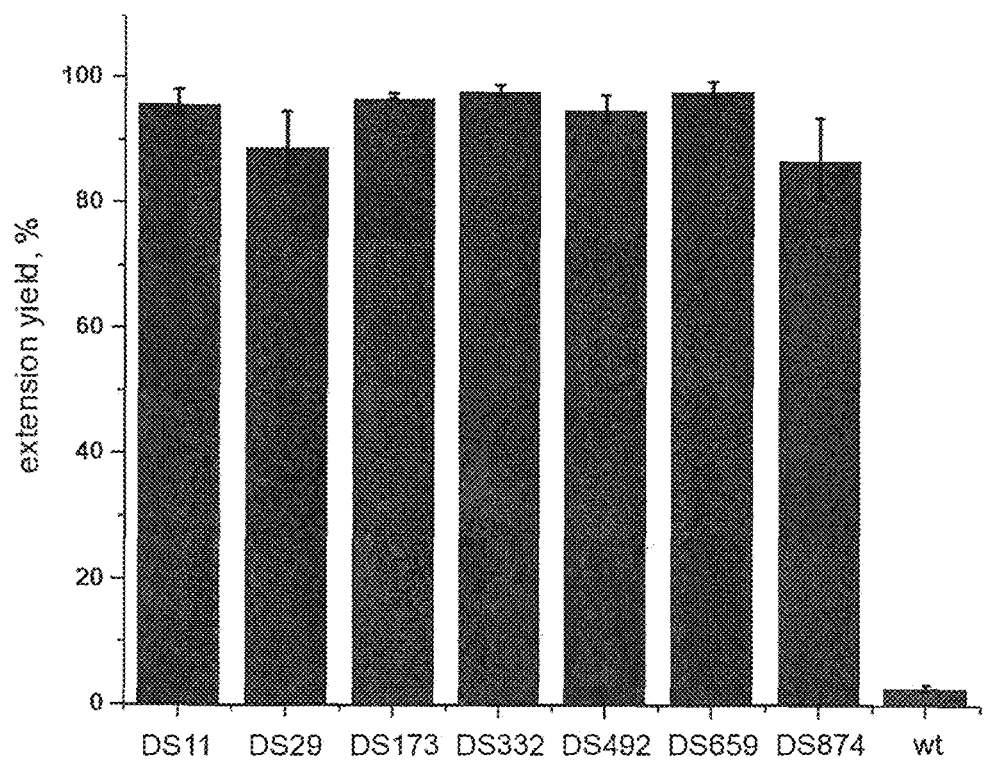
FIG. 2: Comparative results of performances for an elongation assay using wt TdT and TdT variants of the invention. The assay involves fluorescent labeled primers and 3'-O-amino reversible terminator modified nucleotides. The results represent mean value of n=3 experiments for each enzyme.

Results are showed on FIG. 2. For each variant, on the x-axis, the extension percentage has been evaluated as the quantity of expected elongated product over the total quantity of DNA loaded on the gel. Each experiment has been performed in triplicates. The bar hight, y-axis, corresponds to the mean value of those three exepriments. All the variants according to the invention show more than a 10-fold increase of activity compared to the wt enzyme, confirming the possibility of developing a nucleic acid synthesis technology with these variants.

Example 3—Evaluation of the Activity of Variants of TdT with Unlabeled Primer Activity Test Elongation performance of variants of SEQ ID NO: 2: DS928 (R207L+R325P+E328L) and DS950 (R207N+R325A+E328N) generated, expressed and purified according to example 1 was evaluated through the following assay. All the results are compared with a reference variant (SEQ ID N°9) obtained from previous research and to a control tube lacking any polymerase enzyme.

TABLE 8

Activity test

| Reagent | Concentration | Volume |
|---|---|---|
| H$_2$O | — | 12 µL |
| Activity Buffer | 10× | 2 µL |
| dNTP | 250 µM | 2 µL |
| Purified enzyme | 20 µM | 2 µL |
| Fluorescent primer DNA | 500 nM | 2 µL |

Primer used is the following:
5'-TTTTTTTTTTTTAAATAAGG-3' (SEQ ID NO:8)

Nucleotides used (noted as dNTP in table 8) were 3'-O-amino-2',3'-dideoxynucleotides-5'-triphosphate (ONH2, Firebird Biosciences) such as 3'-O-amino-2',3'-dideoxyadenosine-5'-triphosphate for example.

For each variant tested one tube was used for the reaction. The reagents were added in the tube starting from the water and then in the order of Table 8. After 30 min at 37° C. the reaction was stopped by addition of formamide (Sigma).

Analysis

The analysis used liquid chromatography and mass spectrometer detection and quantification (LC/MS). Samples from activity test were analyzed through LC/MS. Samples were loaded into the LC/MS instrument and a standard oligonucleotide separation method was performed. Acquisition of data was followed by deconvolution and spectrum calculation.

Figure 3:
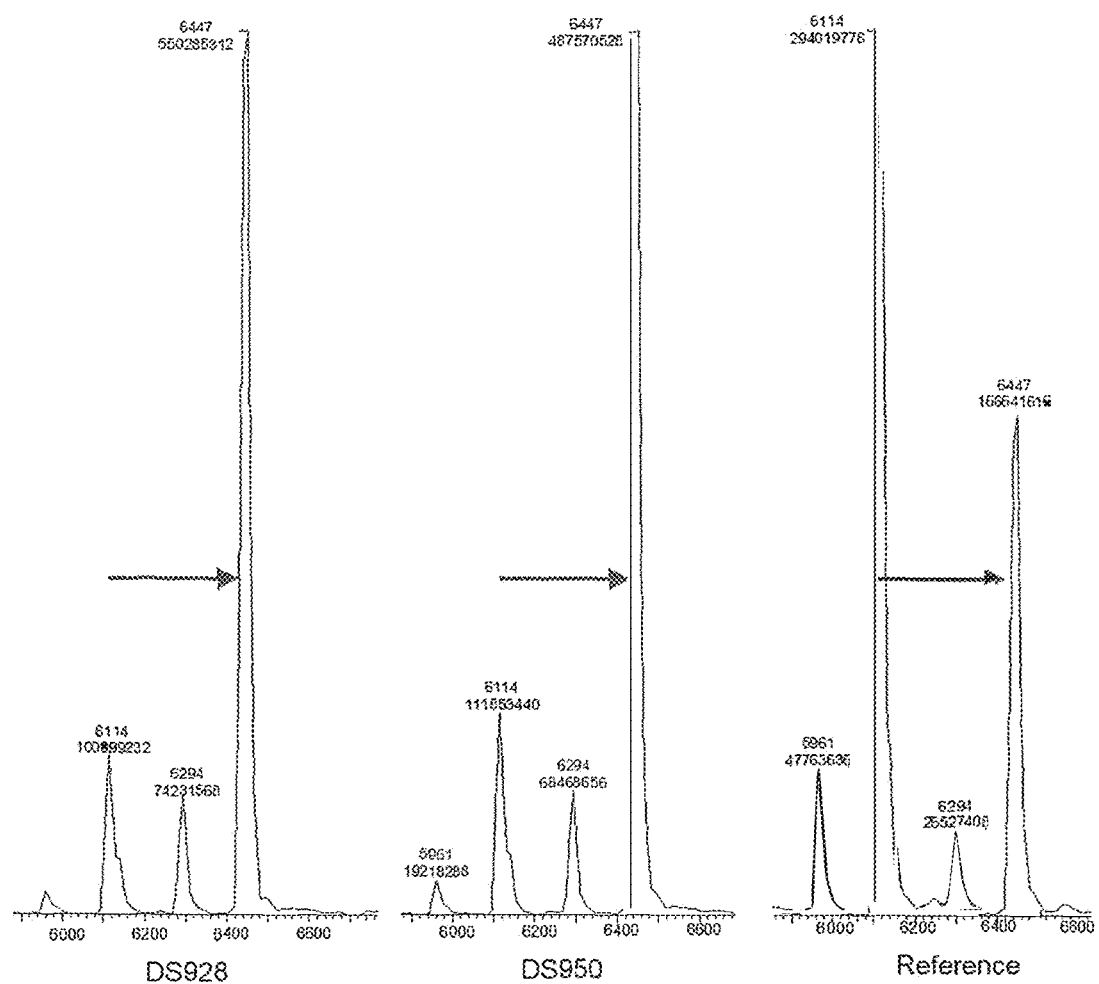
FIG. 3: Mass spectrum analysis of the results obtained for the elongation assay with different TdT variants of the invention. Only the relevant part of the mass spectrum is shown. The arrow shows the peak (mass) for the expected elongated primer.

Results are showed on FIG. 3. The spectrums correspond to the extension analysis of variants DS928, DS950 and references respectively. Initial primer mass is around 6114 and the expected extended product mass is around 6447 (emphasized by the arrows). The intensity of the signal (i.e., the hight of the peaks) may be directly correlated to the quantity of material. Both variants DS928, DS950 show significant improvement in the elongation of the starting primer as compared to the reference variant. These results confirm that the new variants according to the invention bring indisputable improvement over the TdT of the prior art.

The invention claimed is:

1. A variant of Terminal deoxynucleotidyl Transferase (TdT) which (i) comprises an amino acid substitution selected from C173G/R/P/A/V/S/N/Q/D wherein the position is numbered by reference to the amino acid sequence set forth in SEQ ID NO:2, (ii) is capable of synthesizing a nucleic acid fragment without template, and (iii) is capable of incorporating a modified nucleotide into the nucleic acid fragment.

2. The TdT variant of claim 1, wherein the modified nucleotide is a 3'-O-NH2-nucleoside triphosphate, a 3'-O-azidomethyl-nucleoside triphosphate, a 3'-O-allyl-nucleoside triphosphate, a 3'-O-(2-nitrobenzyl)-nucleoside triphosphate, or a 3'-O-propargyl-nucleoside triphosphate.

3. The TdT variant of claim 1, wherein the modified nucleotide is incorporated onto a free 3'-hydroxyl of a nucleic acid fragment.

4. The TdT variant of claim 1, further comprising a substitution of methionine at position 63.

5. The TdT variant of claim 1, further comprising a substitution of arginine at position 207.

6. The TdT variant of claim 1, further comprising a substitution of arginine at position 325.

7. The TdT variant of claim 1, further comprising a substitution of glutamic acid at position 328.

8. The TdT variant of claim 4, wherein said substitution of said methionine is R, Q, G, A, V, D, N, H or E.

9. The TdT variant of claim 5, wherein the substitution of the arginine is N, L, K, H, G, D, A or P.

10. The TdT variant of claim 6, wherein the substitution of the arginine is P, N, A, L, K, H, G or D.

11. The TdT variant of claim 7, wherein the substitution of the glutamic acid is N, L, T or S.

12. The TdT variant of claim 1, wherein the TdT variant comprises M63R, C173R, R207L, R325A, and E328L.

13. A nucleic acid encoding a TdT variant as defined in claim 1.

14. A method of producing a TdT variant comprising:
(a) culturing a host cell comprising a nucleic acid according to claim 12 under conditions suitable to express the nucleic acid encoding the TdT variant; and optionally
(b) recovering said TdT variant from the cell culture.

* * * * *